US010385091B2

(12) United States Patent
Patel et al.

(10) Patent No.: US 10,385,091 B2
(45) Date of Patent: *Aug. 20, 2019

(54) COMPOSITIONS AND METHODS FOR ALTERING SECOND MESSENGER SIGNALING

(71) Applicants: Memorial Sloan Kettering Cancer Center, New York, NY (US); The Rockefeller University, New York, NY (US); Rutgers, The State University of New Jersey, New Brunswick, NJ (US); University of Bonn, Bonn (DE)

(72) Inventors: Dinshaw J. Patel, Dobbs Ferry, NY (US); Thomas Tuschl, New York, NY (US); Manuel Ascano, Jr., New York, NY (US); Yang Wu, New York, NY (US); Yizhou Liu, New York, NY (US); Winfried Barchet, Bonn (DE); Gunther Hartmann, Bonn (DE); Thomas Zillinger, Bonn (DE); Roger Jones, Martinsville, NJ (US); Barbara L. Gaffney, Hillsborough, NJ (US); Pu Gao, New York, NY (US)

(73) Assignees: Memorial Sloan Kettering Cancer Center, New York, NY (US); The Rockefeller University, New York, NY (US); Rutgers, The State University of New Jersey, New Brunswick, NJ (US); University of Bonn, Bonn (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/718,753

(22) Filed: Sep. 28, 2017

(65) Prior Publication Data

US 2018/0118777 A1    May 3, 2018

Related U.S. Application Data

(62) Division of application No. 14/787,611, filed as application No. PCT/US2014/035909 on Apr. 29, 2014, now Pat. No. 9,840,533.

(60) Provisional application No. 61/819,369, filed on May 3, 2013, provisional application No. 61/817,269, filed on Apr. 29, 2013.

(51) Int. Cl.
| | |
|---|---|
| *C07D 519/00* | (2006.01) |
| *C07H 21/00* | (2006.01) |
| *A61K 31/522* | (2006.01) |
| *G16B 15/00* | (2019.01) |
| *G16B 20/00* | (2019.01) |
| *C07F 9/6574* | (2006.01) |
| *C12Q 1/48* | (2006.01) |
| *G06K 9/00* | (2006.01) |
| *G06K 9/46* | (2006.01) |
| *A61K 47/55* | (2017.01) |

(52) U.S. Cl.
CPC ........... *C07H 21/00* (2013.01); *A61K 31/522* (2013.01); *A61K 47/55* (2017.08); *C07F 9/65746* (2013.01); *C12Q 1/485* (2013.01); *G06K 9/00147* (2013.01); *G06K 9/46* (2013.01); *G16B 15/00* (2019.02); *G16B 20/00* (2019.02); *C12Y 207/07* (2013.01); *G01N 2500/04* (2013.01); *G01N 2500/10* (2013.01)

(58) Field of Classification Search
CPC .................................................. C07D 519/00
USPC ........................................................ 514/47
See application file for complete search history.

(56) References Cited

U.S. PATENT DOCUMENTS

| | | | |
|---|---|---|---|
| 5,547,941 A | 8/1996 | Battistini et al. | |
| 5,637,483 A | 6/1997 | Dranoff et al. | |
| 5,698,432 A | 12/1997 | Oxford | |
| 5,904,920 A | 5/1999 | Dranoff et al. | |
| 5,985,290 A | 11/1999 | Jaffee et al. | |
| 6,033,674 A | 3/2000 | Jaffee et al. | |
| 6,090,611 A | 7/2000 | Covacci et al. | |
| 6,183,121 B1 | 2/2001 | Kim et al. | |
| 6,277,368 B1 | 8/2001 | Hiserodt et al. | |
| 6,350,445 B1 | 2/2002 | Jaffee et al. | |
| 6,464,973 B1 | 10/2002 | Levitsky et al. | |
| 6,558,670 B1 | 5/2003 | Friede et al. | |
| 6,780,429 B1 | 8/2004 | Matsuyama et al. | |
| 7,569,555 B2 | 8/2009 | Karaolis | |
| 7,592,326 B2 | 9/2009 | Karaolis | |
| 7,709,458 B2 | 5/2010 | Karaolis et al. | |
| 8,012,469 B2 | 9/2011 | Levitsky et al. | |
| 8,283,328 B2 | 10/2012 | Krieg et al. | |
| 8,304,396 B2 | 11/2012 | Krieg et al. | |
| 8,367,716 B2 | 2/2013 | Karaolis | |
| 8,450,293 B2 | 5/2013 | Jones et al. | |
| 9,061,048 B2 | 6/2015 | Portnoy et al. | |

(Continued)

FOREIGN PATENT DOCUMENTS

| | | |
|---|---|---|
| CN | 102199183 A | 9/2011 |
| JP | 2004511527 A | 4/2004 |

(Continued)

OTHER PUBLICATIONS

U.S. Appl. No. 15/836,763, filed May 10, 2018, Patel et al.

(Continued)

*Primary Examiner* — Jeffrey H Murray
(74) *Attorney, Agent, or Firm* — Choate, Hall & Stewart LLP; John P. Rearick; Erica M. D'Amato

(57) ABSTRACT

The invention relates to compositions, methods, kits, and assays related to the use and/or exploitation of isomers of cGAMP as well as the structure of the enzyme cGAS.

29 Claims, 22 Drawing Sheets

Specification includes a Sequence Listing.

(56) References Cited

U.S. PATENT DOCUMENTS

| | | |
|---|---|---|
| 9,090,646 B2 | 7/2015 | Jones et al. |
| 9,549,944 B2 | 1/2017 | Dubensky, Jr. et al. |
| 9,597,391 B2 | 3/2017 | Ebensen et al. |
| 9,695,212 B2 | 7/2017 | Dubensky, Jr. et al. |
| 9,718,848 B2 | 8/2017 | Adams et al. |
| 9,724,408 B2 | 8/2017 | Dubensky, Jr. et al. |
| 9,840,533 B2 * | 12/2017 | Patel .................. C07F 9/65746 |
| 9,994,607 B2 | 6/2018 | Adams et al. |
| 10,011,630 B2 | 7/2018 | Vernejoul et al. |
| 10,047,115 B2 | 8/2018 | Biggadike et al. |
| 10,092,644 B2 | 10/2018 | Yan et al. |
| 10,106,574 B2 | 10/2018 | Altman et al. |
| 10,131,686 B2 | 11/2018 | Patel et al. |
| 10,176,292 B2 | 1/2019 | Patel et al. |
| 10,189,873 B2 | 1/2019 | Dubensky, Jr. et al. |
| 2001/0041682 A1 | 11/2001 | Stutts et al. |
| 2002/0140414 A1 | 10/2002 | Sohn et al. |
| 2003/0003092 A1 | 1/2003 | Krissansen et al. |
| 2003/0138413 A1 | 7/2003 | Vicari et al. |
| 2006/0040887 A1 | 2/2006 | Karaolis |
| 2006/0286549 A1 | 12/2006 | Sohn et al. |
| 2007/0059683 A1 | 3/2007 | Barber et al. |
| 2007/0155766 A1 | 7/2007 | Zheng et al. |
| 2007/0224210 A1 | 9/2007 | Krieg et al. |
| 2007/0244059 A1 | 10/2007 | Karaolis |
| 2007/0281897 A1 | 12/2007 | Karaolis |
| 2008/0076778 A1 | 3/2008 | Ossovskaya et al. |
| 2008/0286296 A1 | 11/2008 | Ebensen et al. |
| 2010/0150946 A1 | 6/2010 | Jooss et al. |
| 2010/0310602 A1 | 12/2010 | Reed et al. |
| 2011/0081674 A1 | 4/2011 | Han et al. |
| 2011/0262485 A1 | 10/2011 | Barber |
| 2011/0287948 A1 | 11/2011 | Suresh et al. |
| 2012/0041057 A1 | 2/2012 | Jones et al. |
| 2012/0164107 A1 | 6/2012 | Portnoy et al. |
| 2012/0178710 A1 | 7/2012 | Jones et al. |
| 2014/0155345 A1 | 6/2014 | Jones et al. |
| 2014/0205653 A1 | 7/2014 | Dubensky, Jr. et al. |
| 2014/0329889 A1 | 11/2014 | Vance et al. |
| 2014/0341976 A1 | 11/2014 | Dubensky, Jr. et al. |
| 2015/0056224 A1 | 2/2015 | Dubensky, Jr. et al. |
| 2016/0068560 A1 | 3/2016 | Patel et al. |
| 2016/0210400 A1 | 7/2016 | Patel et al. |
| 2017/0218008 A1 | 8/2017 | Dubensky, Jr. et al. |
| 2017/0283454 A1 | 10/2017 | Dubensky, Jr. et al. |
| 2018/0127454 A1 | 5/2018 | Patel et al. |

FOREIGN PATENT DOCUMENTS

| | | |
|---|---|---|
| JP | 2009544754 A | 12/2009 |
| WO | WO-02/32450 A2 | 4/2002 |
| WO | WO-2005/030186 A2 | 4/2005 |
| WO | WO-2005/039535 A1 | 5/2005 |
| WO | WO-2005/087238 A2 | 9/2005 |
| WO | WO-2005/089777 A1 | 9/2005 |
| WO | WO-2007/054279 A2 | 5/2007 |
| WO | WO-2007/064945 A2 | 6/2007 |
| WO | WO-2008/016473 A2 | 2/2008 |
| WO | WO-2009/133560 A1 | 11/2009 |
| WO | WO-2010/017248 A2 | 2/2010 |
| WO | WO-2010/067262 A1 | 6/2010 |
| WO | WO-2010/104883 A1 | 9/2010 |
| WO | WO-2011/003025 A1 | 1/2011 |
| WO | WO-2011/136828 A1 | 11/2011 |
| WO | WO-2011/139769 A2 | 11/2011 |
| WO | WO-2012/088155 A1 | 6/2012 |
| WO | WO-2012/139209 A1 | 10/2012 |
| WO | WO-2013/086331 A1 | 6/2013 |
| WO | WO-2013/166000 A1 | 11/2013 |
| WO | WO-2013/185052 A1 | 12/2013 |
| WO | WO-2014/093936 A1 | 6/2014 |
| WO | WO-2014/099824 A1 | 6/2014 |
| WO | WO-2014/179335 A1 | 11/2014 |
| WO | WO-2014/179760 A1 | 11/2014 |
| WO | WO-2014/189805 A1 | 11/2014 |
| WO | WO-2014/189806 A1 | 11/2014 |
| WO | WO-2015/017652 A1 | 2/2015 |
| WO | WO-2015/061294 A2 | 4/2015 |
| WO | WO-2015/074145 A1 | 5/2015 |
| WO | WO-2015/077354 A1 | 5/2015 |
| WO | WO-2015/108595 A1 | 7/2015 |
| WO | WO-2015/185565 A1 | 12/2015 |

OTHER PUBLICATIONS

Abe et al., STING Recognition of Cytoplasmic DNA Instigates Cellular Defense, Mol Cell., 50(1):5-15 (2013).

Ablasser, A. et al. cGAS produces a 2'-5'-linked cyclic dinucleotide second messenger that activates STING, Nature 498, 382-384 (2013).

Adams, P.D. et al., PHENIX: a comprehensive Python-based system for macromolecular structure solution, Acta Crystallogr. D Biol. Crystallogr., 66:213-221 (2010).

Adler-Moore, J. et al., Characterization of the murine Th2 response to immunization with liposomal M2e influenza vaccine, Vaccine, 29:4460-4468 (2011).

Ahmed, S.S. et al., Assessing the safety of adjuvanted vaccines, Science Translation Medicine, 3(93):1-12 (2011).

Ahn et al., STING manifests self DNA-dependent inflammatory disease. Proc Natl Acad Sci U S A. Nov. 20, 2012;109(47):19386-19391.

Antonarakis, E.S. and Drake, C.G., Combining immunological and androgen-directed approaches: an emerging concept in prostate cancer immunotherapy, Current Opinion in Oncology, 24(3):258-265 (2012).

Apetoh et al., Toll-like receptor 4-dependent contribution of the immune system to anticancer chemotherapy and radiotherapy, Nat Med., (9):1050-1059 (2007).

Ausmees, N. et al., Genetic data indicate that proteins containing the GGDEF domain possess diguanylate cyclase activity, FEMS Microbiology Letters, 204(1):163-167 (2001).

Badovinac, V.P. et al., Accelerated CD8B+ T-cell memory and prime-boost response after dendritic-cell vaccination, Nature Medicine, 11(7):748-756 (2005).

Baguley, B.C., and Ching, L.M. DMXAA: an antivascular agent with multiple host responses, Int. J. Radiat. Oncol. Biol. Phys., 54:1503-1511 (2002).

Bahjat, K.S. et al., Activation of Immature Hepatic NK Cells as Immunotherapy for Liver Metastatic Disease, The Journal of Immunology, 179(11):7376-7384 (2007).

Bahjat, K.S. et al., Cytosolic entry controls CD8+-T-Cell potency during bacterial infection, Infection and Immunity, 74(11):6387-6397 (2006).

Bahjat, K.S. et al., Suppression of cell-mediated immunity following recognition of phagosome-confined bacteria, PLoS Pathogens, 5(9):e1000568 (2009).

Bala, I. et al., PLGA nanoparticles in drug delivery: the state of the art, Critical Reviews in Therapeutic Drug Carrier Systems, 21(5):387-422 (2004).

Baldwin, S. et al., The importance of adjuvant formulation in the development of a tuberculosis vaccine, The Journal of Immunology, 188(5):2189-2197 (2012).

Barber, G.N., Cytoplasmic DNA innate immune pathways, Immunological Reviews, 243(1):99-108 (2011).

Barber, G.N., STING-dependent signaling, Nature Immunology, 12(10):929-930 (2011).

Barker, J.R. et al., STING-Dependent recognition of cyclic di-AMP mediates type I interferon responses during Chlamydia trachomatis infection, mBio, 4(3):e00018-00013 (2013).

Battistini, C. et al., Stereoselective synthesis of cyclic dinucleotide phosphorothioates, Tetrahedron, 49(5):1115-1132 (1993).

Blank et al., PD-L1/B7H-1 Inhibits the Effector Phase of Tumor Rejection by T Cell Receptor(TCR) Transgenic CD8+ T Cells, Cancer Res., 64(3):1140-1145 (2004).

Blankenstein, T. et al., The determinants of tumour immunogenicity, Nature Reviews Cancer, 12(4):307-303 (2012).

(56) References Cited

OTHER PUBLICATIONS

Bowie, A.G. et al., Innate sensing of bacterial cyclic dinucleotides: more than just STING, Nature Immunology, 13(12):1137-1139 (2012).

Brahmer, J.R. et al., Phase I study of single-agent anti-programmed death-1 (MDX-1106) in refractory solid tumors: safety, clinical activity, pharmacodynamics, and immunologic correlates, Journal of Clinical Oncology, 28(19):3167-3175 (2010).

Brockstedt, D.G. et al., Killed but metabolically active microbes: a new vaccine paradigm for eliciting effector T-cell responses and protective immunity, Nature Medicine, 11(8):853-860 (2005).

Brockstedt, D.G. et al., Listeria-based cancer vaccines that segregate immunogenicity from toxicity, Proceedings of the National Academy of Sciences, U.S.A., 101(38):13832-13837 (2004).

Burckstummer, T. et al., An orthogonal proteomic-genomic screen identifies AIM2 as a cytoplasmic DNA sensor for the inflammasome, Nat. Immunol., 10:266-272 (2009).

Burdette, D.L., and Vance, R.E. Sting and the innate immune response to nucleic acids in the cytosol, Nat. Immunol., 14:19-26 (2013).

Burdette, D.L., et al. STING is a direct innate immune sensor of cyclic di-GMP, Nature, 478: 515-518 (2011).

Burger's Medicinal Chemistry and Drug Discovery, Fifth Edition, published by Wiley-Interscience, edited by Manfred E. Wolff, pp. 975-977 (1994).

Cai, X. et al. The cGAS-cGAMP-STING Pathway of Cytosolic DNA Sensing and Signaling, Mol. Cell, 54:289-296 (2014).

Cavlar, T. et al. Species-specific detection of the antiviral small-molecule compound CMA by STING, EMBO J., 32:1440-1450 (2013).

Chan, C. et al., Structural basis of activity and allosteric control of diguanylate cyclase, Proceedings of the National Academy of Sciences of the United States of America, 101(49):17084-9 (2004).

Chen, W. et al., The potential of 3',5'-cyclic diguanylic acid (c-di-GMP) as an effective vaccine adjuvant, Vaccine, 28(18):3080-3085 (2010).

Civril, F. et al. Structural mechanism of cytosolic DNA sensing by cGAS, Nature, 498:332-337 (2013).

Coffman, R.L. et al., Vaccine adjuvants: putting innate immunity to work, Immunity, 33(4):492-503 (2010).

Coler, R.N. et al., Development and characterization of synthetic glucopyranosyl lipid adjuvant system as a vaccine adjuvant, PLoS One, 6(1):e16333 (2011).

Conlon, J., et al. Mouse, but not human STING, binds and signals in response to the vascular disrupting agent 5,6-Dimethylxanthenone-4-Acetic Acid, J. Immunol., 190:5216-5225 (2013).

Corrales et al., Extremely potent immunotherapeutic activity of a STING agonist in the B16 melanoma model in vivo, J. ImmunoTherapy, 1:1 (2013).

Coughlin, J.E. et al., Orally bioavailable anti-HBV dinucleotide acyloxyalkyl prodrugs, Bioorganic & Medicinal Chemistry Letters, 20(5):1783-1786 (2010).

Creighton, T.E. et al., Mechanisms and catalysts of disulfide bond formation in proteins, Trends in Biotechnology, 13(1):18-23 (1995).

Crimmins, G.T. et al., Listeria monocytogenes multidrug resistance transporters activate a cytosolic surveillance pathway of innate immunity, Proceedings of the National Academy of Sciences, U.S.A., 105(29):10191-10196 (2008).

Crittenden, M. et al., Expression of inflammatory chemokines combined with local tumor destruction enhances tumor regression and long-term immunity, Cancer Research, 63(17):5505-5512 (2003).

Curran, M.A. and Allison, J.P., Tumor vaccines expressing Flt3 ligand synergize with CTLA-4 blockade to reject dreimplanted tumors, Cancer Research, 69(19):7747-7755 (2009).

Dai, P. et al. Modified vaccinia virus Ankara triggers type I IFN production in murine conventional dendritic cells via a cGAS/STING-mediated cytosolic DNA-sensing pathway, PLoS Pathog., 10:e1003989 (2014).

Dalby, B. et al., Advanced transfection with Lipofectamine 2000 reagent: primary neurons, siRNA, and high-throughput applications, Methods, 33(2):95-103 (2004).

Danilchanka, O. and Mekalanos, J. J., Cyclic Dinucleotides and the Innate Immune Response, Cell, 154:962-970 (2013).

Davies, B.W. et al., Coordinated regulation of accessory genetic elements produces cyclic di-nucleotides for V. cholerae virulence, Cell, 149:358-370 (2012).

De Grujil, T.D. et al., Whole-cell cancer vaccination: from autologous to allogeneic tumor- and dendritic cell-based vaccines, Cancer Immunology Immunotherapy, 57:1569-1577 (2008).

Desmet, C.J. and Ishii, K.J., Nucleic acid sensing at the interface between innate and adaptive immunity in vaccination, Nature Reviews Immunology, 12(7):479-491 (2012).

Dessureault, S. et al., A phase-I trial using a universal GM-CSF-producing and CD40L-expressing bystander cell line (GM.CD40L) in the formulation of autologous tumor cell-based vaccines for cancer patients with stage IV disease, Annals of Surgical Oncology, 14(2):869-884 (2007).

Di Lorenzo, G. et al., Immunotherapy for the treatment of prostate cancer, Nature Reviews Clinical Oncology, 8:551-561 (2011).

Diamond et al., Type I interferon is selectively required by dendritic cells for immune rejection of tumors, J. Exp. Med., 208(10):1989-2003 (2011).

Diner, E.J., et al. The innate immune DNA sensor cGAS produces a noncanonical cyclic dinucleotide that activates human STING, Cell reports, 3:1355-1361 (2013).

Donovan, J. et al., Structural basis for cytosolic double-stranded RNA surveillance by human oligoadenylate synthetase 1, Proc. Natl. Acad. Sci. USA, 110:1652-1657 (2013).

Drake, C.G. et al., Androgen ablation mitigates tolerance to a prostate/prostate cancer-restricted antigen, Cancer Cell, 7(3):239-249 (2005).

Dranoff, G. et al., Vaccination with irradiated tumor cells engineered to secrete murine granulocyte-macrophage colony-stimulating factor stimulates potent, specific, and long-lasting anti-tumor immunity, Proceedings of the National Academy of Sciences, 90(8):3539-3543 (1993).

Driessens, G. et al., Highly successful therapeutic vaccinations combining factor dendritic cells and tumor cells secreting granulocyte macrophage colony-stimulating factor, Cancer Research, 64(22):8435-8442 (2004).

Dubensky, oral slide presentation "Development of Cyclic Dinucleotides as STING-Targeted Molecular Adjuvants.". Immunological Mechanisms of Vaccination seminar, Fairmont Château Laurier, Ottawa, Ontario Canada, 13 pages (2012).

Dubensky, T.W. and Reed, S.G., Adjuvants for cancer vaccines, Seminars in Immunology, 22(3):155-161 (2010).

Dubensky, T.W. et al., Abstract 4573: A novel tumor vaccine with cyclic dinucleotides—can induce potent anti-tumor responses in vivo, Cancer Research, 73(8 Suppl):4573-4573 (2013).

Dubensky, T.W. et al., Rationale, progress, and development of vaccines utilizing STING-activating cyclic dinucleotide adjuvants, Therapeutic Advances in Vaccines, 1(4):131-143 (2013).

Eager, R. and Nemunaitis, J., GM-CSF gene-transduced tumor vaccines, Molecular Therapy, 12(1):18-27 (2005).

Ebensen, T. et al., Bis-(3',5')-cyclic dimeric adenosine monophosphate: Strong Th1/Th2/Th17 promoting mucosal adjuvant, Vaccine, 29(32):5210-5220 (2011).

Ebensen, T. et al., The bacterial second messenger cdiGMP exhibits promising activity as a mucosal adjuvant. Clinical and Vaccine Immunology, 14(8):952-958 (2007).

Ebensen, T. et al., The bacterial second messenger cyclic diGMP exhibits potent adjuvant properties, Vaccine, 25:1464-1469 (2007).

Egli, M. et al., Atomic-resolution structure of the cellulose synthase regulator cyclic diguanylic acid, Proc. Natl. Acad. Sci. USA, 87:3235-3239 (1990).

Einstein, M.H. et al., Comparison of the immunogenicity and safety of Cervarix and Gardasil human papillomavirus (HPV) cervical cancer vaccines in healthy women aged 18-45 years, Human Vaccines, 5(10):705-719 (2009).

(56) References Cited

OTHER PUBLICATIONS

Ekins, S. et al., In silico pharmacology for drug discovery: methods for virtual ligan screening and profiling, British Journal of Pharmacology, 152:9-20 (2007).
Emsley, P. et al., Features and development of Coot. Acta Crystallogr. D Biol. Crystallogr. 66, 486-501 (2010).
Ertem, G. and Ferris, J.P., Synthesis of RNA oligomers on heterogeneous templates, Nature, 379(6562):238-240 (1996).
Ettmayer, P. et al., Lessons learned from marketed and investigational prodrugs, Journal of Medicinal Chemistry, 47(10):2393-2404 (2004).
Fasso, M. et al., SPAS-1 (stimulator of prostatic adenocarcinoma-specific T cells)/SH3GLB2: A prostate tumor antigen dentified by CTLA-4 blockade, Proceedings of the National Academy of Sciences, U.S.A., 105(9):3509-3514 (2008).
Fernandes-Alnemri, T. et al., AIM2 activates the inflammasome and cell death in response to cytoplasmic DNA, Nature 458, 509-513 (2009).
Fridman et al., The immune contexture in human tumours: impact on clinical outcome. Nat Rev Cancer,12(4):298-306 (2012).
Fuertes et al., Host type I IFN signals are required for antitumor CD8+ T cell responses through CD8{alpha}+ dendritic cells, J. Exp Med., 208(10):2005-2016 (2011).
Fuertes et al., Type I IFN response and innate immune sensing of cancer, Trends Immunol. 34(2):67-73 (2013).
Fujii, G. et al., The VesiVax system: a method for rapid vaccine development, Frontiers in Bioscience, 13:1968-1980 (2008).
Gaffney, B.L. et al., One-flask syntheses of c-di-GMP and the [Rp,Rp] and [Rp,Sp] thiophosphate analogues, Organic Letters, 12(14):3269-71 (2010).
Gaffney, B.L., and Jones, R.A. One-flask syntheses of cyclic diguanosine monophosphate (c-di-Gmp), Current Protocols in Nucleic Acid Chemistry 14, 14.18.11-14.18.17 (2012).
Gajewski et al., Cancer immunotherapy strategies based on overcoming barriers within the tumor microenvironment, Curr. Opin. Immunol., 25(2):268-276 (2013).
Gajewski et al., Gene Signature in Melanoma Associated With Clinical Activity: A Potential Clue to Unlock Cancer Immunotherapy, Cancer J., 16(4):399-403 (2010).
Gajewski, Identifying and Overcoming Immune Resistance Mechanisms in the Melanoma Tumor Microenvironment, Clin. Cancer Res., 12(7 Pt 2):2326s-2330s (2006).
Gall, A., et al. Autoimmunity initiates in nonhematopoietic cells and progresses via lymphocytes in an IFN-dependent autoimmune disease, Immunity, 36:120-131 (2012).
Galon, J. et al., Type, Density, and Location of Immune Cells Within Human Colorectal Tumors Predict Clinical Outcome, Science, 313(5795):1960-1964 (2006).
Gao, J. et al., GM-CSF-surface-modified B16.F10 melanoma cell vaccine, Vaccine, 24(25):5265-5268 (2006).
Gao, P. et al., Cyclic [G(2',5')pA(3',5')p] is the metazoan second messenger produced by DNA-activated cyclic GMP-AMP synthase, Cell, 153(5):1094-1107 (2013).
Gao, P., et al. Binding-pocket and lid-region substitutions render human STING sensitive to the species-specific drug DMXAA, Cell Rep., 8(6):1668-1676 (2014).
Gao, P., et al. Structure-Function Analysis of STING Activation by c[G(2',5') pA(3',5')p] and Targeting by Antiviral DMXAA, Cell, 154:748-762 (2013).
Gehrke, N., et al. Oxidative Damage of DNA Confers Resistance to Cytosolic Nuclease TREX1 Degradation and Potentiates STING-Dependent Immune Sensing, Immunity, 39:482-495 (2013).
Ghiringhelli et al., Activation of the NLRP3 inflammasome in dendritic cells induces IL-1beta-dependent adaptive immunity against tumors, Nat. Med., 15(10):1170-1178 (2009).
Goldberg, M.V. et al., Role of PD-1 and its ligand, B7-H1, in early fate decisions of CD8 T cells, Blood, 110(1):186-192 (2007).
Grajkowski, A. et al., Convenient synthesis of a propargylated cyclic (3'-5') diguanylic acid and its "Click" conjugation to a biotinylated azide, Bioconjugate Chemistry, 21(11):2147-2152 (2010).
Gray et al., Evidence for cyclic diguanylate as a vaccine adjuvant with novel immunostimulatory activities, Cell Immunol., 278(1-2):113-119 (2012).
Gulley, J.L. et al., Immunologic and prognostic factors associated with overall survival employing a poxviral-based DSA vaccine in metastatic castrate-resistant prostate cancer, Cancer Immunology Immunotherapy, 59(5):663-674 (2010).
Hamid et al., A prospective phase II trial exploring the association between tumor microenvironment biomarkers and clinical activity of ipilimumab in advanced melanoma, J. Transl. Med., 9:204 (2011).
Harlin et al., Chemokine Expression in Melanoma Metastases Associated with CD8+ T-Cell Recruitment, Cancer Res., 69(7):3077-3085 (2009).
Hartmann, R., et al., Crystal structure of the 2'-specific and double-stranded RNA-activated interferon-induced antiviral protein 2'-5'-oligoadenylate synthetase, Mol. Cell, 12:1173-1185 (2003).
Harty, J.T. and Badovinac, V.P., Shaping and reshaping CD8+ T-cell memory, Nature Reviews Immunology, 8(2):107-119 (2008).
Hayakawa Y., A facile synthesis of cyclic bis(3'→5')diguanylic acid., Tetrahedron, 59:6465-6471 (2003).
Head, M. and Jameson, M. B., The development of the tumor vascular-disrupting agent ASA404 (vadimezan, DMXAA): current status and future opportunities, Expert Opin. Inv. Drug, 19:295-304 (2010).
Henry et al., Type I interferon signaling is required for activation of the inflammasome during Francisella infection, J. Exp. Med., 204(5):987-994 (2007).
Hernandez, J.M. et al., Novel kidney cancer immunotherapy based on the granulocyte-macrophage colony-stimulating factor and carbonic anhydrase IX fusion gene, Clinical Cancer Research, 9(5):1906-1916 (2003).
Higashida, H. et al., Measurement of adenylyl cyclase by separating cyclic AMP on silica gel thin-layer chromatography, Anal. Biochem., 308:106-111 (2002).
Hodi, F.S. et al., Improved survival with ipilimumab in patients with metastatic melanoma, The New England Journal of Medicine, 363(8):711-723 (2010).
Hoebe et al., Upregulation of costimulatory molecules induced by lipopolysaccharide and double-stranded RNA occurs by Trif-dependent and Trif-independent pathways, Nat. Immunol., 4(12):1223-1229 (2003).
Hornung, V. and Latz, E., Intracellular DNA recognition, Nat. Rev. Immunol., 10:123-130 (2010).
Hornung, V. et al., AIM2 recognizes cytosolic dsDNA and forms a caspase-1-activating inflammasome with ASC, Nature, 458:514-518 (2009).
Howgate, P. and Hampton, A., Conversion of 2',3'-O-isopropylideneadenosine into 9-(6-deoxy-beta-D-allofuranosyl)- and 9-(6-deoxy-alpha-L-talofuranosyl)-adenines, Carbohydrate Research, 21:309-315 (1972).
Hu, D.L. et al., c-di-GMP as a vaccine adjuvant enhances protection against systemic methicillin-resistant *Staphylococcus aureus* (MRSA) infection, Vaccine, 27(35):4867-4873 (2009).
Huang, Y.H., et al. The structural basis for the sensing and binding of cyclic di-GMP by STING, Nat. Struct. Mol. Bio., 19:728-730 (2012).
Huang, Y.H., et al., Supplemental Information for the structural basis for the sensing and binding of cyclic di-GMP by STING, Nat. Struct. Mol. Bio., 5 pages. (2012).
Huffman, J.L. and Brennan, R.G. Prokaryotic transcription regulators: more than just the helix-turn-helix motif, Current Opinion in Structural Biology, 12:98-106 (2002).
Hughes, G.A., Nanostructure-mediated drug delivery, Nanomedicine, 1(1):22-30 (2005).
Hurwitz, A.A. et al., The TRAMP Mouse as a model for prostate cancer, Current Protocols in Immunolog., Chapter 20: Unit 20.5 (2001).
Hwang et al., Prognostic Significance of Tumor-infiltrating T-cells in Ovarian; Cancer: a Meta-analysis, Gynecol. Oncol., 124(2):192-198 (2012).
Hyodo, M. et al., Synthesis of cyclic bis(3'-5')diguanylic acid (c-di-GMP) analogs, Tetrahedron, 62:3089-3094 (2006).

(56) References Cited

OTHER PUBLICATIONS

International Search Report for PCT/US2014/035909 dated Sep. 12, 2014 (4 pages).
International Search Report for PCT/US2014/049140, 5 pages (dated Dec. 22, 2014).
Ishii et al., A Toll-like receptor-independent antiviral response induced by double-stranded B-form DNA, Nat. Immunol., 7(1):40-48 (2006).
Ishikawa, H. and Barber, G.N., STING is an endoplasmic reticulum adaptor that facilitates innate immune signaling, Nature, 455:674-678 (2008).
Ishikawa, H. and Barber, G.N., The STING pathway and regulation of innate immune signaling in response to DNA pathogens, Cell Mol. Life Sci., 68(7):1157-1165 (2011).
Ishikawa, H., et al. STING regulates intracellular DNA-mediated, type I interferon-dependent innate immunity, Nature, 461:788-792 (2009).
Iwasaki, A. and Medzhitov, R., Regulation of adaptive immunity by the innate immune system, Science, 327(5963):291-295 (2010).
Jemal, A. et al., Cancer statistics, 2010, CA Cancer J. Clin, 60(5):277-300 (2010).
Jin, L. et al., Identification and Characterization of a Loss-of-Function Human MPYS Variant, Genes Immun., 12(4): 263-269 (2011).
Jin, L. et al., MPYS is required for IFN response factor 3 activation and type I IFN production in the response of cultured phagocytes to bacterial second messengers cyclic-di-AMP and cyclic-di-GMP, The Journal of Immunology, 187(5):2595-2601 (2011).
Jin, L., et al., MPYS, a novel membrane tetraspanner, is associated with major histocompatibility complex class II and mediates transduction of apoptotic signals, Mol. Cell Biol., 28:5014-5026 (2008).
Jin, T., et al. Structures of the HIN domain:DNA complexes reveal ligand binding and activation mechanisms of the AIM2 inflammasome and IFI16 receptor, Immunity, 36:561-571 (2012).
Jounai et al., Recognition of damage-associated molecular patterns related to nucleic acids during inflammation and vaccination, Front Cell Infect Microbiol., 2:168 (2013).
Kantoff, P.W. et al., Overall survival analysis of a phase II randomized controlled trial of a poxviral-based PSA-targeted immunotherapy in metastatic castration-resistant prostate cancer., Journal of Clinical Oncology, 28(7):1099-1105 (2010).
Kantoff, P.W. et al., Sipuleucel-T immunotherapy for castration-resistant prostate cancer, The New England Journal of Medicine, 363(5):411-422 (2010).
Karaolis, D.K.R. et al., Bacterial c-di-GMP is an immunostimulatory molecule, The Journal of Immunology, 178(4):2171-2181 (2007).
Karaolis, D.K.R. et al., Cyclic Di-GMP stimulates protective innate immunity in bacterial pneumonia, Infection and Immunity, 75(10):4942-4950 (2007).
Kastenmuller, K. et al., Protective T cell immunity in mice following protein-TLR7/8 agonist-conjugate immunization requires aggregation, type I IFN, and multiple DC subsets, The Journal of Clinical Investigation, 121(5):1782-1796 (2011).
Kasturi, P. S., et al. Programming the magnitude and persistence of antibody responses with innate immunity, Nature, 470: 543-547 (2011).
Kawai, T. and Akira, S., The role of pattern-recognition receptors in innate immunity: update on Toll-like receptors, Nature Immunology, 11(5):373-384 (2010).
Kawarada et al., NK- and CD8+T Cell-Mediated Eradication of Established Tumors by Peritumoral Injection of CpG-Containing Oligodeoxynucleotides, J. Immunol., 167(9):5247-5253 (2001).
Keating, S.E. et al. Cytosolic DNA sensors regulating type I interferon induction, Trends Immunol., 32:574-581 (2011).
Kerur, N., et al. IFI16 acts as a nuclear pathogen sensor to induce the inflammasome in response to Kaposi Sarcoma-associated herpesvirus infection, Cell Host Microbe, 9:363-375 (2011).

Kim, J.J. et al., Co-crystal structures of PKG I-β (92-227) with cGMP and cAMP reveal the molecular details of cyclic-nucleotide binding, PLoS One, 6(4):e18413 (2011).
Kim, S., et al. Anticancer flavonoids are mouse-selective STING agonists, ACS Chem. Biol., 8: 1396-1401 (2013).
Kodym, R., et al. 2'-5'-Oligoadenylate synthetase is activated by a specific RNA sequence motif, Biochem. Biophys. Res. Commun., 388:317-322 (2009).
Konno et al., Cyclic Di Nucleotides Trigger ULK1 (ATG1) Phosphorylation of STING to Prevent Sustained Innate Immune Signaling, Cell, 155(3):688-698 (2013).
Kono and Rock, How dying cells alert the immune system to danger, Nat. Rev. Immunol., 8(4):279-289 (2008).
Krasteva, P.V. et al. Sensing the messenger: the diverse ways that bacteria signal through c-di-GMP, Protein Sci., 21:929-948 (2012).
Krishnamachari, Y. et al., Nanoparticle delivery systems in cancer vaccines, Pharm Res, 28:215-236 (2011).
Kroemer et al., Immunogenic Cell Death in Cancer Therapy, Annu. Rev. Immunol., 31:51-72 (2013).
Kubota, K. et al. Identification of 2'-phophodiesterase, which plays a role in 2-5A system reulated by interferon, J. Biol. Chem., 279:37832-37841 (2004).
Kulshina, N. et al. Recognition of the bacterial second messenger cyclic diguanylate by its cognate riboswitch, Nat. Struct. Mol. Biol., 16:1212-1217 (2009).
Lam, E.et al, Adenovirus detection by the cGAS/STING/TBK1 DNA sensing cascade, Journal of Virology, 88(2):974-981 (2014).
Lande et al., Plasmacytoid dendritic cells sense self-DNA coupled with antimicrobial peptide, Nature, 449(7162):564-569 (2007).
Lara, P.N., Jr., et al. Randomized phase III placebo-controlled trial of carboplatin and paclitaxel with or without the vascular disrupting agent vadimezan (ASA404) in advanced non-small-cell lung cancer, J. Clin. Oncol., 29:2965-2971 (2011).
Lauvau, G. et al., Priming of memory but not effector CD8 T cells by a killed bacterial vaccine, Science, 294(5547):1735-1739 (2009).
Le, D.T. et al., A live-attenuated Listeria Vaccine (ANZ-100) and a live-attenuated Listeria Vaccine expressing mesothelin (CRS-207) for advanced cancers: phase I studies of safety and immune induction, Clin. Cancer Res., 18(3):858-868 (2012).
Le, D.T. et al., Cellular vaccine approaches, Cancer J., 16(4):304-310 (2010).
Leber, J.H. et al., Distinct TLR- and NLR-Mediated transcriptional responses to an intracellular pathogen, PLoS Pathogens, 4(1):e6 (2008).
Lee, A.W. et al., A clinical grade cocktail of cytokines and PGE2 results in uniform maturation of human monocyte-derived dendritic cells: implications for immunotherapy, Vaccine, 20(Suppl 4):A8-A22 (2002).
Lee, E.R., et al. An allosteric self-splicing ribozyme triggered by a bacterial second messenger, Science, 329:845-848 (2010).
Li et al., Efficient Cross-presentation Depends on Autophagy in Tumor Cells, Cancer Res., 68(17):6889-6895 (2008).
Li, X. et al, Cyclic GMP-AMP synthase is activated by double-stranded DNA-induced oligomerization, Immunity, 39(6):1019-1031 (2013).
Libanova, R. et al., The member of the cyclic di-nucleotide family bis-(3', 5')-cyclic dimeric inosine monophosphate exerts potent activity as mucosal adjuvant, Vaccine, 28(10):2249-2258 (2010).
Libanova, R., Cyclic di-nucleotides: new era for small molecules as adjuvants, Microbial Biotechnology, 5(2):168-176 (2012).
Lubong Sabado, R. et al., In vitro priming recapitulates in vivo HIV-1 specific T cell responses, revealing rapid loss of virus reactive CD4+ T cells in acute HIV-1 infection, PLoS One, 4(1):e4256 (2009).
Lunde, B.M. et al. RNA-binding proteins: modular design for efficient function, Nat. Rev. Mol Cell. Biol., 8:479-490 (2007).
Luo, Y. et al, Selective binding of 2'-F-c-di-GMP to Ct-E88 and Cb-E43, new class I riboswitches from Clostridium tetani and Clostridium botulinum respectively, Molecular Biosystems, 9(6):1535-1539 (2013).
Lutz, E. et al., A lethally irradiated allogeneic granulocyte-macrophage colony stimulating factor-secreting tumor vaccine for

(56) References Cited

OTHER PUBLICATIONS pancreatic Adenocarcinoma: a phase II trial of safety, efficacy, and immune activation, Ann. Surg., 253(2):328-335 (2011).
Madhun, A.S. et al., Intranasal c-di-GMP-adjuvanted plant-derived H5 influenza vaccine induces multifunctional Th1 CD4+ cells and strong mucosal and systemic antibody responses in mice, Vaccine, 29(31):4973-4982 (2011).
Mahmoud et al., Tumor-Infiltrating CD8+ Lymphocytes Predict Clinical Outcome in Breast Cancer, J. Clin. Oncol., 29(15):1949-1955 (2011).
Marichal et al., DNA released from dying host cells mediates aluminum adjuvant activity, Nat Med., 17(8):996-1002 (2011).
Mathew, E. et al., Cytosolic delivery of antisense oligonucleotides by listeriolysin O-containing liposomes, Gene Therapy, 10(13):1105-1115 (2003).
McCoy, A.J. et al. Phaser crystallographic software, J. Appl. Crystallogr. 40, 658-674 (2007).
Mccune, C.S. et al., Active specific immunotherapy with tumor cells and Corynebacterium parvum: a phase I study, Cancer, 43(5):1619-1623 (1979).
Mckee et al., Host DNA released in response to aluminum adjuvant enhances MHC class II-mediated antigen presentation and prolongs CD4 T-cell interactions with dendritic cells. Proc Natl Acad Sci U S A., 110(12):E1122-E1131 (2013).
Mcwhirter, S.M. et al., A host type I interferon response is induced by cytosolic sensing of the bacterial second messenger cyclic-di-GMP, The Journal of Experimental Medicine, 206(9):1899-1911 (2003).
Mellman, I. et al., Cancer immunotherapy comes of age, Nature, 480(7378):480-489 (2011).
Meng, X-Y. et al, Molecular Docking: A powerful approach for structure-based drug discovery, Curr. Comput. Aided Drug Des., 7(2): 146-157 (2011).
Miyabe, H. et al., A new adjuvant delivery system 'cyclic di-GMP/YSK05 liposome' for cancer immunotherapy, Journal of Controlled Release, 184:20-27 (2014).
Molinero et al., Epidermal Langerhans cells promote skin allograft rejection in mice with NF-KB-impaired T cells, Am. J. Transplant., 8(1):21-31 (2008).
Muderhwa, J.M. et al., Oil-in-water liposomal emulsions: characterization and potential use in vaccine delivery, Journal of Pharmaceutical Sciences, 88(12):1332-1339 (1999).
Murshudov, G.N., et al. Refinement of macromolecular structures by the maximum-likelihood method, Acta. Crystallogr. D Biol. Crystallogr., 53:240-255 (1997).
Nelson, D.P. and Griswold, W.R., A computer program for calculating antibody affinity constants, Computer Methods and Programs in Biomedicine, 27(1):65-68 (1988).
Nelson, V. et al., Synthesis of Hypoxanthine, Guanine, and 6-Thiopurine Nucleosides of 6-Deoxy-D-allofuranose, J. Med. Chem., 26:1071-1074 (1983).
Neumann, F. et al., Identification of an HLA-DR-restricted peptide epitope with a promiscuous binding pattern derived from the cancer testis antigen HOM-MEL-40/SSX2, Int. J. Cancer, 112(4):661-668 (2004).
Nicoletto, M.O. et al., BRCA-1 and BRCA-2 mutations as prognostic factors in clinical practice and genetic counselling, Cancer Treatmeant Reviews, 27(5):295-304 (2001).
O'Neill, L.A., Immunology. Sensing the dark side of DNA, Science, 339(6121):763-4 (2013).
O'Riordan, M. et al., Innate recognition of bacteria by a macrophage cytosolic surveillance pathway, Proceedings of the National Academy of Science U.S.A., 99(21):13861-13866 (2002).
Obeid et al., Calreticulin exposure dictates the immunogenicity of cancer cell death, Nat. Med., 13(1):54-61 (2007).
Ogunniyi, A.D. et al., c-di-GMP is an effective immunomodulator and vaccine adjuvant against Pneumococcal infection, Vaccine, 26(36):4676-4685 (2008).

Oka et al., Mitochondrial DNA That Escapes from Autophagy Causes Inflammation and Heart Failure, Nature, 485(7397):251-255 (2012).
Olson, K. et al., Liposomal gD ectodomain (gD1-306) vaccine protects against HSV2 genital or rectal infection of female and male mice, Vaccine, 28(2):548-560 (2009).
Ora, M. et al., Hydrolytic reactions of cyclic bis(3'-5') diadenylics acid (c-di-AMP), Journal of Physical Organic Chemistry, 26: 218-225 (2013).
Otwinowski, Z., and Minor, W. Processing of X-ray Diffraction Data Collected in Oscillation Mode, Methods in Enzymology, 276:307-326 (1997).
Ouyang et al., Structural Analysis of the STING Adaptor Protein Reveals a Hydrophobic Dimer 1-3 Interface and Mode of Cyclic di-GMP Binding, Immunity, 36: 1073-1086 (2012).
Pagès et al., In Situ Cytotoxic and Memory T Cells Predict Outcome in Patients With Early-Stage Colorectal Cancer, J. Clin. Oncol., 27(35):5944-5951 (2009).
Paludan, S.R. and Bowie, A.G. Immune sensing of DNA, Immunity, 38:870-880 (2013).
Pardoll, D. and Drake, C., Immunotherapy earns its spot in the ranks of cancer therapy, The Journal of Experimental Medicine, 209(2):201-209 (2012).
Pardoll, D.M., The blockade of immune checkpoints in cancer immunotherapy, Nature Reviews Cancer, 12(4):252-264 (2012).
Parvatiyar, K. et al., DDX41 recognizes the bacterial secondary messengers cyclic di-GMP and cyclic di-AMP to activate a type I interferon immune response, Nat. Immunol., 13(12):1155-1161 (2012).
Pham, N.L.L. et al., Exploiting cross-priming to generate protective CD8 T-cell immunity rapidly, Proceedings of the National Academy of Sciences U.S.A., 107(27):12198-12203 (2010).
Porter, R. S., et al. 19th Edition Merck Manual, pp. 1059-1062 (2011).
Prantner, D., et al. 5,6-Dimethylxanthenone-4-acetic acid (DMXAA) activates stimulator of interferon gene (STING)-dependent innate immune pathways and is regulated by mitochondrial membrane potential, J. Biol. Chem., 287:39776-39788 (2012).
Rappuoli, R. et al., Vaccines for the twenty-first century society, Nature Reviews Immunology, 11(12):865-872 (2011).
Rasmussen, S.B., et al. Activation of autophagy by alpha-herpesviruses in myeloid cells is mediated by cytoplasmic viral DNA through a mechanism dependent on stimulator of IFN genes, J. Immunol., 187:5268-5276 (2011).
Reed, S.G. et al., New horizons in adjuvants for vaccine development, Trends in Immunology, 30(1):23-32 (2009).
Roberson and Walker, Immortalization of Cloned Mouse Splenic Macrophages with a Retrovirus Containing the v-raf/mil and v-myc Oncogenes, Cell Immunol., 116(2):341-351 (1988).
Roberts, Z. J., et al. IFN-beta-dependent inhibition of tumor growth by the vascular disrupting agent 5,6-dimethylxanthenone-4-acetic acid (DMXAA), J. Interf. Cytok. Res., 28:133-139 (2008).
Roembke, B.T. et al., A cyclic dinucleotide containing 2-aminopurine is a general fluorescent sensor for c-di-GMP and 3',3'-cGAMP, Molecular Biosystems, 10(6):1568-1575 (2014).
Romling, U. et al., Cyclic di-GMP: the First 25 Years of a Universal Bacterial Second Messenger, Microbiol. Mol. Biol. Rev. 77:1-52 (2013).
Ross, P. et al. Regulation of cellulose synthesis in Acetobacter xylinum by cyclic diguanylic acid, Nature, 325:279-281 (1987).
Ross, P. et al., The cyclic diguanylic acid regulatory system of cellulose synthesis in Acelobacter xylinum, Chemical Synthesis and Biological Activity of Cyclic Nucleotide Dimer, Trimer, and Phosphothioate Derivatives, The Journal of Biological Chemistry, 265(31):18933-18943 (1990).
Sadler, A.J., and Williams, B.R. Interferon-inducible antiviral effectors, Nat. Rev. Immunol., 8:559-568 (2008).
Sancho et al., Identification of a dendritic cell receptor that couples sensing of necrosis to immunity, Nature, 458(7240):899-903 (2009).
Sauer, J. D., et al. The N-ethyl-N-nitrosourea-induced Goldenticket mouse mutant reveals an essential function of Sting in the in vivo interferon response to Listeria monocytogenes and cyclic dinucleotides, Infect. Immun., 79:688-694 (2011).

(56) References Cited

OTHER PUBLICATIONS

Sawai, H. and Ohno, M., Synthesis of 2'-5' Linked Oligouridylates in Aqueous Medium Using the Pd2+ Ion, Chem. Pharm. Bull, 29(8):2237-2245 (1981).
Sawai, H. and Ohno, M., Synthesis of oligoinosinates with 2'-5' internucleotide linkage in aqueous solution using Pb2+ion, Bulletin of the Chemical Society of Japan, 54(9): 2759-2762 (1981).
Sawai, H. et al., Preparation and properties of oligocytidylates with 2'-5' internucleotide linkage, Bull Chem. Soc. Jpn., 58(1):361-366 (1985).
Schirmer, T., and Jenal, U. Structural and mechanistic determinants of c-di-GMP signaling, Nat. Rev. Microbiol., 7:724-735 (2009).
Schmidt, N. W. et al., Memory CD8 T cell responses exceeding a large but definable threshold provide long-term immunity to malaria, Proceedings of the National Academy of Sciences U.S.A., 105(37):14017-14022 (2008).
Schoggins, J.W., et al. A diverse range of gene products are effectors of the type I interferon antiviral response, Nature, 472:481-485 (2011).
Schwartz, K.T. et al., Hyperinduction of host beta interferon by a Listeria monocytogenes strain naturally overexpressing the multidrug efflux pump MdrT, Infection and Immunity, 80(4):1537-1545 (2012).
Seder, R.A. et al., T-cell quality in memory and protection: implications for vaccine design, Natural Reviews Immunology, 8(4):247-258 (2008).
Shanahan, C.A. et al., Differential analog binding by two classes of c-di-GMP riboswitches, J. Am. Chem. Soc., 133(39):15578-15592 (2011).
Shanahan, C.A. et al., Identification of c-di-GMP Derivatives Resistant to an EAL Domain Phosphodiesterase, Biochemistry, 52(2):365-377 (2013).
Shang, G., et al. Crystal structures of STING protein reveal basis for recognition of cyclic di-GMP, Nat. Struct. Mol. Bio., 19:725-727 (2012).
Sharma et al., Innate immune recognition of an AT-rich stem-loop DNA motif in the Plasmodium falciparum genome, Immunity, 35(2):194-207 (2011).
Shu, C. et al., Structure of STING bound to cyclic di-GMP reveals the mechanism of cyclic dinucleotide recognition by the immune system, Nature Structural and Molecular Biology, 19(7):722-4 (2012).
Silverman, the Organic Chemistry of Drug Design and Drug Action, Published by Academic Press, pp. 352-397 (1992).
Singh, S. et al., Non-replicating adenovirus vectors expressing avian influenza virus hemagglutinin and nucleocapsid proteins induce chicken specific effector, memory and effector memory CD8B(+) T lymphocytes, Virology, 405(1):62-69 (2010).
Singh, S. et al.. Avian influenza viral nucleocapsid and hemagglutinin proteins induce chicken CD8+ memory T lymphocytes, Virology, 399:231-23B (2010).
Skoberne, M. et al., KBMA Listeria monocytogenes is an effective vector for DC-mediated induction of antitumor immunity, J. Clin. Invest., 118(12):3990-4001 (2008).
Slansky et al., Enhanced Antigen-Specific Antitumor Immunity with Altered Peptide Ligands that Stabilize the MHC-Peptide-TCR Complex, Immunity, 13(4):529-538 (2000).
Smith, K.D. et al. Structural basis of ligand binding by a c-di-GMP riboswitch, Nat. Struct. Mol. Biol., 16:1218-1223 (2009).
Sofia, M.J. et al., Nucleoside, Nucleotide, and Non-Nucleoside Inhibitors of Hepatitis C Virus NS5B RNA—Dependent RNA;—Polymerase, J. Med. Chem., 55(6):248B1-2531 (2012).
Sofia, M.J., Nucleotide prodrugs for HCV therapy, Antiviral Chemistry & Chemotherapy, 22(1):23-49 (2011).
Spranger et al., Up-Regulation of PD-L 1, IDO, and Tregs in the Melanoma Tumor; Microenvironment Is Driven by CD8+ T Cells, Sci. Transl. Med., 5(200):200ra116 (2013).
Stella, V.J., Prodrugs and therapeutics, Expert Opinion on Therapeutic Patents, 14(3):277-280 (2004).

Stetson and Medzhitov, Recognition of Cytosolic DNA Activates an IRF3-Dependent Innate Immune Response, Immunity, 24(1):93-103 (2006).
Sudarsan, N. et al. Riboswitches in eubacteria sense the second messenger cyclic di-GMP, Science, 321: 411-413 (2008).
Sun, J.C. and Bevan, M.J., Defective COB T Cell memory following acute infection without CD4 T cell help, Science, 300(5617):339-342 (2003).
Sun, L. et al., Cyclic GMP-AMP synthase is a cytosolic DNA sensor that activates the type I interferon pathway, Science, 339(6121):786-91 (2013).
Sun, W. et al. ERIS, an endoplasmic reticulum IFN stimulator, activates innate immune signaling through dimerization, Proc. Natl. Acad. Sci. USA, 106:8653-8658 (2009).
Suzuki, N. et al., Practical synthesis of cyclic bis(3'-5')diadenylic acid (c-di-AMP), Chem. Lett, 40(10):1113-1114 (2011).
Takahashi, M. et al., Synthesis and characterization of 2'-modified-4'-thioRNA: a comprehensive comparison of nuclease stability, Nucleic Acids Research, 37(4):1353-1362 (2009).
Takaoka, A. et al. DAI (DLM-1/ZBP1) is a cytosolic DNA sensor and an activator of innate immune response, Nature, 448: 501-505 (2007).
Tamayo, R. et al., Roles of cyclic diguanylate in the regulation of bacterial pathogenesis, Annu. Rev Microbiol., 61:131-148 (2007).
Tanaka, Y. and Chen, Z.J., STING specifies IRF3 phosphorylation by TBK1 in the cytosolic DNA signaling pathway, Sci. Signal, 5(214):ra20 (2012).
Tannock et al., Docetaxel plus Prednisone or Mitoxantrone plus Prednisone for Advanced Prostate Cancer, N. Engl. J. Med., 351(15):1502-1512 (2004).
Testa, B. et al., Prodrug research: futile or fertile?, Biochemical Pharmacology, 68(11):2097-2106 (2004).
Tewari, K. et al., Poly(I:C) is an effective adjuvant for antibody and multi-functional CD4+ T cell responses to Plasmodium falciparum circumsporozoite protein (CSP) and alphaDEC-CSP in non human primates, Vaccine, 28(45):7256-7266 (2010).
Tezuka, T. et al., Synthesis of 2'-modified cyclic bis{3'-5')diadenylic acids {c-di-AMPs) and their promotion of cell division in a freshwater green alga, Chem. Lett., 41:1723-25 (2012).
Tijono et al., Identification of human-selective analogues of the vascular-disrupting agent 5,6-dimethylxanthenone-4-acetic acid (DMXAA), British Journal of Cancer, 108: 1036-1315 (2013).
Topalian, S.L. et al., Cancer immunotherapy comes of age, Journal of Clinical Oncology, 29(36):4828-4836 (2011).
Twitty et al., Tumor-Derived Autophagosome Vaccine: Induction of Cross Protective; Immune Responses Against Short-Lived Proteins Through a P62-Dependent Mechanism, Clin Cancer Res., 17(20):6467-6481 (2011).
Unterholzner, L. et al. IFI16 is an innate immune sensor for intracellular DNA, Nat. Immunol., 11: 997-1004 (2010).
Urata, H. et al., Regio- and Diastereo-Selectivity of Montmorillonite-Catalyzed Oligomerization of Racemic Adenosine 5'-Phosphorimidazolide, Nucleosides, Nucelotides and Nucleic Acvids, 27: 421-430 (2008).
Van Elsas, A. et al., Elucidating the autoimmune and antitumor effector mechnaisms of a treatment based on cytotoxic T lymphocyte antigen-4 blockade in combination with a B16 melanoma vaccine: comparison of prophylaxis and therapy, The Journal of Experimental Medicine, 194(4):481-489 (2001).
Van Erp, R. et al., Application of a sol particle immunoassay to the determination of affinity constants of monoclonal antibodies, Journal of Immunoassay, 12(3):425-443 (1991).
Vance, R.E. et al., Patterns of pathogenesis: discrimination of pathogenic and nonpathogenic microbes by the innate immune system, Cell Host & Microbe, 6(1):10-21 (2009).
Venes, D. et al., 21st Edition Taber's Cyclopedic Medical Dictionary, pp. 1163 (2009).
Waitz, R. et al., Potent induction of tumor immunity by combining tumor cryoablation withanti-CTLA-4 therapy, Cancer Research, 72(2):430-439 (2012).
Ward, E.S. et al., Binding activities of a repertoire of single immunoglobulin variable domains secreted from *Escherichia coli*, Nature, 341(6242):544-546 (1989).

(56) References Cited

OTHER PUBLICATIONS

Wille-Reece, U. et al., HIV Gag protein conjugated to a Toll-like receptor 7/8 agonist improves the magnitude and quality of Th1 and CD8+ T cell responses in nonhuman primates, Proceedings of the National Academy of Science U.S.A., 102 (42):15190-15194 (2005).
Wille-Reece, U. et al., Immunization with HIV-1 Gag protein conjugated to a TLR7/8 agonist results in the generation of HIV-1 Gag-specific Th1 and CD8+ T cell responses, The Journal of Immunology, 174(12):7676-7683 (2005).
Wille-Reece, U. et al., Toll-like receptor agonists influence the magnitude and quality of memory T cell responses after prime-boost immunization in nonhuman primates, The Journal of Experimental Medicine, 203(5):1249-1258 (2006).
Wilson, K.M. et al., Simplified conjugation chemistry for coupling peptides to F(ab') fragments: autologous red cell agglutination assay for HIV-1 antibodies, Journal of Immunological Methods, 175(2):267-273 (1994).
Witte, C.E. et al., Innate immune pathways triggered by Listeria monocytogenes and their role in the induction of cell-mediated immunity, Advances in Immunology, 113:135-156 (2012).
Wolchok et al., Nivolumab plus Ipilimumab in Advanced Melanoma, N. Engl. J. Med. 369(2):122-133 (2013).
Wolkowicz, U.M., and Cook, A.G. NF45 dimerizes with NF90, Zfr and SPNR via a conserved domain that has a nucleotidyltransferase fold, Nucleic Acids Res., 40:9356-9368 (2012).
Woodward, J.J. et al. c-di-AMP Secreted by Intracellular Listeria monocytogenes Activates a Host Type I Interferon Response. Science (New York, N.Y 328, 1703-1705 (2010).
Woodward, J.J. et al., Supporting online material for c-di-AMP secreted by intracellular Listeria monocytogenes activates a host type I interferon response, Science Express, 15 pages. (2010).
Woycechowsky, K.J. and Raines, R.T., Native disulfide bond formation in proteins, Curr Opin Chem Biol, (5):533-539 (2000).
Wu, J. et al., Corrected Supplemental Materials for Cyclic GMP-AMP is an Endogeneous Second Messenger in Innate Immune Signaling by Cytosolic DNA, Science, 21 pages. (2013).
Wu, J. et al., Cyclic GMP-AMP is an endogenous second messenger in innate immune signaling by cytosolic DNA. Science 339, 826-830 (2013).
Wu, J. et al., Supplemental Materials for Cyclic GMP-AMP is an Endogeneous Second Messenger in Innate Immune Signaling by Cytosolic DNA, Science, 6 pages (2013).
Xiao, T. S., and Fitzgerald, K. A. The cGAS-STING Pathway for DNA Sensing. Mol. Cell 51, 135-139 (2013).
Yan, H. and Aguilar, A.L., Synthesis of 3',5'-cyclic diguanylic acid (cdiGMP) using 1-(4-chlorophenyl)-4-ethoxypi peridin-4-yl as a protecting group for 2'-hydroxy functions of ribonucleosides, Nucleosides Nucleotides & Nucleic Acids, 26(2):189-204 (2007).
Yan, H. et al., Synthesis and immunostimulatory properties of the phosphorothioate analogues of cdiGMP, Bioorganic & Medicinal Chemistry Letters, 18(20):5631-5634 (2008).
Yanai et al., HMGB proteins function as universal sentinels for nucleic-acid-mediated innate immune responses, Nature, 462(7269):99-103 (2009).
Yang, P. et al. The cytosolic nucleic acid sensor LRRFIP1 mediates the production of type I interferon via a beta-catenin-dependent pathway, Nat. Immunol., 11: 487-494 (2010).
Yarmush, M.L. et al., Coupling of antibody-binding fragments to solid-phase supports: site-directed binding of F(ab')2 fragments, Journal of Biochemical and Biophysical Methods, 25(4):285-297 (1992).
Yin, Q. et al., Cyclic ; di-GMP sensing via the innate immune signaling protein STING, Molecular Cell, 46(6):735-45 (2012).
Yi, G.H. et al., Single Nucleotide Polymorphisms of Human STING Can Affect Innate Immune Response to Cyclic Dinucleotides, Plos One, 8(10):1-16 (2013).
Zhang, X., et al. Cyclic GMP-AMP Containing Mixed Phosphodiester Linkages Is an Endogenous High-Affinity Ligand for STING, Mol. Cell, 51:226-235 (2013).
Zhang, Z. et al. The helicase DDX41 senses intracellular DNA mediated by the adaptor STING in dendritic cells, Nat. Immunol., 12:959-965 (2011).
Zhang, Z. et al., c-di-GMP Displays a monovalent metal ion-dependent polymorphism, J Am Chem. Soc,, 126(51):16700-16701 (2004).
Zhao, J. et al., Thiophosphate analogs of c-di-GMP: impact on polymorphism, Nucleosides Nucleotides & Nucleic Acids, 28(5):352-378 (2009).
Zhong, B. et al.The adaptor protein MITA links virus-sensing receptors to IRF3 transcription factor activation, Immunity 29, 538-550 (2008).
Zhou et al., MyD88 Intrinsically Regulates CD4 T-Cell Responses, J. Virol., 83(4):1625-1634 (2009).
Zhou et al., MyD88 is critical for the development of innate and adaptive immunity during acute lymphocytic choriomeningitis virus infection, Eur. J. Immunol., 35(3):822-830 (2005).
Zhou, J. et al., Endo-S-c-di-GMP analogues-polymorphism and binding studies with class I riboswitch, Molecules, 17(11):13376-13389 (2012).
Zhou, J. et al., Potent suppression of c-di-GMP synthesis via I-site allosteric inhibition of diguanylate cyclases with 2'-F-c-di-GMP, Bioorganic & Medicinal Chemistry, 21(14):4396-4404 (2013).
Joshi, P.C. et al, Selectivity of montmorillonite catalyzed prebiotic reactions of D, L-nucleotides, Orig. Life Evol. Biosph., 37(1): 3-26 (2007).
Simm, R. et al, Phenotypic convergence mediated by GGDEF-domain-containing proteins, J. Bacteriol., 187(19): 6816-23 (2005) and Erratum, 1 page (2006).
Amiot, N. et al, New Approach for the Synthesis of c-di-GMP and Its Analogues, Synthesis, 24: 4320-4236 (2006).
Chin, K-H. et al, Novel c-di-GMP recognition modes of the mouse innate immune adaptor protein STING, Acta. Crystl., D69: 352-366 (2013).
Curran et al., STING pathway activation stimulates potent immunity against acute myeloid leukemia, Cell Rep., 15(11):2357-2366 (2016).
Drenth, J., Principles of Protein X-Ray Crystallography, 2nd Edition, Springer-Verlag New York Inc., Chapter 1, p. 19, 4th pargraph, lines 1-2 (1999).
Klyushnichenko, V., Protein crystallization: From HTS to kilogram-scale, Current Opinion in Drug Discovery and Development, 6(6): 848-854 (2003).
Nicolai et al. Mechanisms of MHC-Deficient Tumor Clearance using STING Agonists, Keystone Symposium on Lymphocytes and their Roles in Cancer, Keystone, CO Feb. 12, 2018.
Ouyang, S. et al., Crystal structure of STING CTD complex with c-di-GMP, retrieved from www.ebi.ac.uk, accession No. 4EF4, May 16, 2012.
Ouyang, S. et al, Supplemental Information, Structural Analysis of the STING Adaptor Protein Reveals a Hydrophobic Dimer Interface and Mode of Cyclic di-GMP Binding, Immunity, 36: 1-24 (2012).
Weber, P., Overview of Crystallization Methods, Methods in Enzymology, 276: 13-22 (1997).
Zhang, X. et al, Crystal structure of STING in complex with cGAMP, retrieved from http:www.ebi.ac.uk/pdbe/entry/pdb/4KSY, Database accession No. 4ksy, Protein Data Bank in Europe, released Jun. 12, 2013.

\* cited by examiner

| | BMDM (Digitonin) | | |
|---|---|---|---|
| | cG(2',5')pA(2',5')p | cG(2',5')pA(3',5')p | cG(3',5')pA(3',5')p |
| $EC_{50}$ (µM) | 0.80 | 0.29 | 0.42 |
| 95% CI (µM) | 0.20 - 3.15 | 0.22 - 0.39 | 0.30 - 0.60 |

| | BMDM | | |
|---|---|---|---|
| $EC_{50}$ (µM) | 12.49 | 12.41 | 8.41 |
| 95% CI (µM) | 9.65 - 16.17 | 10.12 - 15.22 | 7.89 - 9.20 |

| | THP-1 | | |
|---|---|---|---|
| $EC_{50}$ (µM) | 1.17 | 3.35 | 5.66 |
| 95% CI (µM) | 1.00 - 1.38 | 2.93 - 3.84 | 4.97 - 6.44 |

SEQUENCE LISTING

```
<160> NUMBER OF SEQ ID NOS: 54

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caaaggtgtg gagcagctgg ccactggcag cgcctatgaa catgtgaaga tt            52

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 2
aatcttcaca tgttcatagg cgctgccagt ggccagctgc tccacacctt tg    52

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctctctttc tctcacactg aagcgtacat tttgaataat cacggg    46

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccgtgatta ttcaaaatgt acgcttcagt gtgagagaaa gagagg    46

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgaaacgca aagatatcgc ggaggcggcc g    31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggccgcctc cgcgatatct ttgcgtttca a    31

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcggccgag acggtggcta aagttgtgga acgc    34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgttccaca actttagcca ccgtctcggc cgcc    34

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcagctgaac actggcagcg cctatgaaca tgtgaagatt    40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aatcttcaca tgttcatagg cgctgccagt gttcagctgc    40

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaaggtgct ggacaaattg gcattgaaag ccaaagatat ctcggaggcg g    51

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgcctccga gatatctttg gctttcaatg ccaatttgtc cagcaccttc t    51

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatcttccgg agcaaaatgc tgcagagcag aatgtttaaa attaatgaaa tacc    54

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtatttcat taattttaaa cattctgctc tgcagcattt tgctccggaa gatt        54

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggacaaattg agattgaaag ccaaagatat ctcggaggcg        40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcctccgag atatctttgg ctttcaatct caatttgtcc        40

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtggagcagc tgaacactgc cgcctactat gaacatgtga ag        42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttcacatgt tcatagtagg cggcagtgtt cagctgctcc ac        42

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggagcagctg aacactgcca gctactatga acatg        35

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
catgttcata gtagctggca gtgttcagct gctcc        35

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 21
gtggagcagc tgaacactcc cagctactat gaacatgt                             38

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 22
acatgttcat agtagctggg agtgttcagc tgctccac                             38

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 23
ggtgtggagc agctgaacac tcccgcctac tatgaacatg tgaagatt                  48

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 24
aatcttcaca tgttcatagt aggcgggagt gttcagctgc tccacacc                  48

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 25
ggagcagctg aacactggcg cctactatga acatgtgaag                           40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 26
cttcacatgt tcatagtagg cgccagtgtt cagctgctcc                           40

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgtgaagatt tctgctccta atgcatttga tgttatgttt aaactgg                    47

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccagtttaaa cataacatca aatgcattag gagcagaaat cttcaca                    47

<210> SEQ ID NO 29
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaaaatgct gcagaaaaga atgtttaaaa ttaatggcat acctttgga acagttgaaa       60 aaa                                                                    63

<210> SEQ ID NO 30
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30 tttttcaac tgttccaaaa ggtatgccat taattttaaa cattcttttc tgcagcattt       60
tgc                                                                    63

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcaagagct ggatgcattc tgtgcctacc atgtga                                36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcacatggta ggcacagaat gcatccagct cttgaa                                    36

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcctctcttt ctctcacact gcaaagtaca ttttgaataa tcac                           44

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgattattc aaaatgtact ttgcagtgtg agagaaagag aggc                           44

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcattctgtt cctaccatgt ggcaactgcc atctttcaca tgtg                           44

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacatgtgaa agatggcagt tgccacatgg taggaacaga atgc                           44

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcaaggagag acctgggccc tctctttctc tcac                                      34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgagagaaa gagagggccc aggtctctcc ttga                     34

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctggatgca ttctgttccg cccatgtgaa aactgccatc                40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatggcagtt ttcacatggg cggaacagaa tgcatccagc                40

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atatatctcg agatggaaga tccgcgtaga agga                      34

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atatatagat ctctatcaaa gcttgtcaaa aattggaaac ccat            44

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tacagatcta ctagtgatct atgactgatc tgtacatgat ctaca           45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgtagatcat gtacagatca gtcatagatc actagtagat ctgta           45

<210> SEQ ID NO 45
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uacagaucua cuagugaucu augacugauc uguacaugau cuaca                45

<210> SEQ ID NO 46
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uguagaucau guacagauca gucauagauc acuaguagau cugua                45

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaattgccga agacgaa                                               17

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttcgtcttc ggcaatt                                               17

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
acacacacac acacacacac acacacacac acacac                          36

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctctctctct ctctctctct ctctctctct ctctct                          36

-continued

<210> SEQ ID NO 51
<211> LENGTH: 4
<212> TYPE: PRT
<213> ORGANISM: Unknown
<220> FEATURE:
<223> OTHER INFORMATION: Description of Unknown:
      'DEAD' box motif peptide

<400> SEQUENCE: 51

Asp Glu Ala Asp
1

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5

<210> SEQ ID NO 53
<211> LENGTH: 361
<212> TYPE: PRT
<213> ORGANISM: Mus sp.

<400> SEQUENCE: 53

Pro Asp Lys Leu Lys Lys Val Leu Asp Lys Leu Arg Leu Lys Arg Lys
1               5                   10                  15

Asp Ile Ser Glu Ala Ala Glu Thr Val Asn Lys Val Val Glu Arg Leu
                20                  25                  30

Leu Arg Arg Met Gln Lys Arg Glu Ser Glu Phe Lys Gly Val Glu Gln
            35                  40                  45

Leu Asn Thr Gly Ser Tyr Tyr Glu His Val Lys Ile Ser Ala Pro Asn
        50                  55                  60

Glu Phe Asp Val Met Phe Lys Leu Glu Val Pro Arg Ile Glu Leu Gln
65                  70                  75                  80

Glu Tyr Tyr Glu Thr Gly Ala Phe Tyr Leu Val Lys Phe Lys Arg Ile
                85                  90                  95

Pro Arg Gly Asn Pro Leu Ser His Phe Leu Glu Gly Glu Val Leu Ser
                100                 105                 110

Ala Thr Lys Met Leu Ser Lys Phe Arg Lys Ile Ile Lys Glu Glu Val
            115                 120                 125

Lys Glu Ile Lys Asp Ile Asp Val Ser Val Glu Lys Glu Lys Pro Gly
        130                 135                 140

Ser Pro Ala Val Thr Leu Leu Ile Arg Asn Pro Glu Glu Ile Ser Val
145                 150                 155                 160

Asp Ile Ile Leu Ala Leu Glu Ser Lys Gly Ser Trp Pro Ile Ser Thr
                165                 170                 175

Lys Glu Gly Leu Pro Ile Gln Gly Trp Leu Gly Thr Lys Val Arg Thr
                180                 185                 190

Asn Leu Arg Arg Glu Pro Phe Tyr Leu Val Pro Lys Asn Ala Lys Asp
            195                 200                 205

Gly Asn Ser Phe Gln Gly Glu Thr Trp Arg Leu Ser Phe Ser His Thr
        210                 215                 220

Glu Lys Tyr Ile Leu Asn Asn His Gly Ile Glu Lys Thr Cys Cys Glu

```
                225                 230                 235                 240

Ser Ser Gly Ala Lys Cys Cys Arg Lys Glu Cys Leu Lys Leu Met Lys
            245                 250                 255

Tyr Leu Leu Glu Gln Leu Lys Lys Glu Phe Gln Glu Leu Asp Ala Phe
            260                 265                 270

Cys Ser Tyr His Val Lys Thr Ala Ile Phe His Met Trp Thr Gln Asp
            275                 280                 285

Pro Gln Asp Ser Gln Trp Asp Pro Arg Asn Leu Ser Ser Cys Phe Asp
            290                 295                 300

Lys Leu Leu Ala Phe Phe Leu Glu Cys Leu Arg Thr Glu Lys Leu Asp
305                 310                 315                 320

His Tyr Phe Ile Pro Lys Phe Asn Leu Phe Ser Gln Glu Leu Ile Asp
            325                 330                 335

Arg Lys Ser Lys Glu Phe Leu Ser Lys Lys Ile Glu Tyr Glu Arg Asn
            340                 345                 350

Asn Gly Phe Pro Ile Phe Asp Lys Leu
            355                 360

<210> SEQ ID NO 54
<211> LENGTH: 361
<212> TYPE: PRT
<213> ORGANISM: Homo sapiens

<400> SEQUENCE: 54

Ala Ser Lys Leu Arg Ala Val Leu Glu Lys Leu Lys Leu Ser Arg Asp
1               5                   10                  15

Asp Ile Ser Thr Ala Ala Gly Met Val Lys Gly Val Val Asp His Leu
            20                  25                  30

Leu Leu Arg Leu Lys Cys Asp Ser Ala Phe Arg Gly Val Gly Leu Leu
        35                  40                  45

Asn Thr Gly Ser Tyr Tyr Glu His Val Lys Ile Ser Ala Pro Asn Glu
    50                  55                  60

Phe Asp Val Met Phe Lys Leu Glu Val Pro Arg Ile Gln Leu Glu Glu
65                  70                  75                  80

Tyr Ser Asn Thr Arg Ala Tyr Tyr Phe Val Lys Phe Lys Arg Asn Pro
                85                  90                  95

Lys Glu Asn Pro Leu Ser Gln Phe Leu Glu Gly Glu Ile Leu Ser Ala
            100                 105                 110

Ser Lys Met Leu Ser Lys Phe Arg Lys Ile Ile Lys Glu Glu Ile Asn
        115                 120                 125

Asp Ile Lys Asp Thr Asp Val Ile Met Lys Arg Lys Arg Gly Gly Ser
    130                 135                 140

Pro Ala Val Thr Leu Leu Ile Ser Glu Lys Ile Ser Val Asp Ile Thr
145                 150                 155                 160

Leu Ala Leu Glu Ser Lys Ser Ser Trp Pro Ala Ser Thr Gln Glu Gly
                165                 170                 175

Leu Arg Ile Gln Asn Trp Leu Ser Ala Lys Val Arg Lys Gln Leu Arg
            180                 185                 190

Leu Lys Pro Phe Tyr Leu Val Pro Lys His Ala Lys Glu Gly Asn Gly
        195                 200                 205

Phe Gln Glu Glu Thr Trp Arg Leu Ser Phe Ser His Ile Glu Lys Glu
    210                 215                 220

Ile Leu Asn Asn His Gly Lys Ser Lys Thr Cys Cys Glu Asn Lys Glu
225                 230                 235                 240
```

| | | | | | | | | | | | | | |
|---|---|---|---|---|---|---|---|---|---|---|---|---|---|
| Glu | Lys | Cys | Cys 245 | Arg | Lys | Asp | Cys | Leu 250 | Lys | Leu | Met | Lys | Tyr 255 | Leu | Leu |
| Glu | Gln | Leu | Lys 260 | Glu | Arg | Phe | Lys | Asp 265 | Lys | Lys | His | Leu | Asp 270 | Lys | Phe |
| Ser | Ser | Tyr | His 275 | Val | Lys | Thr | Ala | Phe 280 | Phe | His | Val | Cys | Thr 285 | Gln | Asn |
| Pro | Gln 290 | Asp | Ser | Gln | Trp | Asp 295 | Arg | Lys | Asp | Leu | Gly 300 | Leu | Cys | Phe | Asp |
| Asn | Cys 305 | Val | Thr | Tyr | Phe 310 | Leu | Gln | Cys | Leu | Arg 315 | Thr | Glu | Lys | Leu | Glu 320 |
| Asn | Tyr | Phe | Ile | Pro 325 | Glu | Phe | Asn | Leu | Phe 330 | Ser | Ser | Asn | Leu | Ile 335 | Asp |
| Lys | Arg | Ser | Lys 340 | Glu | Phe | Leu | Thr | Lys 345 | Gln | Ile | Glu | Tyr | Glu 350 | Arg | Asn |
| Asn | Glu | Phe | Pro 355 | Val | Phe | Asp | Glu 360 | Phe | | | | | | | |

COMPOSITIONS AND METHODS FOR ALTERING SECOND MESSENGER SIGNALING

CROSS REFERENCE TO RELATED APPLICATIONS

The present application is a divisional of U.S. application Ser. No. 14/787,611, filed on Oct. 28, 2015, which is a U.S. National Phase application under 35 U.S.C. § 371 of International Patent Application No. PCT/US2014/035909, filed on Apr. 29, 2014, which claims priority to U.S. provisional patent application Nos. 61/817,269, filed Apr. 29, 2013, and 61/819,369, filed May 3, 2013, the entire contents of each of which are hereby incorporated by reference herein.

REFERENCE TO SEQUENCE LISTING

The specification includes a Sequence Listing in the form of an ASCII compliant text file named "Sequence_Listing.txt", which was created on Nov. 1, 2016 and has a size of 18.2 kilobytes. The entire contents of the Sequence Listing are herein incorporated by reference.

BACKGROUND OF THE INVENTION

The importance of cyclic dinucleotides as bacterial second messengers is well established, with cyclic di-GMP (c-di-GMP) now acknowledged as a universal bacterial second messenger. This versatile molecule has been shown to play key roles in cell cycle and differentiation, motility and virulence, as well as in the regulation of biofilm formation and dispersion. Advances in our understanding of c-di-GMP has emerged with the identification, structural characterization, and mechanistic understanding of the catalytic activities of the bacterial enzymes responsible for the synthesis and degradation of this second messenger. Crystal structures of c-di-GMP in the free state and when bound to enzymes responsible for its synthesis and degradation have shown that this second messenger can adopt either monomeric or a dimeric bis-intercalated folds. It appears that formation of c-(3',5')-di-GMP from two molecules of GTP occurs via a two-step reaction and formation of 3',5'-phosphodiester linkages, with two molecules of pyrophosphate as byproducts of the cyclization reaction. Moreover, multiple receptors targeted by c-(3',5')-di-GMP and the diverse ways bacteria signal through this second messenger have been identified. Indeed, the field of c-di-GMP study as a second messenger has grown immensely and yielded major advances in our understanding of the physiology and mechanisms of bacterial cyclic dinucleotide signaling over the last two and a half decades. In parallel studies, c-(3',5')-di-GMP-specific riboswitches have also been identified, including ones that are involved in cyclic dinucleotide-induced RNA splicing.

There is much interest currently towards gaining a molecular and functional understanding of innate immunity sensors of higher metazoans that recognize nucleic acids in the cytoplasm and trigger type I interferon induction. Cytoplasmic dsDNA of pathogenic bacterial or viral origin, and perhaps also displaced nuclear or mitochondrial DNA following cellular stress, represent such a trigger. These events involving self-nucleic acid recognition in turn could trigger autoimmune diseases such as systemic lupus erythematosus and Sjögren syndrome. Indeed, in recent years many cytoplasmic DNA sensors have been identified, including DAI (DNA-dependent activator of IFN-regulatory factor), LRRFIP1 (leucine-rich repeat and flightless I interacting protein 1), DDX41 (DEAD box polypeptide 41) ("DEAD" disclosed as SEQ ID NO: 51), and members of the HIN-200 (hematopoietic interferon-inducible nuclear proteins) family such as AIM2 (absent in melanoma 2) and IFI16 (interferon-inducible protein 16). Molecular information is available on the HIN domain family as reflected in structures of their complexes with dsDNA. A requirement for multiple sensors may be a reflection of distinctive cell-type specific activities. Cytoplasmic detection of dsDNA activates stimulator of interferon genes (STING) in the cytoplasm, which in turn initiates a cascade of events by first activating kinases IKK (IκB kinase) and TBK1 (TANK-binding kinase 1), leading to phosphorylation and activation of the transcription factors NF-κB (nuclear factor κB) and IRF3 (interferon regulatory factor). These phosphorylated transcription factors translocate to the nucleus to target immune and inflammatory genes leading to the production of cytokines and type I interferons, thereby triggering the host immune response. Therefore, there is a need for therapeutic agents to modulate the induction of interferon and other relevant components in these pathways.

SUMMARY OF THE INVENTION

The present invention provides, among other things, novel cyclic-GMP-AMP (cGAMP) analogs, mimics, mimetics and variants as described in more detail below. These cGAMP compounds and compositions are, among other things, useful in the design of research tools, as a research tool, and as therapeutic modalities such as enzyme modulators including agonists and antagonists of cGAS. The present invention also provides crystallographic data for cyclic-GMP-AMP synthase (cGAS). These crystallographic data provide the basis for which to design modulators (agonists and antagonists) such as cGAMP compounds or small molecules, which are useful in the fields of research, therapeutics and/or diagnostics.

DETAILED DESCRIPTION OF CERTAIN EMBODIMENTS

Figure 1:
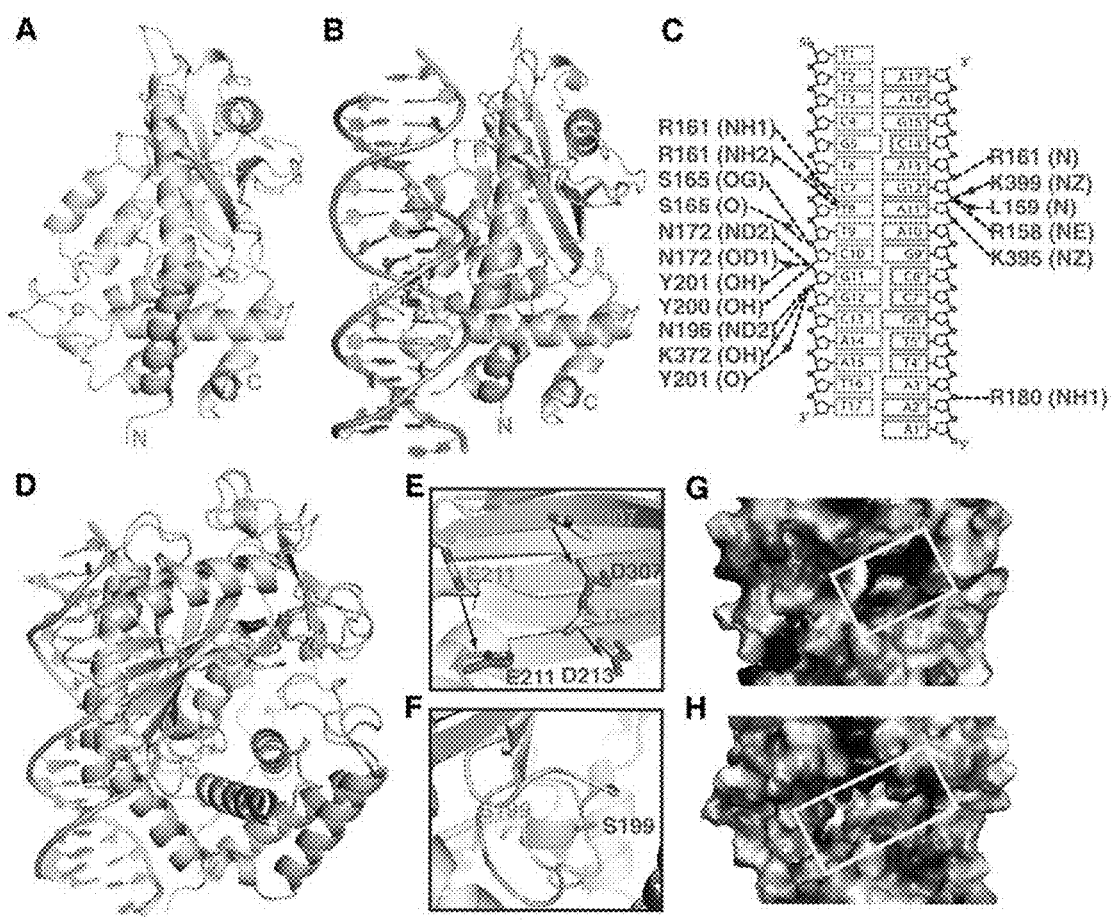
FIG. 1, comprising panels A-H, shows Structures of cGAMP Synthase (cGAS) in the Free State and Bound to dsDNA. (A) 2.0 Å crystal structure of cGAS in the free state. The backbone of the protein in a ribbon representation is colored in light gray. (B) 2.1 Å crystal structure of cGAS bound to a complementary 16-bp DNA duplex (with one base 5'-overhang at each end). The protein and DNA are colored in dark gray in the binary complex. (C) A schematic of intermolecular hydrogen bonds in the binary cGAS-DNA complex (SEQ ID NOS 48 and 47, respectively, in order of appearance). (D) Superposed structures of cGAS in the free state (light gray) and in the cGAS-DNA complex (dark gray). (E, F) Large changes within the 3-sheet (panel E) and catalytic pocket (panel F) segments on proceeding from cGAS in the free state (light gray) to the binary complex with bound DNA (dark gray). (G) Narrow entrance to the catalytic pocket in the structure of cGAS in the free state, with the protein in an electrostatic representation. (H) Widened entrance to the catalytic pocket in the structure of the binary cGAS-DNA complex.
Figure 2:
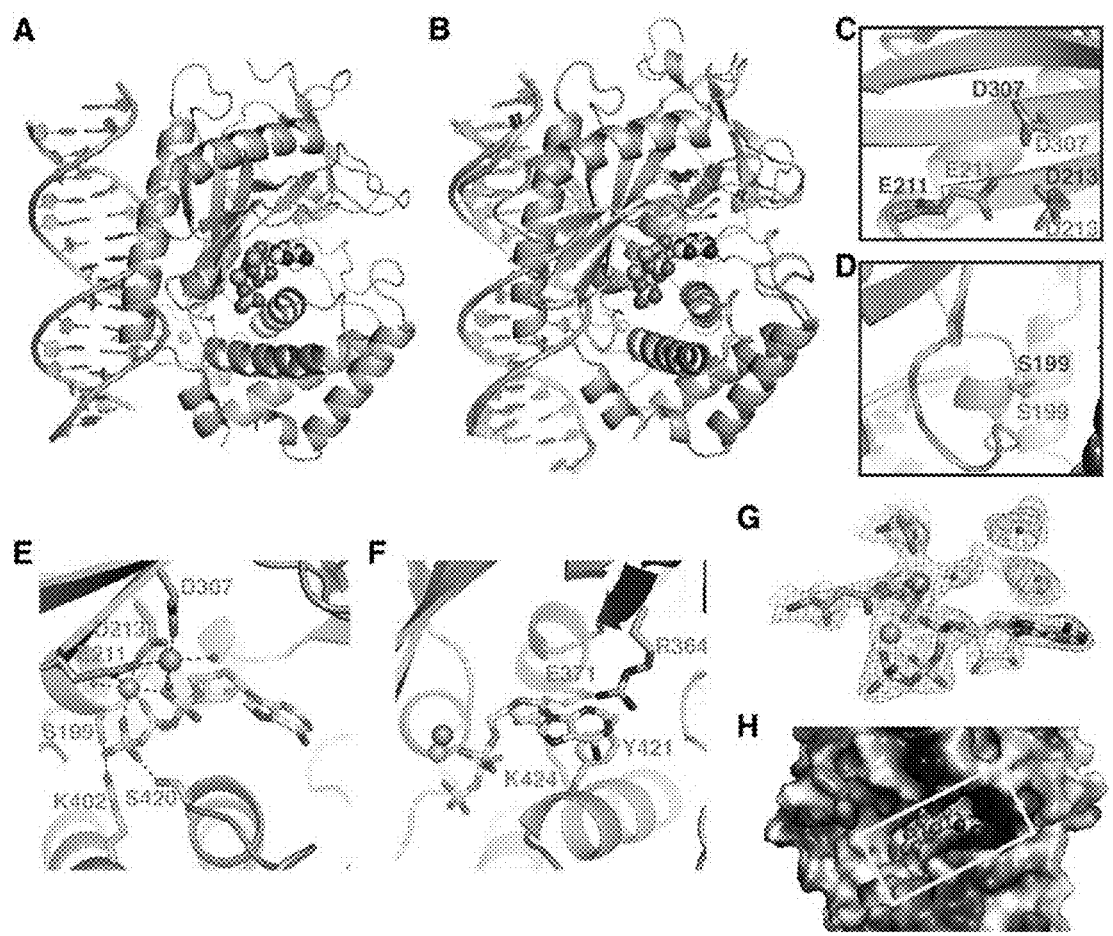
FIG. 2, comprising panels A-H, shows Structures of the ternary complex of cGAS, dsDNA and ATP. (A) 2.4 Å crystal structure of the ternary complex of cGAS bound to dsDNA and ATP. The protein and dsDNA are shown in ribbon, with bound ATP in a space-filling representation. (B) Superposed structures of the binary complex of cGAS and DNA and the ternary complex with added ATP. (C, D) Absence of changes in the backbone within the β-sheet (panel C) and catalytic pocket (panel D) segments on proceeding from the binary cGAS and dsDNA complex to the ternary complex with added ATP. (E, F) Two alternate views of intermolecular contacts between ATP and catalytic pocket residues in the ternary complex. Two cations are shown as spheres, with hydrogen bonds shown by dashed lines. (G) 2Fo-Fc electron density map contoured at 1.2σ (light gray) and Fo-Fc map contoured at 3.0σ (dark gray) of bound ATP, pair of cations and coordinating residues in the catalytic pocket. This map contains some weak unaccounted for electron density (dark gray). (H) View of bound ATP in a space-filling representation within the catalytic pocket, with the protein in an electrostatic representation.
Figure 3:
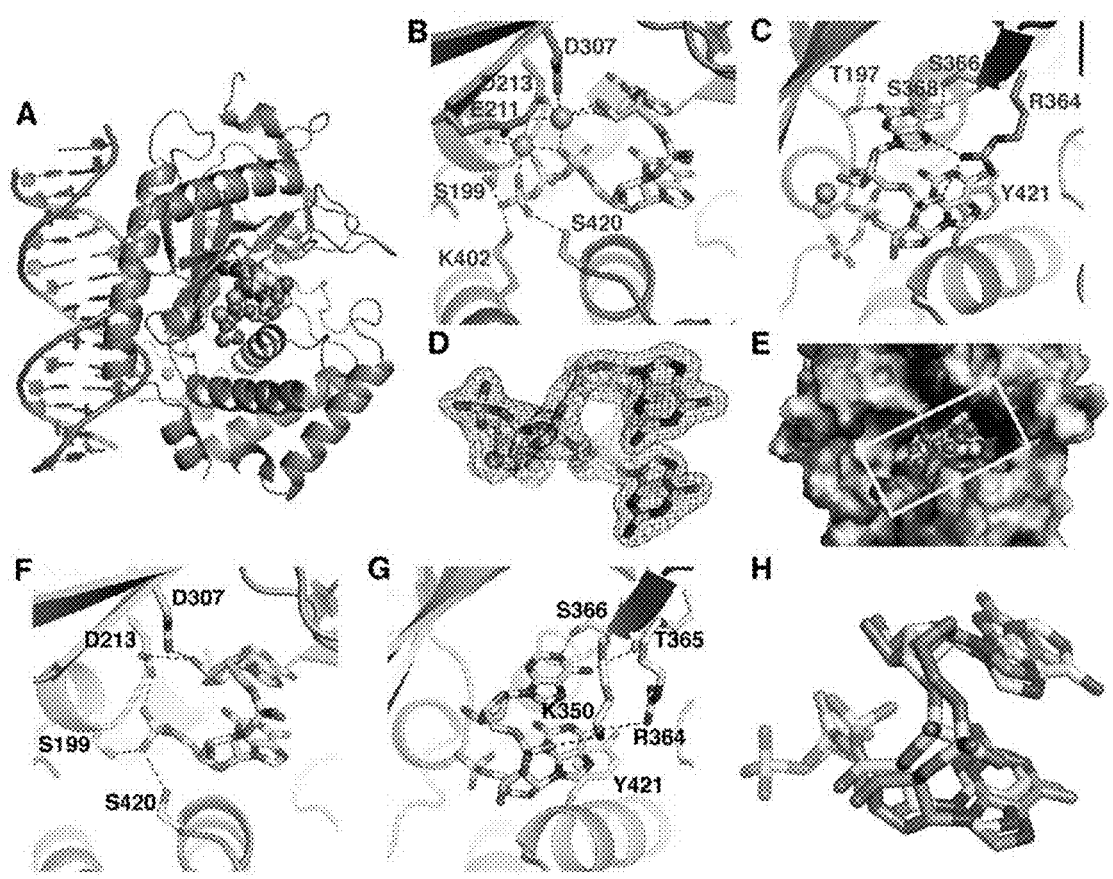
FIG. 3, comprising panels A-H, shows Structures of the Ternary Complex of cGAS, dsDNA with Bound Products 5'-pppG(2',5')pG and 5'-pG(2',5')pA. (A) 1.9 Å crystal structure of the ternary complex of cGAS bound to dsDNA and 5'-pppG(2',5')pG. The protein and DNA are shown in ribbon, with bound 5'-pppG(2',5')pG in a space-filling representation. (B, C) Two alternate views of intermolecular contacts between 5'-pppG(2',5')pG and catalytic pocket residues in the ternary complex. Two cations are shown as spheres, with hydrogen bonds shown by dashed lines. (D) 2Fo-Fc electron density map contoured at 1.2σ of bound 5'-pppG(2',5')pG in the catalytic pocket of the ternary complex. (E) View of bound 5'-pppG(2',5')pG in a space-filling representation within the catalytic pocket, with the protein in an electrostatic representation. (F, G) Two alternate views of intermolecular contacts between 5'-pG(2',5')pA and catalytic pocket residues in the 2.3 Å ternary complex of cGAS, dsDNA and GMP+ATP. (H) Superposition of structures of bound 5'-pppG(2',5')pG (dark gray) and 5'-pG(2',5')pA (light gray).

It has been shown that VSP-1 (Vibrio $7^{th}$ pandemic island-1) genes encode a novel class of dinucleotide cyclases, which preferentially synthesize a cyclic-GMP-AMP (designated cGAMP) molecule, thereby expanding our horizon to cyclic GA-dinucleotides (Davies et al. 2012). More recently, cyclic GMP-AMP synthase (cGAS, official human gene symbol MB21D1) was identified as a cytoplasmic DNA sensor that activated the type I interferon pathway by synthesizing the second messenger cGAMP (Sun et al. 2013; Wu et al. 2013). cGAS was shown to be a member of the nucleotidyltransferase family, and to be capable of generating a cGAMP in vitro from GTP and ATP in the presence of dsDNA (but not dsRNA), while chemically synthesized cGAMP containing a pair of 3',5' linkages was shown to stimulate the production of interferon in THP 1 and Raw264.7 cells at concentrations as low as 10 nM. The authors also demonstrated through experiments involving either overexpression or knockdown of cGAS, that the synthetic cGAMP bound to and activated STING, resulting in the activation of transcription factor IRF3 and subsequent induction of interferon (Sun et al. 2013; Wu et al. 2013).

A critical assumption in these studies on cGAS was that cGAMP contained a pair of 3',5' linkages (Sun et al. 2013; Wu et al. 2013), in line with those reported previously for c-di-GMP in bacterial systems as outlined above. The present invention encompasses the recognition that the previously assigned structure of cGAMP by Sun and Wu was incorrect. Thus, one aspect of the present invention is the identification of the previously unknown problem of mis-identification of the structure of cGAMP. The present disclosure combines structural, chemical, in vitro biochemical and in vivo cellular assays to establish unequivocally that this second messenger unexpectedly contains 2',5' linkage at the GpA step and 3',5' linkage at the ApG step {designated c[G(2',5')pA(3',5')p] }, thus identifying correctly and for the first time, the founding member of a new family of metazoan second messengers regulating type I interferon induction in response to cytoplasmic DNA.

In certain embodiments, the present invention provides compounds comprising cyclic GA-dinucleotides [c[G(2',5')pA(3',5')p]] containing a 2',5' linkage (at the GpA step). In some embodiments, such compounds are useful for the study of cellular signaling and immune surveillance in metazoans. In some embodiments, such compounds are useful in the treatment, diagnosis or prophylaxis of disorders, diseases or conditions in medicine. In some embodiments, such compounds are useful to modulate targets involved in immune response. In some embodiments, the compounds and/or compositions of the invention are useful as research tools and/or reagents, particularly in kits and assays for biological or chemical research.

The present invention also provides crystallographic data useful in the design of modulators of cGAS. In certain embodiments, the invention provides modulators of cGAS that comprises features to form appropriate binding interactions with cGAS. In some embodiments, such modulators comprise features that form appropriate binding interactions with targets that bind to cGAMP.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in some embodiments alkenyl groups contain 2-3 carbon atoms, and in some embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in some embodiments alkynyl groups contain 2-3 carbon atoms, and in some embodiments alkynyl groups contain 2 carbon atoms. Representative alkynyl groups include, but are not limited to, ethynyl, 2-propynyl (propargyl), 1-propynyl, and the like.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below.

The term "halo," as used herein, represents a halogen selected from bromine, chlorine, iodine, or fluorine The term "halogen" means F, Cl, Br, or I.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CCl$_3$, —CH$_2$CH$_2$Br, —CH$_2$CH(CH$_2$CH$_2$Br)CH$_3$, and —CHICH$_3$. In some embodiments, the haloalkyl group can be further substituted with 1, 2, 3, or 4 substituent groups as described herein for alkyl groups.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monoor bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^●$, -(halo$R^●$), —OH, —O$R^●$, —O(halo$R^●$), —CN, —C(O)OH, C(O)O$R^●$, —NH$_2$, —NH$R^●$, —N$R^●_2$, or —NO$_2$, wherein each $R^●$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 3,4-dimethoxybenzylidene acetal, 2-nitrobenzylidene acetal, methoxymethylene acetal, ethoxymethylene acetal, α-methoxybenzylidene ortho ester, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), cyclic carbonates, cyclic boronates, ethyl boronate, and phenyl boronate. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol "⁓", except when used as a bond to depict unknown or mixed stereochemistry, denotes the point of attachment of a chemical moiety to the remainder of a molecule or chemical formula.

As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator or agonist, in that activity is increased in its presence as compared with that observed under otherwise comparable conditions when the modulator is absent. In some embodiments, a modulator is an inhibitor or antagonist, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level. As used herein, an "activity" is any process, carried out by a molecule, compound, cell, tissue or organ. Such processes may be catalytic or non-catalytic. For example, the cGAS molecules of the present invention may act as enzymes and as such may have enzymatic activity.

The term "nucleic acid," in its broadest sense, includes any compound and/or substance that comprise a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleosides).

The modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil.

The modified nucleosides and nucleotides can include a modified nucleobase. Examples of nucleobases found in RNA include, but are not limited to, adenine, guanine, cytosine, and uracil. Examples of nucleobase found in DNA include, but are not limited to, adenine, guanine, cytosine, and thymine.

As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 2 (dinucleotide or dinucleoside), 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

The term "polypeptide", as used herein, generally has its art-recognized meaning of a polymer of at least three amino acids, linked to one another by peptide bonds. In some embodiments, the term is used to refer to specific functional classes of polypeptides, such as, for example, receptors, enzymes, signaling proteins, structural proteins, autoantigen polypeptides, nicotinic acetylcholine receptor polypeptides, alloantigen polypeptides, etc. For each such class, the present specification provides several examples of amino acid sequences of known exemplary polypeptides within the class; in some embodiments, such known polypeptides are reference polypeptides for the class. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer, or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid. In such embodiments, the term "polypeptide" refers to any member of the class that shows significant sequence homology or identity with a relevant reference polypeptide. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide as described herein may comprise or consist of a fragment of a parent polypeptide. In some embodiments, a useful polypeptide as described herein may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to polypeptide sequences means the corresponding sequence of other species having substantial identity to a second sequence of a second species.

"Analogs" in the context of polypeptides is meant to include polypeptide variants which differ by one or more amino acid alterations, e.g., substitutions, additions or deletions of amino acid residues that still maintain one or more of the properties of the parent or starting polypeptide.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

The term "therapeutic agent" or "therapeutic modality" refers to any agent that, when administered to a subject, has a therapeutic, diagnostic, and/or prophylactic effect and/or elicits a desired biological and/or pharmacological effect.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

As used herein, the term "patient" or "subject" refers to a human or any non-human animal (e.g., mouse, rat, rabbit, dog, cat, cattle, swine, sheep, horse or primate) to whom therapy is administered. In many embodiments, a patient is a human being. A human includes pre and post natal forms. In some embodiments, a patient is a human presenting to a medical provider for diagnosis or treatment of a disease, disorder or condition. In some embodiments, a patient displays one or more symptoms or characteristics of a disease, disorder or condition. In some embodiments, a patient does not display any symptom or characteristic of a disease, disorder, or condition. In some embodiments, a patient is someone with one or more features characteristic of susceptibility to or risk of a disease, disorder, or condition.

As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

As used herein "stable" refers to a compound or molecule that is sufficiently robust to survive isolation to a useful degree of purity from a reaction mixture, and preferably capable of formulation into an efficacious therapeutic agent. Alternatively a compound or molecule may be said to be stable if it is sufficiently robust to withstand any treatment, insult or utilization without undergoing substantial degradation prior to a selected timepoint, event or localization.

As used herein, the term "stabilize", "stabilized," "stabilized region" means to make or become stable.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The term "computer-readable medium", as used herein, refers to non-volatile (i.e. secondary storage) computer data storage and/or memory to retain digital data even when not powered. Examples of computer-readable medium include, but are not limited to hard disk, floppy disk, flash memory (i.e. solid state memory), Ferroelectric RAM (F-RAM), Magnetoresistive RAM (MRAM), optical disc, standalone RAM disks, ZIP drives, magenetic tape and holographic memory.

Figure 18:
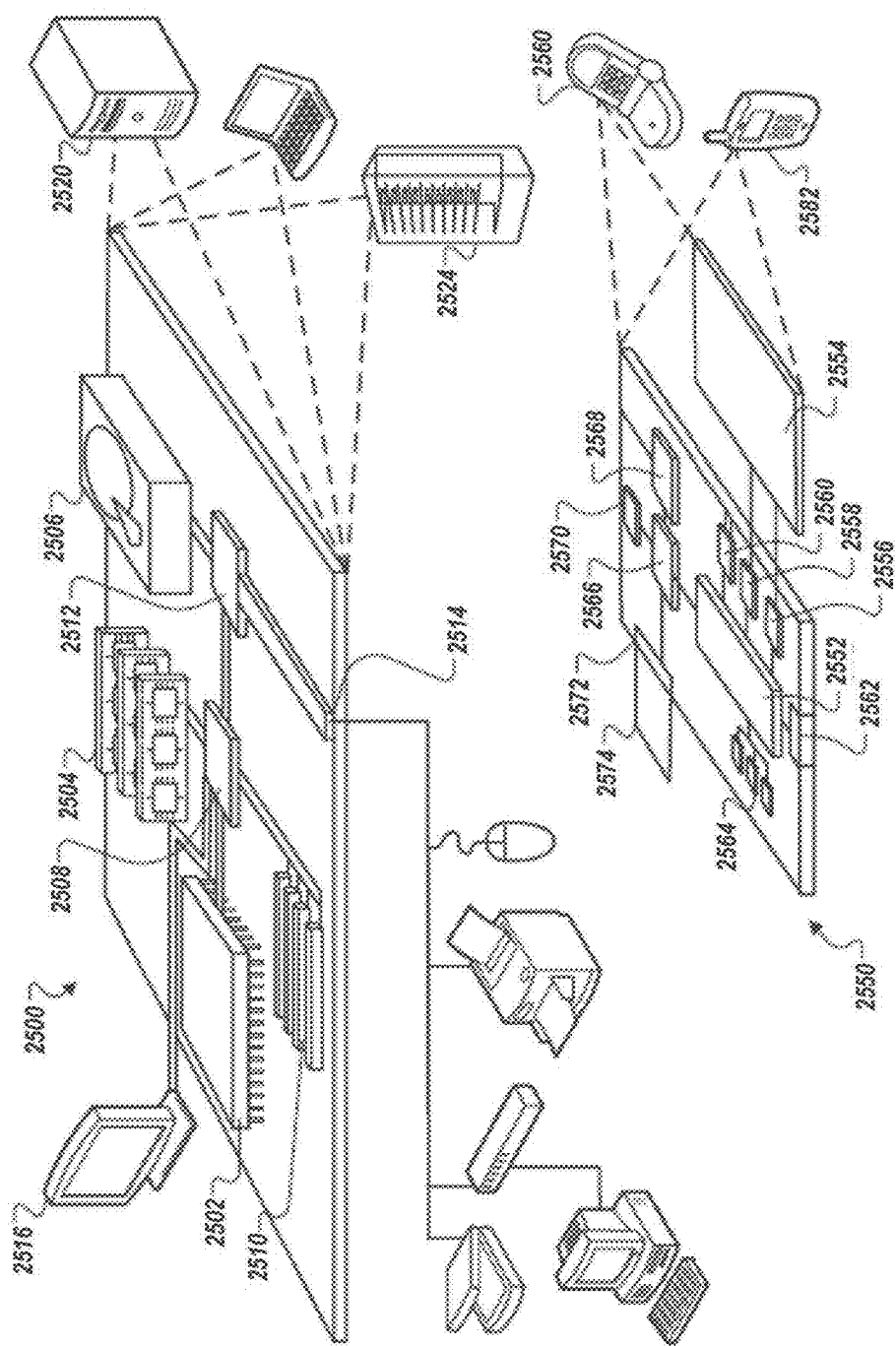
FIG. 18 is an exemplary block diagram of a network environment for establishing a multi-channel context aware communication environment.

The term "computer system" or "computer", as used herein, refers to a computing device that can be used to implement the techniques described in this disclosure. An exemplary computing device 2500 and a mobile computing device are shown in FIG. 18.

As used herein, the term "crystal structure" of a composition shall mean a computer readable medium in which is stored a representation of three dimensional positional information (i.e. coordinates) for atoms of the composition.

As used herein, the term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et al. J. Comp. Chem. 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., J. Mol. Recognition 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., J. Med. Chem. 33:889-894 (1990)). Docking can also be performed by combining a Monte Carlo search technique with rapid energy evaluation using molecular affinity potentials. See Goodsell and Olson, Proteins: Structure, Function and Genetics 8:195-202 (1990). Software programs that carry out docking functions include but are not limited to MATCHMOL (Cory et al., J. Mol. Graphics 2: 39 (1984); MOLFIT (Redington, Comput. Chem. 16: 217 (1992)) and DOCK (Meng et al., supra).

As used herein, the term "designed" refers to an agent (i) whose structure is or was selected by the hand of man; (ii) that is produced by a process requiring the hand of man; and/or (iii) that is distinct from natural substances and other known agents.

As used herein, the term "storage environment" comprises any environment comprising secondary storage, i.e. long-term persistent storage. In some embodiments, a storage environment comprises computer-readable medium. In some embodiments, a storage environment comprises a network environment for establishing a multi-channel context aware communication environment (i.e. cloud computing). For example, FIG. 18 is a block diagram of a network environment for establishing a multi-channel context aware communication environment.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Compounds and Compositions of the Invention

It has surprisingly been discovered, contrary to the disclosures in the art, that the founding member of a family of metazoan cyclic dinucleotide second messengers regulating type I interferon induction in response to cytoplasmic DNA comprises unique features heretofor not known. These insights now afford the opportunity to design analogs, mimics, and/or mimetics of the molecule identified and to further use the parent molecule or molecules designed based on the structure of the parent molecules in research and development.

cGAMP Analogs, Mimics, Mimetics and Modifications

The family of second messengers, termed cGAMPs or cyclic GAMPs, includes one or more of the cyclic structures defined as having at least one guanine (G) and one adenine (A) nucleotide and being linked in a cyclic fashion. The linkages between the two nucleotides involve sugar to backbone bond formation. According to the present invention, there are four primary parent members of the cGAMP family. These include [c[G(2',5')pA(3',5')p]], [c[G(2',5')pA(2',5')p]], [c[G(3',5')pA(2',5')p]], [c[G(3',5')pA(3',5')p]]. Furthermore, each of the nucleotides of the pairs may adopt either syn or anti glycosidic torsion orientations.

As used herein, the term "cGAMP" refers to any of the parent molecules of the family as well as any of the possible torsion orientations. Individual members of the family may be referred to by their sugar-backbone linkage form, e.g., the newly discovered second messenger, [c[G(2',5')pA(3',5')p]], may be referred to as the "2-prime-3'prime" isomer, referencing the position on the sugar ring forming the sugar-backbone bond. The other isomers may be named likewise. Collectively, the compounds of the invention which are wild type, analogs, mimics, mimetics or modified versions of the cGAMP family, are referred to as the group of "cGMP compounds."

With the teachings provided herein, one of skill may now design analogs, mimics, or modifications to any of the parent molecules for use as a modulator, either agonist or antagonist, of the cGAS enzyme, and ultimately as a modulator of downstream physiologic events associated with interferon signaling. Linear versions may also be designed as either agonists, antagonists, or competitive inhibitors of cGAS or downstream signaling events associated with either cGAS enzyme activity or interferon signaling.

The present invention contemplates several types of compounds or compositions which are nucleic acid based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As used herein, an "analog" is meant to include cGAMP variants which differ by one or more alterations, e.g., substitutions, additions or deletions that still maintain one or more of the properties of the parent or starting molecule. Analogs are typically designed using structure-activity relationships (SAR) such as those described herein.

cGAS Proteins, Variants, Derivatives and Mutants

Having now in hand several protein crystal structures in native and varying binding states, it is possible to exploit these protein structures by designing variants, derivatives or mutants of the cGAS enzyme. As such, cGAS enzyme polypeptides, including their variants, derivatives and mutants are considered compounds of the invention. These variants, derivatives and mutants are useful as research tools, for example in kits or assays or as the source of a therapeutic modality. To this end, fragments or portions of the cGAS polypeptide or the variants, derivatives and mutants may be used as antigens for the production of antibodies, or where the fragment maintains a structural element associated with activity, whether binding, catalysis, or transport may also be used as a modulator of the enzyme itself or as a surrogate for dsDNA binding. Collectively, the compounds of the invention which are wild type, variants, derivatives or mutants of cGAS, are referred to as the group of "cGAS molecules." cGAS molecules may comprise any portion or fragment of a cGAS molecule or may comprise mixed domains or fragments from cGAS molecules arising from different structures as defined by the crystal structures disclosed herein.

The present invention contemplates several types of compositions which are polypeptide based including variants and derivatives. These include substitutional, insertional, deletion and covalent variants and derivatives. The term "derivative" is used synonymously with the term "variant"

but generally refers to a molecule that has been modified and/or changed in any way relative to a reference molecule or starting molecule.

As such, cGAS encoding polypeptides containing substitutions, insertions, and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)) the contents of which are incorporated by reference it its entirety.

"Features" when referring to polypeptides are defined as distinct amino acid sequence-based components of a molecule. Features of the cGAS polypeptides encoded by the present invention include surface manifestations, local conformational shape, folds, loops, half-loops, domains, half-domains, sites, termini or any combination thereof.

As used herein when referring to polypeptides the term "surface manifestation" refers to a polypeptide based component of a protein appearing on an outermost surface.

As used herein when referring to polypeptides the term "local conformational shape" means a polypeptide based structural manifestation of a protein which is located within a definable space of the protein.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (J. Mol Biol 266 (4): 814-830; 1997). Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the term "half-domain" means a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

As recognized by those skilled in the art, protein fragments, functional protein domains, and homologous proteins are also considered to be within the scope of polypeptides of interest of this invention. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a polypeptide to be utilized in accordance with the invention includes 2, 3, 4, 5, 6, 7, 8, 9, 10, or more mutations as shown in any of the sequences provided or referenced herein.

Antibodies

In some embodiments, the cGAMP compounds or cGAS molecules may be used to generate antibodies. As such, the antibodies so generated are considered further compounds and compositions of the present invention. As used herein, term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be generated by the compounds or molecules of the invention, including the heavy chains designated alpha, delta, epsilon, gamma and mu, respectively.

While not wishing to be bound by theory, it is believed that antibodies generated using the cGAMP compounds or cGAS molecules disclosed herein will result in improved therapeutic efficacy.

Antibodies of the invention may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, inflammation, respiratory, sensory and anti-infective.

In one embodiment, variants of antibodies may also include, but are not limited to, substitutional variants, conservative amino acid substitution, insertional variants, deletional variants and/or covalent derivatives.

Vaccines

As used herein, a "vaccine" is a biological preparation that improves immunity to a particular disease or infectious agent. According to the present invention and while not wishing to be bound by theory, it is believed that utilization of the cGAMP compounds or cGAS molecules of the invention may be used as a vaccine or as vaccine adjuvant.

Vaccines of the invention may be utilized to treat conditions or diseases in many therapeutic areas such as, but not limited to, cardiovascular, CNS, dermatology, endocrinology, oncology, immunology and autoimmunity, inflammation, respiratory, and anti-infective.

ALB Compounds

In some embodiments, the present invention provides a modulator of a polypeptide that binds cGAMP having a structure comprising the following features:

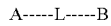

wherein:
A is or comprises a moiety that fits in the cGAS adenosine binding site;
B is or comprises a moiety that fits in the cGAS guanosine binding site; and
optionally, L is a linker moiety linking A and B in a manner which allows A and B to adopt appropriate interactions to bind cGAS.

In some embodiments, the polypeptide that binds cGAMP is cGAS. In some embodiments, the polypeptide that binds cGAMP is STING.

In some embodiments, A is Ring A as defined below and described in classes and subclasses herein, both singly and in combination. In some embodiments, A optionally makes one or more interactions with cGAS at one or more sites selected from the group consisting of Ser199, Ser420, Lys402, Glu211, Asp213, Asp307, Tyr421, Arg364, and combinations thereof. In some embodiments, A optionally makes one or more interactions with cGAS at one or more sites selected from the group consisting of Tyr421, Asp213, Asp307, Arg364, and combinations thereof.

In some embodiments, B is Ring B as defined below and described in classes and subclasses herein, both singly and in combination. In some embodiments, B optionally makes one or more interactions with cGAS at one or more sites selected from the group consisting of Tyr421, Thr197, Ser366, Ser368, Arg364, and combinations thereof.

In some embodiments, a linker moiety is a linker suitable to covalently link A and B and which allows A and B to adopt appropriate interactions to bind cGAS. In some embodiments, a linker together with A and/or B comprises a nucleoside optionally containing one or more phosphate groups. In some embodiments, a linker together with A and B comprises a cyclic dinucleoside optionally containing one or more phosphate groups. In some embodiments, a modulator is a cyclic-GMP-AMP analog.

In some embodiments, a linker moiety comprises one or more ribose or phosphate groups. In some embodiments, such ribose and phosphate groups, along with Ring A or B, form a ribonucleotide. In some embodiments, a modulator comprises one or more modified ribonucleotides. Modified ribonucleotides are well known in the art, and include modifications to a phosphate group, ribose group, nucleotide base group, and combinations thereof. The present invention contemplates all possible modified ribonucleotides for modulators and compound described herein. In some embodiments, these modifications enhance compound stability in vivo. In some embodiments, modifications increase compound resilience to phosphodiesterases.

In some embodiments, a linker comprises a modified phosphodiester group. Such modifications are known in the art and include, without limitation, substituting phosphodiesters with phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, boranophosphates, and combinations thereof. In some embodiments, a phosphodiester is modified to a phosphoramidates. Suitable phosphoramidates include, without limitation, those listed available at www.glenresearch.com/Reference/StructureListing.php, the entire contents of which are hereby incorporated by reference.

In some embodiments, a linker does not include phosphorus. In some embodiments, a linker comprises a short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane moieties; sulfide, sulfoxide and sulfone moieties; amides, carboxylates, formacetyl and thioformacetyl moieties; methylene formacetyl and thioformacetyl moieties; riboacetyl moieties; alkene containing moieties; sulfamate moieties; methyleneimino and methylenehydrazino moieties; sulfonate and sulfonamide moieties; amide moieties; and others having mixed N, O, S, and CH$_2$ component parts.

In addition, a phosphodiester linker may be modified to improve the stability of the compound. For example, in certain instances the P=O linkage is changed to a P=S linkage which is not as susceptible to degradation by nucleases in vivo. In certain instances, the C-2 hydroxyl group of the sugar moiety of a nucleotide is converted to an alkyl or heteroalkyl ether. This modification renders the oligonucleotide less prone to nucleolytic degradation.

Additional phosphodiester modification are described by Dellinger et al. Curr Protoc Nucleic Acid Chem. 2004 October; Chapter 4:Unit 4; Marshall et al. Science. 1993 Mar. 12; 259(5101):1564-70, the entire contents of which are hereby incorporated by reference.

A linker moiety may also comprise one or more modified ribose moieties. In some embodiments, a linker comprises a ribose modified at one of the following at the 2' or 3' position: OH; F; O—, S—, or N-alkyl; O—, S—, or N-alkenyl; (O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In some embodiments, 2' or 3' modifications include: 2'-O-Me, 2'-O-MOE, 2'-O-allyl, 2'-O-dinitrophosphate, 2'-fluoro, 2'-thio, 2'-aminoethyl, 2'-guanidinopropyl. In some embodiments, 2' or 3' modifications include: $O[(CH_2)_nO]_mCH_3$, $O(CH_2)_nOCH_3$, $O(CH)_nNH_2$, $O(CH_2)_nCH_3$, $O(CH)_nONH_2$, and $O(CH)_nON[(CH)CH_3]_2$, where n and m are from 1 to about 10. In some embodiments, a linker comprises a ribose modified at the 2' or 3' position with: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyakylamino, substituted silyl, an RNA-cleaving group, a reporter group, an intercalator, a group for improving the pharmacokinetic properties of an oligonucleotide, or a group for improving the pharmacodynamic properties of an oligonucleotide, and other substituents having similar properties. In some embodiments, a modification includes 2'-O-methoxyethyl (2'-O—$CH_2CH_2OCH_3$, also known as 2'-O-(2-methoxyethyl) or 2'-methoxyethoxy or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$. Other modifications to a linker ribose include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In some embodiments, a 2'-arabino modification is 2'-F.

Similar modifications may also be made at other positions on the oligonucleotide, particularly the 3' position of the sugar on the 3' terminal nucleotide and the 5' position. Oligonucleotides may also have sugar mimetics such as cyclobutyl moieties in place of the pentofuranosyl sugar.

In some embodiments, a linker ribose is modified to a Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—) n group bridging the 2' oxygen atom and the 4' carbon atom wherein n is 1 or 2. LNAs and preparation thereof are described in International Patent Publication Nos. WO 98/39352 and WO 99/14226, the entire contents of which are hereby incorporated by reference. In some embodiments, the LNA forms a moiety:

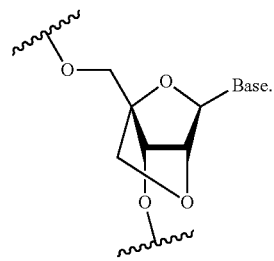

In certain embodiments, a linker comprises a hexose moiety. In some embodiments, the hexose is glucose or mannose. In certain instances, the ribose sugar moiety is replaced with a cyclohexenyl group or polycyclic heteroalkyl ring. In some embodiments, the ribose sugar moiety is replaced with morpholino group. Additional ribose modification are discussed by Engels, New Biotechnology, Vol. 30, 3, p. 302 (2013), the entire contents of which are hereby incorporated by reference.

In some embodiments A or B is an unmodified or natural nucleobase selected from adenine (A) and guanine (G), and the pyrimidine bases thymine (T), cytosine (C) and uracil (U). In some embodiments, A or B is a modified nucleobase. Modified nucleobases are known in the art and include, without limitation, synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. In some embodiments, a non-natural nucleobase is difluorotolyl, nitropyrrolyl, or nitroimidazolyl. In certain embodiments, a non-natural nucleobase is 7-deazaadenine, 3-deazaadenine, N1-methyl-guanosine, 6-thioguanosine, 2-pyrimidinone, 4-thiouridine, 2-pyridinone, 5-propynyl-uridine, imidazole- 4-carboxamide, 5-nitroindol, 3-nitropyrrole, 2-aminopurine, 5-methyl-2-pyrimidinone, N3-thioethylthymidine, 6-thiopurine, 5-iodouridine, 8-azidoadenosine, 5-mercaptouridine, or those derived from 5-bromouracil, diaminopurine, 2-thiouracil, 4-thiouracil, pseudouracil, difluorotoluene, and dihydrourauril. Additional modified nucleobases include those found in www.glenresearch.com/Reference/Structure-Listing.php and www.thermoscientificbio.com/rna-pricing-and-modifications/, the entire contents of each of which are hereby incorporated by reference. Additional modifications are discussed by Verma et al. Annu. Rev. Biochem. 1998. 67:99-134.

In some embodiments, a linker moiety comprises a group that replaces both a phosphodiester and ribose groups of a ribonucleotide. One such linker is referred to as a peptide nucleic acid (PNA). In PNA compounds, the usual sugar-backbone of an oligonucleotide is replaced with an amide containing backbone, for example an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500; Nielsen et al., Chem. Soc. Rev., 1997,26, 73-78: Shakeel et al., Journal of Chemical Technology & Biotechnology, Volume 81, Number 6, June 2006, pp. 892-899(8); Nielsen, CHEMISTRY & BIODIVERSITY—Vol. 7 (2010), p. 786.

These and other suitable linkers are discussed in U.S. Pat. Nos. 7,365,058, 8,101,348, 8,088,902, 7,579,451, 7,582,744, 8,334,373, 8,017,762, 7,919,612, 7,812,149, and 7,723,508, the entire contents of each of which are hereby incorporated by reference herein.

In some embodiments, the present invention provides a compound of formula I:

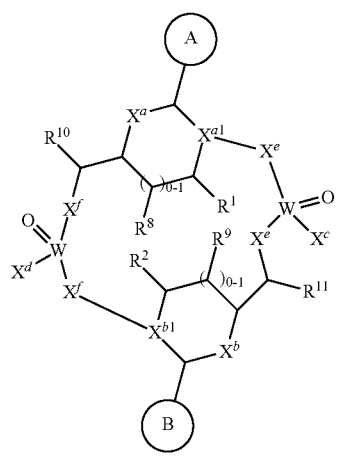

I or a pharmaceutically acceptable salt thereof,
wherein:
Ring A is selected from the group consisting of:

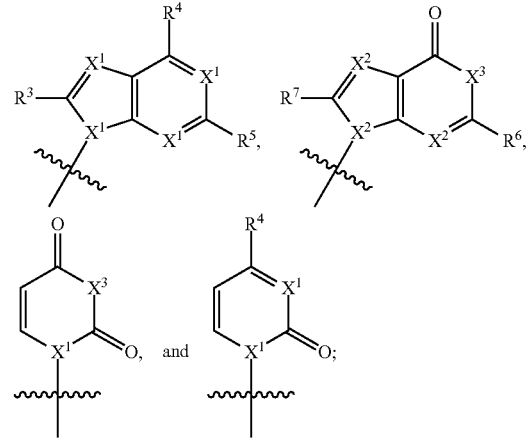

Ring B is selected from the group consisting of:

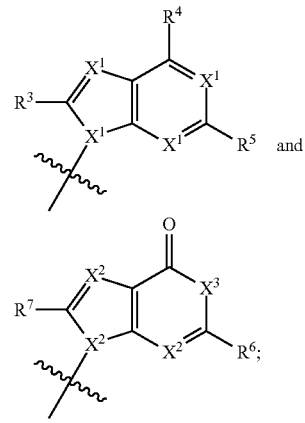

each $X^1$ and $X^2$ is independently —CR— or —N—;
$X^3$ is —C(R)$_2$—, —O—, or —NR—;
$X^a$ and $X^b$ are independently —C(R)$_2$—, —C(R)=C(R)—, —O—, —S—, —S(O)—, —S(O)$_2$—, or —N(R)—;
$X^{a1}$ and $X^{b1}$ are independently —C(R)— or —N—;
$X^c$ and $X^d$, when present, are independently optionally substituted oxygen, optionally substituted sulfur, a substituted nitrogen atom, BH$_3$, or optionally substituted C$_{1-12}$ aliphatic;
each $X^e$ and $X^f$ is independently —O—, —S—, or —N(R)—;
each W is independently P or S;
each $R^1$ and $R^2$ is independently selected from the group consisting of hydrogen, halogen, —NO$_2$, —CN, —OR$^a$, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, and optionally substituted C$_{1-12}$ aliphatic or C$_{1-4}$ alkoxy-C$_{1-4}$ alkyl;
each $R^3$, $R^4$, $R^5$, $R^6$, $R^7$, $R^{10}$, and $R^{11}$ is independently selected from the group consisting of hydrogen, halogen, —NO₂, —CN, —OR, —SR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, —OC(O)N(R)₂, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, and a 5-6 membered heteroaryl ring having 1-3 heteroatoms independently selected from nitrogen, oxygen, or sulfur;

each $R^8$ and $R^9$, when present, is independently selected from the group consisting of hydrogen, halogen, —NO₂, —CN, —OR$^a$, —SR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, —OC(O)N(R)₂, and an optionally substituted $C_{1-12}$ aliphatic;

each R is independently selected from the group consisting of hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur; or:

two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur; and $R^a$ is an oxygen protecting group or R.

In some embodiments, Ring A is

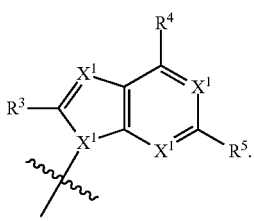

In some embodiments, Ring A is

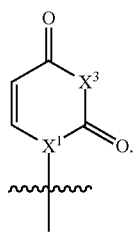

In some embodiments, Ring A is

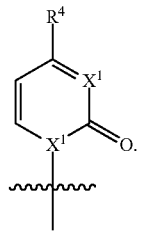

In some embodiments, Ring B is

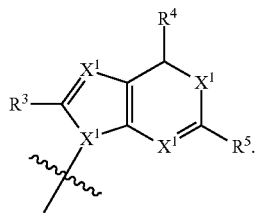

In some embodiments, Ring B is

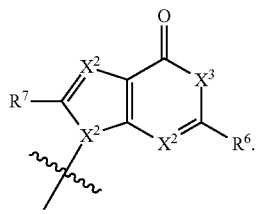

In some embodiments, $X^1$ is —CR—. In some embodiments, $X^1$ is —N—. In some embodiments, $X^2$ is —CR—. In some embodiments, $X^2$ is —N—. In some embodiments, $X^3$ is —C(R)₂—. In some embodiments, $X^3$ is —O—. In some embodiments, $X^3$ is —NR—.

In certain embodiments, $X^a$ is —C(R)₂—. In certain embodiments, $X^a$ is —C(R)=C(R)—. In certain embodiments, $X^a$ is —O—. In certain embodiments, $X^a$ is —S—. In certain embodiments, $X^a$ is —S(O)—. In certain embodiments, $X^a$ is —S(O)₂—. In certain embodiments, $X^a$ is —NR—.

In certain embodiments, $X^b$ is —C(R)₂—. In certain embodiments, $X^b$ is —C(R)=C(R)—. In certain embodiments, $X^b$ is —O—. In certain embodiments, $X^b$ is —S—. In certain embodiments, $X^b$ is —S(O)—. In certain embodiments, $X^b$ is —S(O)₂—. In certain embodiments, $X^b$ is —NR—.

In certain embodiments, $X^{a1}$ is —C(R)—. In certain embodiments, $X^{a1}$ is —N—. In certain embodiments, $X^{b1}$ is —C(R)—. In certain embodiments, $X^{b1}$ is —N—.

In some embodiments, $X^c$ is oxygen. In some embodiments, $X^c$ is sulfur. It will be appreciated that in certain embodiments where $X^c$ is oxygen or sulfur, the oxygen or sulfur atom may possess a formal negative charge. In some embodiments, $X^c$ is a substituted nitrogen atom. In some embodiments, the nitrogen is independently substituted with hydrogen or optionally substituted $C_{1-12}$ aliphatic groups. In some embodiments, $X^c$ is optionally substituted $C_{1-12}$ aliphatic.

In some embodiments, $X^d$ is oxygen. In some embodiments, $X^d$ is sulfur. It will be appreciated that in certain embodiments where $X^d$ is oxygen or sulfur, the oxygen or sulfur atom may possess a formal negative charge. In some embodiments, $X^d$ is a substituted nitrogen atom. In some embodiments, the nitrogen is independently substituted with hydrogen or optionally substituted $C_{1-12}$ aliphatic groups. In some embodiments, $X^d$ is optionally substituted $C_{1-12}$ aliphatic.

In some embodiments, $X^e$ is —O—. In some embodiments, $X^e$ is —S—. In some embodiments, $X^e$ is —N(R)—.

In some embodiments, $X^f$ is —O—. In some embodiments, $X^f$ is —S—. In some embodiments, $X^f$ is —N(R)—.

In some embodiments, W is P. In other embodiments, W is S.

In some embodiments, $R^1$ is hydrogen, halogen, —$OR^a$, —SR, —$N(R)_2$, and optionally substituted $C_{1-12}$ aliphatic or $C_{1-4}$ alkoxy-$C_{1-4}$ alkyl. In some embodiments, $R^1$ is hydrogen. In some embodiments, $R^1$ is halogen. In some embodiments, $R^1$ is —$OR^a$. In some embodiments, $R^1$ is —OH. In some embodiments, $R^1$ is fluoro. In some embodiments, $R^1$ is $C_{1-12}$ aliphatic. In some embodiments, $R^1$ is $C_{1-6}$ aliphatic. In some embodiments, $R^1$ is $C_{1-3}$ aliphatic. In some embodiments, $R^1$ is methyl. In some embodiments, $R^1$ is $C_{1-4}$ alkoxy-$C_{1-4}$ alkyl. In some embodiments, $R^1$ is methoxyethyl.

In some embodiments, $R^2$ is hydrogen, halogen, —$OR^a$, —SR, —$N(R)_2$, and optionally substituted $C_{1-12}$ aliphatic or $C_{1-4}$ alkoxy-$C_{1-4}$ alkyl. In some embodiments, $R^2$ is hydrogen. In some embodiments, $R^2$ is halogen. In some embodiments, $R^2$ is —$OR^a$. In some embodiments, $R^2$ is —OH. In some embodiments, $R^2$ is fluoro. In some embodiments, $R^2$ is $C_{1-12}$ aliphatic. In some embodiments, $R^2$ is $C_{1-6}$ aliphatic. In some embodiments, $R^2$ is $C_{1-3}$ aliphatic. In some embodiments, $R^2$ is methyl. In some embodiments, $R^2$ is $C_{1-4}$ alkoxy-$C_{1-4}$ alkyl. In some embodiments, $R^2$ is methoxyethyl.

In some embodiments, $R^3$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In certain embodiments, $R^3$ is hydrogen. In some embodiments, $R^3$ is halogen. In certain embodiments, $R^3$ is —$NO_2$. In some embodiments, $R^3$ is —CN. In certain embodiments, $R^3$ is —OR. In some embodiments, $R^3$ is $C_{1-12}$ aliphatic. In some embodiments, $R^3$ is $C_{1-6}$ aliphatic.

In some embodiments, $R^4$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In certain embodiments, $R^4$ is hydrogen. In some embodiments, $R^4$ is halogen. In certain embodiments, $R^4$ is —$NO_2$. In some embodiments, $R^4$ is —CN. In certain embodiments, $R^4$ is —OR. In some embodiments, $R^4$ is $C_{1-12}$ aliphatic. In some embodiments, $R^4$ is $C_{1-6}$ aliphatic.

In some embodiments, $R^5$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In certain embodiments, $R^5$ is hydrogen. In some embodiments, $R^5$ is halogen. In certain embodiments, $R^5$ is —$NO_2$. In some embodiments, $R^5$ is —CN. In certain embodiments, $R^5$ is —OR. In some embodiments, $R^5$ is $C_{1-12}$ aliphatic. In some embodiments, $R^5$ is $C_{1-6}$ aliphatic.

In some embodiments, $R^6$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In certain embodiments, $R^6$ is hydrogen. In some embodiments, $R^6$ is halogen. In certain embodiments, $R^6$ is —$NO_2$. In some embodiments, $R^6$ is —CN. In certain embodiments, $R^6$ is —OR. In some embodiments, $R^6$ is $C_{1-12}$ aliphatic. In some embodiments, $R^6$ is $C_{1-6}$ aliphatic.

In some embodiments, $R^7$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In certain embodiments, $R^7$ is hydrogen. In some embodiments, $R^7$ is halogen. In certain embodiments, $R^7$ is —$NO_2$. In some embodiments, $R^7$ is —CN. In certain embodiments, $R^7$ is —OR. In some embodiments, $R^7$ is $C_{1-12}$ aliphatic. In some embodiments, $R^7$ is $C_{1-6}$ aliphatic.

In some embodiments, $R^8$ is present. In other embodiments, $R^8$ is absent. In some embodiments, $R^8$ is hydrogen. In some embodiments, $R^8$ is halogen. In some embodiments, $R^8$ is —$OR^a$. In some embodiments, $R^8$ is optionally substituted $C_{1-12}$ aliphatic. In some embodiments, $R^8$ is $C_{1-6}$ aliphatic. In some embodiments, $R^8$ is $C_{1-3}$ aliphatic.

In some embodiments, $R^9$ is present. In other embodiments, $R^9$ is absent. In some embodiments, $R^9$ is hydrogen. In some embodiments, $R^9$ is halogen. In some embodiments, $R^9$ is —$OR^a$. In some embodiments, $R^9$ is optionally substituted $C_{1-12}$ aliphatic. In some embodiments, $R^9$ is $C_{1-6}$ aliphatic. In some embodiments, $R^9$ is $C_{1-3}$ aliphatic.

In some embodiments, $R^{10}$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In some embodiments, $R^{10}$ is optionally substituted phenyl, a 3-7 membered saturated or partially unsaturated monocyclic carbocyclic ring, a 3-7 membered saturated or partially unsaturated heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur In certain embodiments, $R^{10}$ is hydrogen. In some embodiments, $R^{10}$ is halogen. In some embodiments, $R^{10}$ is $C_{1-12}$ aliphatic. In some embodiments, $R^{10}$ is $C_{1-6}$ aliphatic.

In some embodiments, $R^{11}$ is hydrogen, halogen, —$NO_2$, —CN, —OR, —SR, —$N(R)_2$, —C(O)R, —$CO_2$R, —C(O)C(O)R, —C(O)$CH_2$C(O)R, —S(O)R, —$S(O)_2$R, —C(O)N$(R)_2$, —$SO_2N(R)_2$, —OC(O)R, —N(R)C(O)R, —N(R)N$(R)_2$, —N(R)C(=NR)N$(R)_2$, —C(=NR)N$(R)_2$, —C=NOR, —N(R)C(O)N$(R)_2$, —N(R)$SO_2N(R)_2$, —N(R)$SO_2$R, —OC(O)N$(R)_2$, or optionally substituted $C_{1-12}$ aliphatic. In some embodiments, $R^{11}$ is optionally substituted phenyl, a 3-7 membered saturated or partially unsaturated monocyclic carbocyclic ring, a 3-7 membered saturated or partially unsaturated heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur In certain embodiments, $R^{11}$ is hydrogen. In some embodiments, $R^{11}$ is halogen. In some embodiments, $R^{11}$ is $C_{1-12}$ aliphatic. In some embodiments, $R^{11}$ is $C_{1-6}$ aliphatic.

It will be appreciated that for compounds depicted herein, where negatively charges phosphates are shown, the disclosure contemplates both free and salt forms of such compounds, and tautomers thereof. In some embodiments, a provided compound may have one or more protonated nitrogens that balance the charge of a free phosphate.

In some embodiments, the present invention provides a compound of formula II:

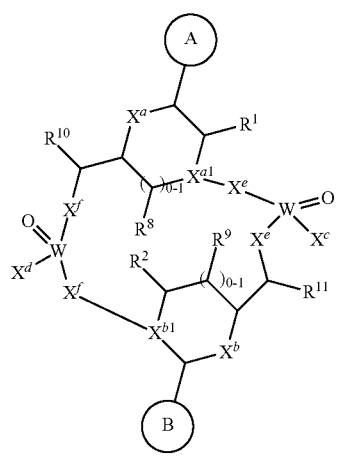

II or a pharmaceutically acceptable salt thereof,
wherein each of Ring A, Ring B, $X^a$, $X^b$, $X^c$, $X^e$, $X^f$, $X^{a1}$, $X^{b1}$, $X^2$, $X^3$, W, $R^1$, $R^2$, $R^6$, $R^7$, $R^8$, $R^9$, $R^{10}$, and $R^{11}$ is as defined above and described in classes and subclasses herein, both singly and in combination.

In some embodiments, a provided compound is other than:

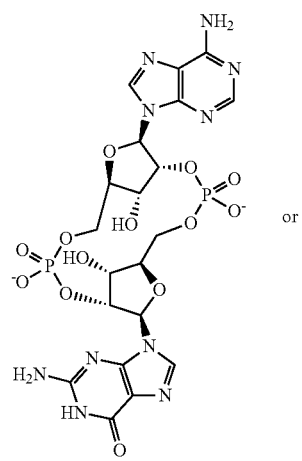

or

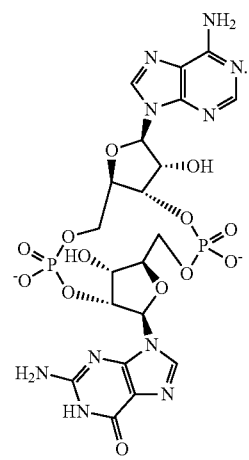

In some embodiments, a provided compound is of formula I-a or II-a:

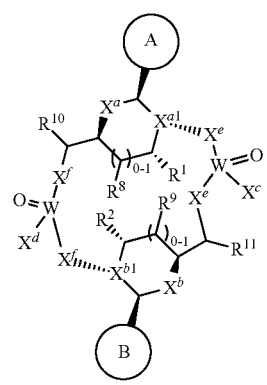

I-a

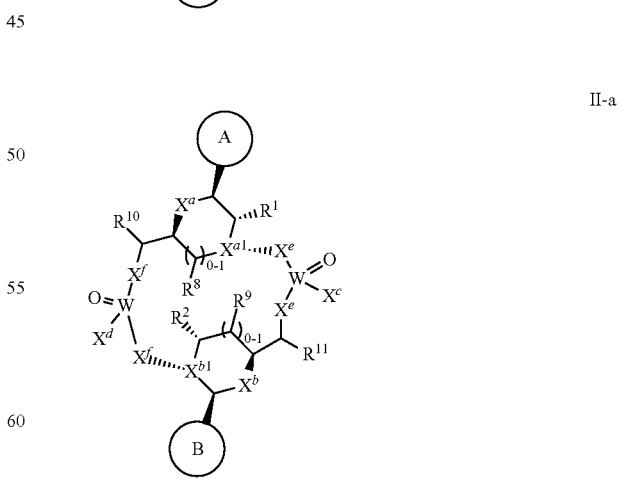

II-a or a pharmaceutically acceptable salt thereof.

In some embodiments, a provided compound is of formula III, IV, V, VI, VII, VIII, or IX:

III
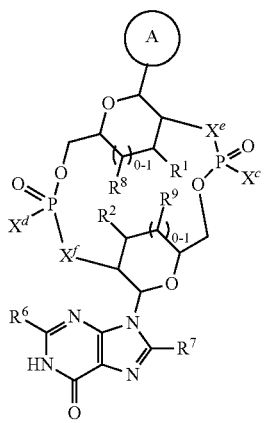
IV
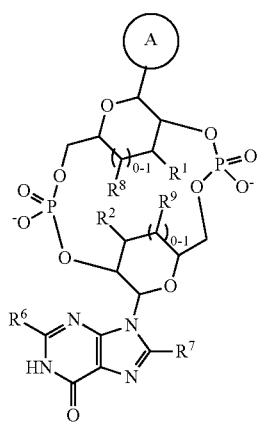
V
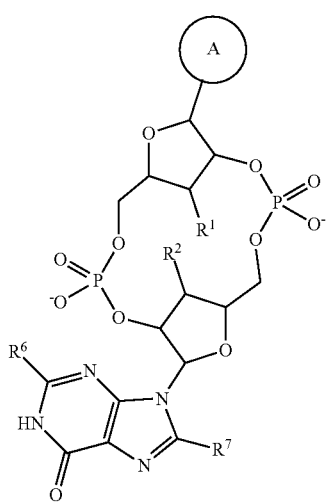
-continued
VI
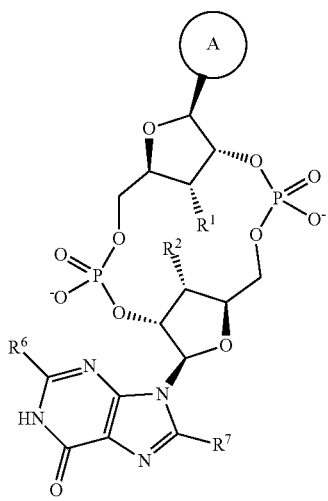
VII
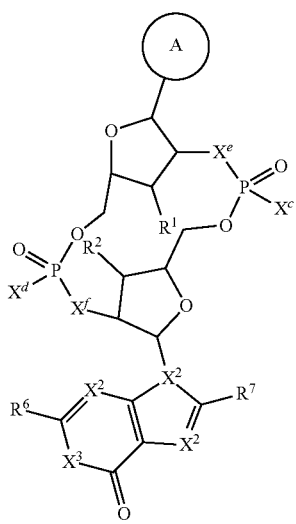
VIII
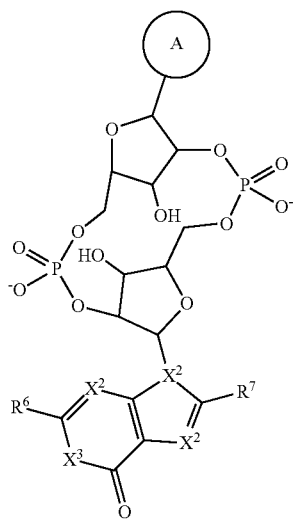

IX
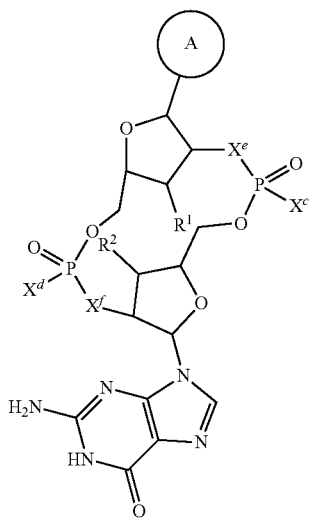
or a pharmaceutically acceptable salt thereof, wherein each of Ring A, $X^c$, $X^d$, $X^e$, $X^f$, $R^1$, $R^2$, $R^6$, $R^1$, $R^8$, $R^9$, $X^2$, and $X^3$ is as defined above and described in classes and subclasses herein, both singly and in combination.
In some embodiments, a provided compound is of formula X, XI, XII, XIII, XIV, XV, or XVI:
X
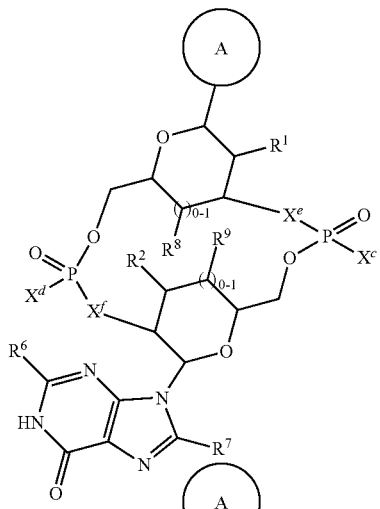
XI
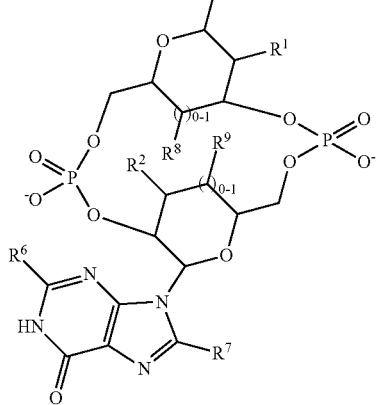
XII
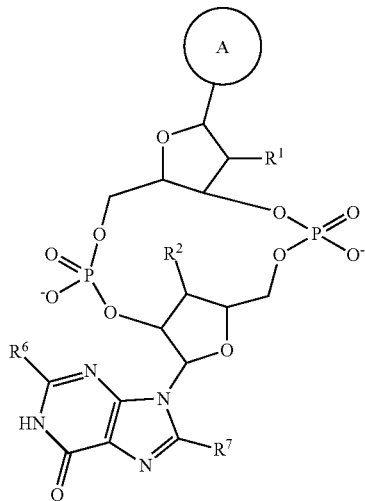
XIII
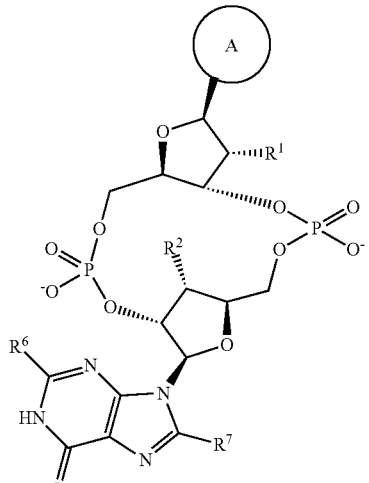
XIV
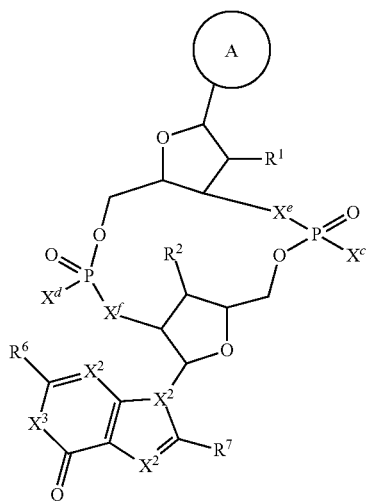

XV
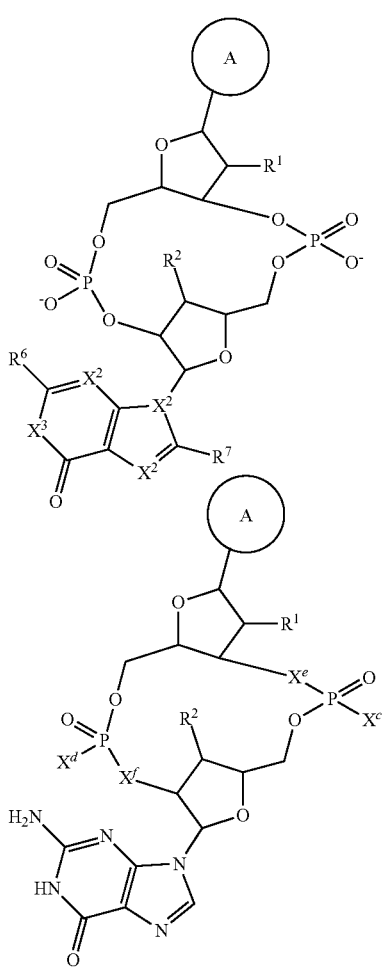
or a pharmaceutically acceptable salt thereof,
wherein each of Ring A, $X^c$, $X^d$, $X^e$, $X^f$, $R^1$, $R^2$, $R^6$, $R^7$, $R^8$, $R^9$, $X^2$, and $X^3$ is as defined above and described in classes and subclasses herein, both singly and in combination.
In some embodiments, a provided compound is selected from:
III-a
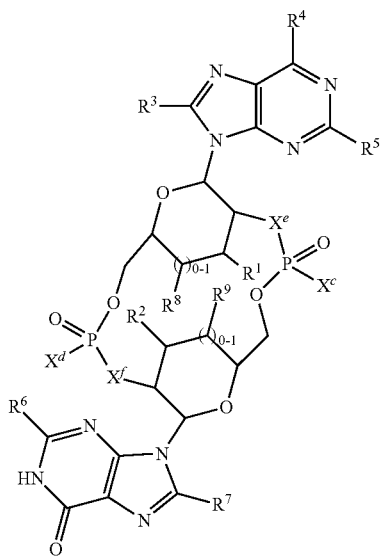
IV-a
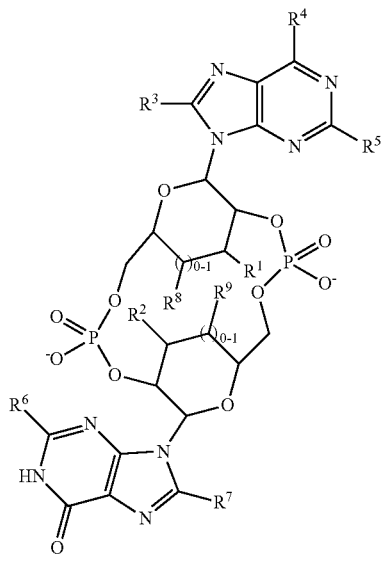
V-a
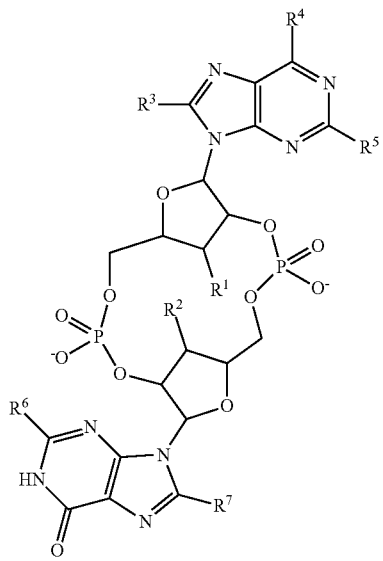
VI-a
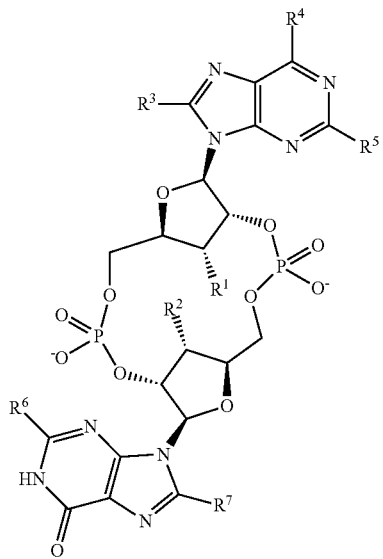

-continued
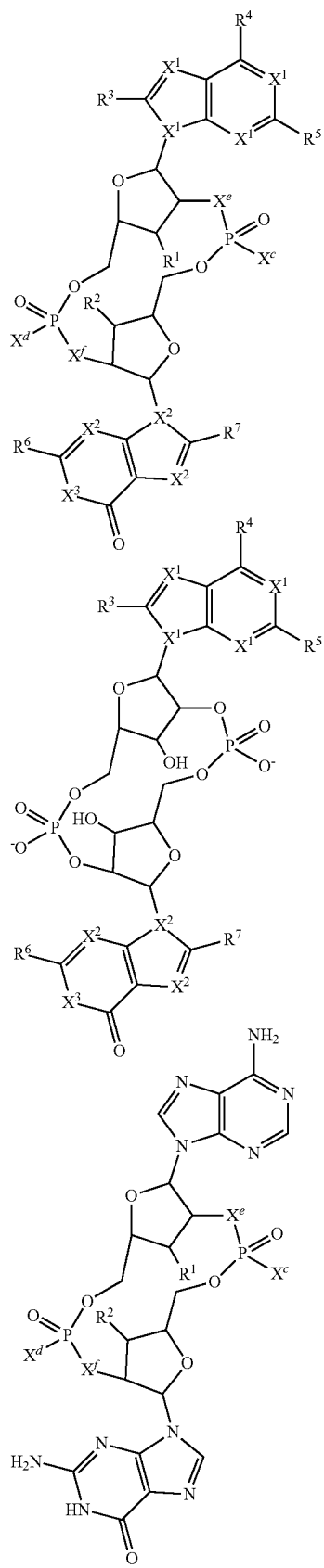
VII-a
VIII-a
IX-a
or a pharmaceutically acceptable salt thereof,
wherein each of Ring A, $X^c$, $X^d$, $X^e$, $X^f$, $R^1$, $R^2$, $R^6$, $R^7$, $R^8$, $R^9$, $X^2$, and $X^3$ is as defined above and described in classes and subclasses herein, both singly and in combination.
In some embodiments, a provided compound is selected from:
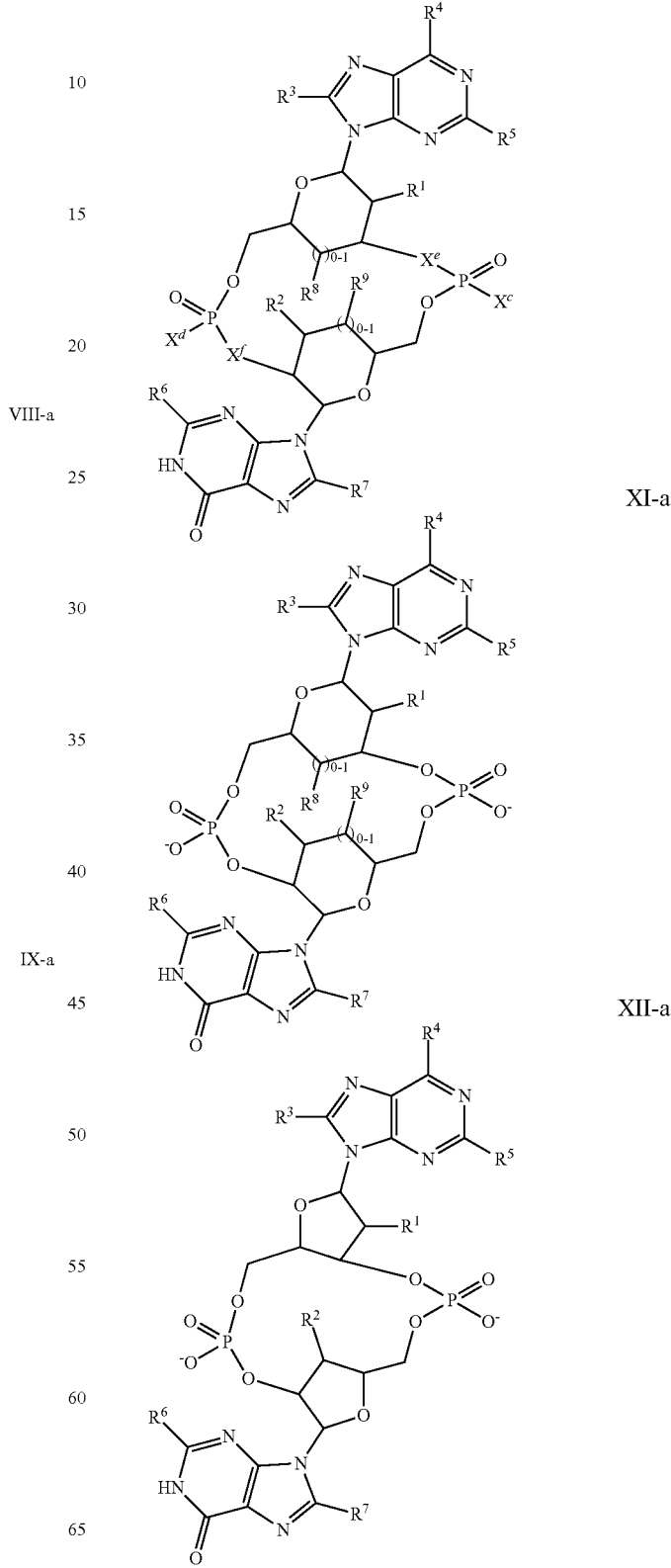
X-a
XI-a
XII-a XIII-a
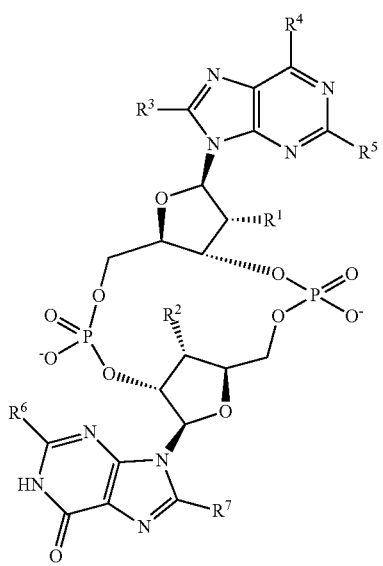
XIV-a
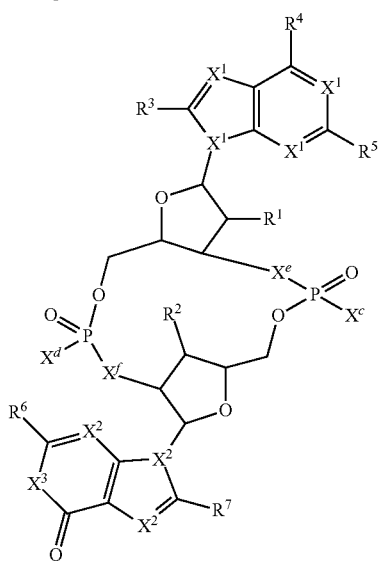
XV-a
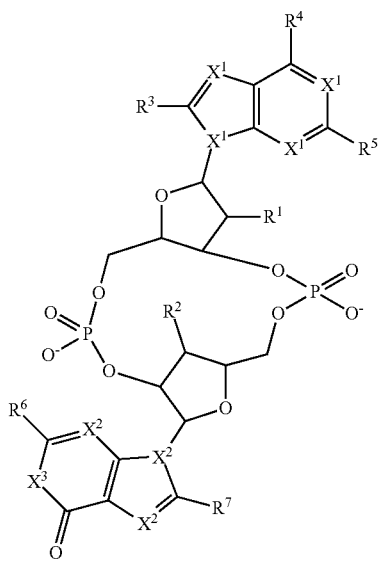
XVI-a
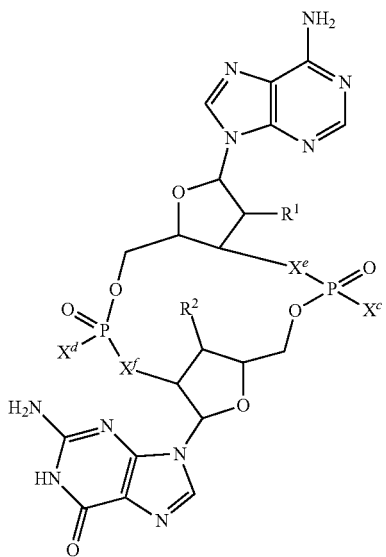
or a pharmaceutically acceptable salt thereof,
wherein each of Ring A, $X^c$, $X^d$, $X^e$, $X^f$, $R^1$, $R^2$, $R^6$, $R^7$, $R^8$, $R^9$, $X^2$, and $X^3$ is as defined above and described in classes and subclasses herein, both singly and in combination.
In some embodiments, a provided compound is selected from:
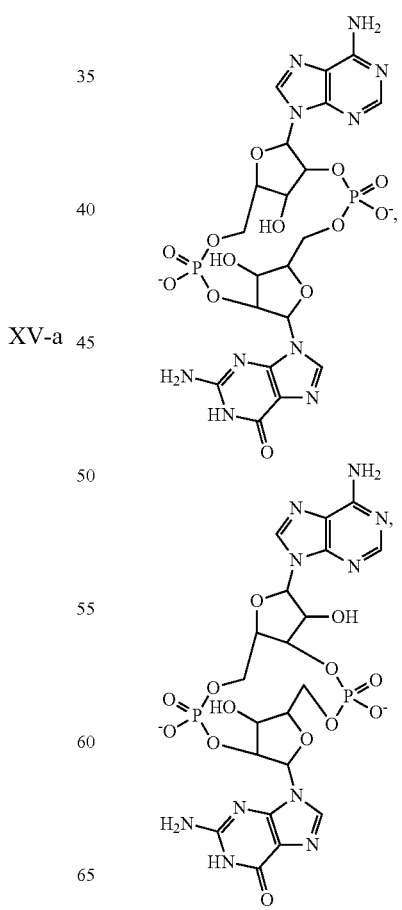

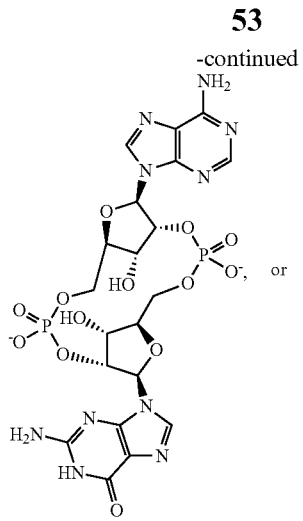

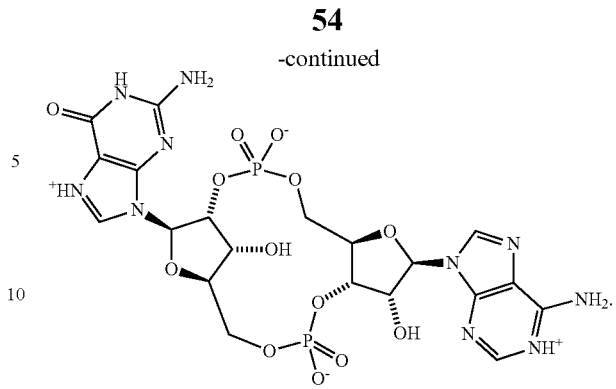

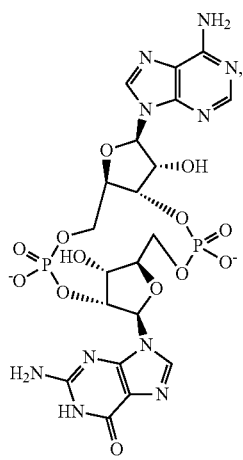

or a pharmaceutically acceptable salt thereof.

It will be appreciated that the compounds depicted in the immediately preceding paragraph may be drawn using other conventions. For example, the following two compounds are considered equivalent in chemical structure and stereochemistry:

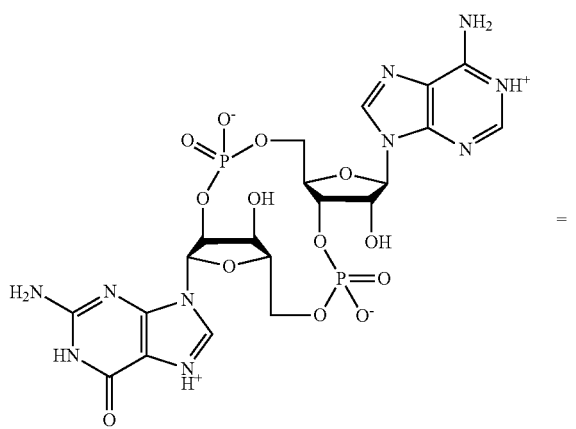

In some embodiments, provided compounds are in isolated form. In some embodiments, provided compounds are pure.

Pharmaceutical Compositions

Provided pharmaceutical compositions can be in a variety of forms including oral dosage forms, topic creams, topical patches, iontophoresis forms, suppository, nasal spray and inhaler, eye drops, intraocular injection forms, depot forms, as well as injectable and infusible solutions. Methods for preparing pharmaceutical composition are well known in the art.

Pharmaceutical compositions typically contain the active agent described herein in an amount effective to achieve the desired therapeutic effect while avoiding or minimizing adverse side effects. Pharmaceutically acceptable preparations and salts of the active agent are provided herein and are well known in the art. For the administration of cGAS modulators and the like, the amount administered desirably is chosen that is therapeutically effective with few to no adverse side effects. The amount of the therapeutic or pharmaceutical composition which is effective in the treatment of a particular disease, disorder or condition depends on the nature and severity of the disease, the target site of action, the subject's weight, special diets being followed by the subject, concurrent medications being used, the administration route and other factors that are recognized by those skilled in the art. The dosage can be adapted by the clinician in accordance with conventional factors such as the extent of the disease and different parameters from the subject. Effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", *Pharmacology and Toxicology*, July 2005, the entire contents of which are incorporated herein by reference).

Various delivery systems are known and can be used to administer active agent described herein or a pharmaceutical composition comprising the same.

The pharmaceutical compositions described herein can be administered by any suitable route including, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Other delivery systems well known in the art can be used for delivery of the pharmaceutical compositions described herein, for example via aqueous solutions, encapsulation in microparticles, or microcapsules. The pharmaceutical compositions of the present invention can also be delivered in a controlled release system. For example, a polymeric material can be used (see, e.g., Smolen and Ball, Controlled Drug Bioavailability, Drug product design and performance, 1984, John Wiley & Sons; Ranade and Hollinger, Drug Delivery Systems, pharmacology and toxicology series, 2003, $2^{nd}$ edition, CRRC Press). Alternatively, a pump may be used (Saudek et al., *N. Engl. J. Med.* 321:574 (1989)). The compositions described herein may also be coupled to a class of biodegradable polymers useful in achieving controlled release of the drug, for example, polylactic acid, polyorthoesters, cross-linked amphipathic block copolymers and hydrogels, polyhydroxy butyric acid, and polydihydropyrans.

As described above, pharmaceutical compositions desirably include a pharmaceutically acceptable carrier. The term carrier refers to diluents, adjuvants, excipients or vehicles with which modulators are administered. Such pharmaceutical carriers include sterile liquids such as water and oils including mineral oil, vegetable oil (e.g., soybean oil or corn oil), animal oil or oil of synthetic origin. Aqueous glycerol and dextrose solutions as well as saline solutions may also be employed as liquid carriers of the pharmaceutical compositions of the present invention. The choice of the carrier depends on factors well recognized in the art, such as the nature of the peptide, peptide derivative or peptidomimetic, its solubility and other physiological properties as well as the target site of delivery and application. Examples of suitable pharmaceutical carriers are described in Remington: The Science and Practice of Pharmacy by Alfonso R. Gennaro, 2003, $21^{th}$ edition, Mack Publishing Company. Moreover, suitable carriers for oral administration are known in the art and are described, for example, in U.S. Pat. Nos. 6,086,918, 6,673,574, 6,960,355, and 7,351,741 and in WO2007/131286, the disclosures of which are hereby incorporated by reference.

Further pharmaceutically suitable materials that may be incorporated in pharmaceutical preparations include absorption enhancers including those intended to increase paracellular absorption, pH regulators and buffers, osmolarity adjusters, preservatives, stabilizers, antioxidants, surfactants, thickeners, emollient, dispersing agents, flavoring agents, coloring agents, and wetting agents.

Examples of suitable pharmaceutical excipients include, water, glucose, sucrose, lactose, glycol, ethanol, glycerol monostearate, gelatin, starch flour (e.g., rice flour), chalk, sodium stearate, malt, sodium chloride, and the like. The pharmaceutical compositions comprising modulators can take the form of solutions, capsules, tablets, creams, gels, powders sustained release formulations and the like. The composition can be formulated as a suppository, with traditional binders and carriers such as triglycerides (see Remington: The Science and Practice of Pharmacy by Alfonso R. Gennaro, 2003, $21^{th}$ edition, Mack Publishing Company). Such compositions contain a therapeutically effective amount of the therapeutic composition, together with a suitable amount of carrier so as to provide the form for proper administration to the subject. The formulations are designed to suit the mode of administration and the target site of action (e.g., a particular organ or cell type).

The pharmaceutical compositions comprising the active agent described herein also include compositions formulated as neutral or salt forms. Pharmaceutically acceptable salts include those that form with free amino groups and those that react with free carboxyl groups. Non-toxic alkali metal, alkaline earth metal, and ammonium salts commonly used in the pharmaceutical industry include sodium, potassium, lithium, calcium, magnesium, barium, ammonium, and protamine zinc salts, which are prepared by methods well known in the art. Also included are non-toxic acid addition salts, which are generally prepared by reacting the compounds of the present invention with suitable organic or inorganic acid. Representative salts include the hydrobromide, hydrochloride, valerate, oxalate, oleate, laureate, borate, benzoate, sulfate, bisulfate, acetate, phosphate, tysolate, citrate, maleate, fumarate, tartrate, succinate, napsylate salts, and the like.

Examples of fillers or binders that may be used in accordance with the present invention include acacia, alginic acid, calcium phosphate (dibasic), carboxymethylcellulose, carboxymethylcellulose sodium, hydroxyethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. In certain embodiments, a filler or binder is microcrystalline cellulose.

Examples of disintegrating agents that may be used include alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium disulfite, disodium edathamil, disodium edetate, disodiumethylenediaminetetraacetate (EDTA) crosslinked polyvinylpyrrolidones, pregelatinized starch, carboxymethyl starch, sodium carboxymethyl starch, microcrystalline cellulose.

Examples of lubricants include calcium stearate, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL-leucine.

Examples of silica flow conditioners include colloidal silicon dioxide, magnesium aluminum silicate and guar gum. Another most preferred silica flow conditioner consists of silicon dioxide.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

In some embodiments, the present invention contemplates oral formulations containing the active agent described herein. For example, pharmaceutical compositions described herein may include a cyclodextrin or cyclodextrin derivative. Cyclodextrins are generally made up of five or more α-D-glycopyranoside unites linked 1->4. Typically, cyclodextrins contain a number of glucose monomers ranging from six to eight units in a ring, creating a cone shape (α-cyclodextrin: six membered sugar ring molecule, β-cyclodextrin: seven sugar ring molecule, γ-cyclodextrin: eight sugar ring molecule). Exemplary cyclodextrins and cyclodextrin derivatives are disclosed in U.S. Pat. No. 7,723,304, U.S. Publication No. 2010/0196452, and U.S. Publication No. 2010/0144624, the entire contents of each of which are incorporated herein by reference. For example, in some embodiments, a cyclodextrin in accordance with the present invention is an alkylated cyclodextrin, hydroxyalkylated cyclodextrin, or acylated cyclodextrin. In some embodiments, a cyclodextrin is a hydroxypropyl β-cyclodextrin. Exemplary cyclodextrin derivatives are disclosed in Szejtli, J. Chem Rev, (1998), 98, 1743-1753; and Szente, L and Szejtli, J., Advance Drug Delivery Reviews, 36 (1999) 17-28, the entire contents of each of which are hereby incorporated by reference. Examples of cyclodextin derivatives include methylated cyclodextrins (e.g., RAMEB; randomly methylated β-cyclodextrin); hydroxyalkylated cyclodextrins (hydroxypropyl-β-cyclodextrin and hydroxypropyl γ-cyclodextrin); acetylated cyclodextrins (acetyl-γ-cyclodextrin); reactive cyclodextrins (chlorotriazinyl β-cyclodextrin); and branched cyclodextrins (glucosyl- and maltosyl β-cyclodextrin); acetyl-γ-cyclodextrin; acetyl-β-cyclodextrin, sulfobutyl-β cyclodextrin, sulfated α-, β- and γ-cyclodextrins; sulfoalkylated cyclodextrins; and hydroxypropyl β-cyclodextrin.

Dosing

Typically, active agent described herein in an amount ranging from 0.001 to 100 mg/kg/day is administered to the subject. For example, in some embodiments, about 0.01 mg/kg/day to about 25 mg/kg/day, about 1 mg/kg/day to about 20 mg/kg/day, 0.2 mg/kg/day to about 10 mg/kg/day, about 0.02 mg/kg/day to about 0.1 mg/kg/day, or about 1 mg/kg/day to about 100 mg/kg/day is administered to the subject. In some embodiments, active agent described herein in an amount of about 10 µg/kg/day, 50 µg/kg/day, 100 µg/kg/day, 200 g/kg/day, 300 µg/kg/day, 400 µg/kg/day, 500 µg/kg/day, 600 µg/kg/day, 700 µg/kg/day, 800 g/kg/day, 900 µg/kg/day, or 1000 µg/kg/day is administered to the subject.

In some embodiments, the compound is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 g/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the compound is administered at an effective dose ranging from about 1-500 g/kg/day. In some embodiments, the compound is administered at an effective dose ranging from about 1-100 µg/kg/day. In some embodiments, the compound is administered at an effective dose ranging from about 1-60 µg/kg/day. In some embodiments, the compound is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

In some embodiments, a therapeutically effective amount of a compound may be an amount ranging from about 10-1,000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, a compound is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, a compound is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, a formulation comprising a compound as described herein administered as a single dose. In some embodiments, a formulation comprising a compound as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a compound as described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a compound as described herein is administered at regular intervals indefinitely. In some embodiments, a formulation comprising a compound as described herein is administered at regular intervals for a defined period. In some embodiments, a formulation comprising a compound as described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days, or a day.

Methods of Use

In certain embodiments provided compounds are useful in medicine. In some embodiments, provided compounds are useful in treating immune disease, disorders, or conditions.

In some embodiments, the present invention provides a method for the treatment or prevention of an immune disease, disorder, or condition comprising administering to a subject in need thereof a provided compound or a pharmaceutical composition thereof.

In some embodiments, the immune disease, disorder, or condition is an autoimmune disease, disorder, or condition. In certain embodiments, the immune disease, disorder, or condition is selected from the group consisting of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc. In some embodiments, the immune disease, disorder, or condition is characterized by inflammation. In some embodiments, the immune disease, disorder, or condition is caused by, sustained by, or related to cGAS activation. In some embodiments, the immune disease, disorder, or condition is caused by, sustained by, or related to STING activation.

In some embodiments the autoimmune disorder or disease is selected from Acute disseminated encephalomyelitis (ADEM), Addison's disease, Agammaglobulinemia, Alopecia areata, Amyotrophic lateral sclerosis (Also Lou Gehrig's disease; Motor Neuron Disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticarial, Autoimmune uveitis, Balo disease/Balo concentric sclerosis, Behcet's disease, Berger's disease, Bickerstaffs encephalitis, Blau syndrome, Bullous pemphigoid Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid Cogan syndrome, Cold agglutinin disease, Complement component 2 deficiency, Contact dermatitis, Cranial arteritis, CREST syndrome, Crohn's disease (idiopathic inflammatory bowel disease "IBD"), Cushing's Syndrome, Cutaneous leukocytoclastic angiitis, Dego's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Graves' disease, Guillain-Barre syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura, IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lupoid hepatitis aka Autoimmune hepatitis, Lupus erythematosus, Majeed syndrome, Meniere's disease, Microscopic polyangiitis, Miller-Fisher syndrome see Guillain-Barre Syndrome, Mixed connective tissue disease, Morphea, Mucha-Habermann disease aka Pityriasis lichenoides et varioliformis acuta, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome, Schnitzler syndrome, Scleritis, Scleroderma, Serum Sickness, Sjögren's syndrome, Spondyloarthropathy, Still's disease, Subacute bacterial endocarditis (SBE), Susac's syndrome, Sweet's syndrome, Sydenham chorea see PANDAS, Sympathetic ophthalmia, Systemic lupus erythematosis, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and Wegener's granulomatosis.

In certain embodiments, administration of a compound to a patient in need thereof results in a decrease of cGAS activity. In some embodiments, administration of a compound to a patient in need thereof results in a decrease of STING activity.

In some embodiments, compounds used in the provided methods are prepared by chemical synthesis.

In certain embodiments, the present invention provides a method of inhibiting cGAS comprising contacting cGAS with a provided compound. In some embodiments, the present invention provides a method of inhibiting cGAS in a patient comprising administering to a patient a provided compound. In certain embodiments, the present invention provides a method of inhibiting STING comprising contacting STING with a provided compound. In some embodiments, the present invention provides a method of inhibiting STING in a patient comprising administering to a patient a provided compound.

In certain embodiments, the present invention provides a method of modulating activity of an cGAS polypeptide, the method comprising contacting the cGAS polypeptide with a cGAS modulator designed by the methods disclosed herein, which modulating agent is not a known modulator, substrate, or product of cGAS. In some embodiments, the modulating agent is a provided compound.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits comprising the molecules (compounds and compositions as described above) of the invention. In one embodiment, the kit comprises one or more functional antibodies or function fragments thereof.

Kits of the invention may comprise one or more cGAMP parent molecules, or any mimic, analog or variant thereof. Kits may also comprise any of the cGAS variants, derivatives or mutants described herein. The kit may further comprise packaging and instructions and/or a delivery agent to form a formulation composition. The delivery agent may comprise a saline, a buffered solution, a lipid or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046; herein incorporated by reference in its entirety). In a further embodiment, the buffer solutions may be precipitated or it may be lyophilized. The amount of each component may be varied to enable consistent, reproducible higher concentration saline or simple buffer formulations. The components may also be varied in order to increase the stability of the compound or composition in the buffer solution over a period of time and/or under a variety of conditions. In one aspect, the present invention provides kits for research applications related to cGAS activity or cGAMP signaling, provided in an amount effective to study the concomitant signaling pathways when introduced into a target cell. The kits may further comprise a second or further compound or composition described herein. Such second or further molecules may modulate the immune response or an inflammatory process or comprise one or more therapeutic molecules. In one embodiment, a kit comprises at least one cGAS polypeptide and at least one cGAMP molecule. In one embodiment, the kits of the present invention comprise packaging and instructions.

cGAS Crystal Structures

Among other things, the present invention provides a crystalline (i.e., containing at least one crystal) or crystallizable composition comprising an cGAS polypeptide as described herein (see also Gao et al. *Cell* 153, 1094-1107 (2013), including supplementary materials). In some embodiments, such a provided composition consists of or consists essentially of the cGAS polypeptide. In some embodiments, a composition is considered to "consist of"

cGAS polypeptide if it includes only the polypeptide, one or more solvents, and optionally salts and/or metals. In some embodiments, such a provided composition includes one or more other agents such as one or more other polypeptides (e.g., one or more potential or actual cGAS binding partner polypeptides or nucleic acids) and/or one or more interacting agents (e.g., small molecules).

The present invention also provides structural information and/or analyses of cGAS polypeptide crystals and/or sets thereof. In some embodiments, such structural information includes, but is not limited to, diffraction patterns, and/or coordinates, as well as any data sets, images, models, and/or graphical representations thereof or generated therefrom. In some embodiments, such graphical representations may include, for example, space-filling models, molecular surface representations, shell or boundary models, ribbon models, stick models; and/or combinations thereof.

In some embodiments, provided information is or comprises differences observed between or among structures that differ from one another in the presence or absence of one or more binding partners and/or interacting agents. In some embodiments, provided information is or comprises differences observed between or among structures that differ from one another in the presence or absence of one or more binding partners and/or one or more modulators.

In some embodiments, such structural information and/or analyses may be embodied in a tangible medium (e.g., a computer-readable medium) or a storage environment. Thus, the present invention provides tangible embodiments of cGAS polypeptide crystal structure information, as well as its use, for example, by or with a computer system, in any of a variety of applications. For example, in some embodiments, such structural information and/or analyses may be accessed by, transported to or from, and/or otherwise utilized by a computer system or program running thereon.

Structure-Based Drug Design

In some embodiments, the present disclosure provides systems for identifying and/or characterizing cGAS modulators. In some embodiments, the present disclosure provides a method of designing or characterizing a cGAS modulator comprising the steps of:

a) providing an image of a cGAS crystal that includes at least one potential interaction site;
b) docking in the image at least one moiety that is a potential cGAS modulator structural element; and
c) assessing one or more features of a potential moiety-interaction site interaction.

In some embodiments, the at least one potential interaction site includes a site selected from the group consisting of Ser199, Ser420, Lys402, Glu211, Asp213, Asp307, Tyr421, Arg364, and combinations thereof. In certain embodiments, the at least one potential interaction site includes a site selected from the group consisting of Tyr421, Thr197, Ser366, Ser368, Arg364, and combinations thereof. In certain embodiments, the at least one potential interaction site includes a site selected from the group consisting of Tyr421, Asp213, Asp307, Arg364, and combinations thereof. In some embodiments, the at least one potential interaction site includes Arg161. In some embodiments, the modulator is a compound disclosed herein.

In some embodiments, the one or more features include at least one feature selected from the group consisting of: spatial separation between the moiety and the potential interaction site; energy of the potential moiety-interaction site interaction, and/or combinations thereof.

In some embodiments, a method further comprises a step of providing an image of a potential cGAS modulator comprising the moiety docked with the image of the cGAS crystal. In some embodiments, a method further comprises a step of comparing the image with that of a cGAS crystal including a bound known modulator, substrate, or product.

Computer Systems

Figure 17:
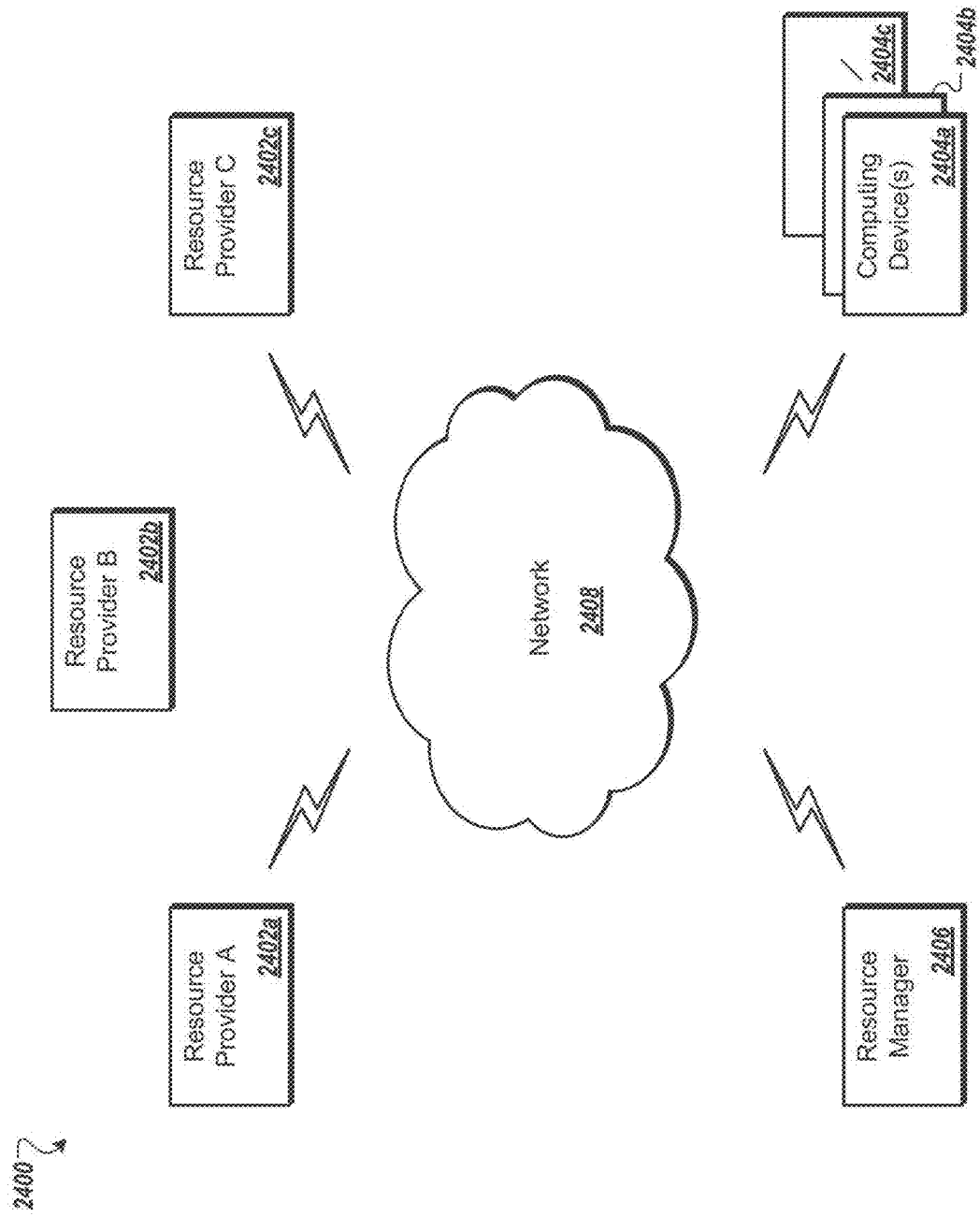
FIG. 17 is an exemplary block diagram of a computing device and a mobile computing device.

As will be appreciated by those skilled in the art, reading the present disclosure, in some aspects, the present invention is ideally suited for use in computer-implemented inventions. As shown in FIG. 17, an implementation of an exemplary cloud computing environment 2400 is shown and described. The cloud computing environment 2400 may include one or more resource providers 2402a, 2402b, 2402c (collectively, 2402). Each resource provider 2402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2402 may be connected to any other resource provider 2402 in the cloud computing environment 2400. In some implementations, the resource providers 2402 may be connected over a computer network 2408. Each resource provider 2402 may be connected to one or more computing device 2404a, 2404b, 2404c (collectively, 2404), over the computer network 2408.

The cloud computing environment 2400 may include a resource manager 2406. The resource manager 2406 may be connected to the resource providers 2402 and the computing devices 2404 over the computer network 2408. In some implementations, the resource manager 2406 may facilitate the provision of computing resources by one or more resource providers 2402 to one or more computing devices 2404. The resource manager 2406 may receive a request for a computing resource from a particular computing device 2404. The resource manager 2406 may identify one or more resource providers 2402 capable of providing the computing resource requested by the computing device 2404. The resource manager 2406 may select a resource provider 2402 to provide the computing resource. The resource manager 2406 may facilitate a connection between the resource provider 2402 and a particular computing device 2404. In some implementations, the resource manager 2406 may establish a connection between a particular resource provider 2402 and a particular computing device 2404. In some implementations, the resource manager 2406 may redirect a particular computing device 2404 to a particular resource provider 2402 with the requested computing resource.

FIG. 18 shows an example of a computing device 2500 and a mobile computing device 2550 that can be used to implement the techniques described in this disclosure. The computing device 2500 is intended to represent various forms of digital computers, such as laptops, desktops, workstations, personal digital assistants, servers, blade servers, mainframes, and other appropriate computers. The mobile computing device 2550 is intended to represent various forms of mobile devices, such as personal digital assistants, cellular telephones, smart-phones, tablet computers, and other similar computing devices. The components shown here, their connections and relationships, and their functions, are meant to be examples only, and are not meant to be limiting.

The computing device 2500 includes a processor 2502, a memory 2504, a storage device 2506, a high-speed interface 2508 connecting to the memory 2504 and multiple high-speed expansion ports 2510, and a low-speed interface 2512 connecting to a low-speed expansion port 2514 and the storage device 2506. Each of the processor 2502, the memory 2504, the storage device 2506, the high-speed interface 2508, the high-speed expansion ports 2510, and the low-speed interface 2512, are interconnected using various busses, and may be mounted on a common motherboard or in other manners as appropriate. The processor 2502 can process instructions for execution within the computing device 2500, including instructions stored in the memory 2504 or on the storage device 2506 to display graphical information for a GUI on an external input/output device, such as a display 2516 coupled to the high-speed interface 2508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 2504 stores information within the computing device 2500. In some implementations, the memory 2504 is a volatile memory unit or units. In some implementations, the memory 2504 is a non-volatile memory unit or units. The memory 2504 may also be another form of computer-readable medium, such as a magnetic or optical disk.

The storage device 2506 is capable of providing mass storage for the computing device 2500. In some implementations, the storage device 2506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2502), perform one or more methods, such as those described above. The instructions can also be stored by one or more storage devices such as computer- or machine-readable mediums (for example, the memory 2504, the storage device 2506, or memory on the processor 2502).

The high-speed interface 2508 manages bandwidth-intensive operations for the computing device 2500, while the low-speed interface 2512 manages lower bandwidth-intensive operations. Such allocation of functions is an example only. In some implementations, the high-speed interface 2508 is coupled to the memory 2504, the display 2516 (e.g., through a graphics processor or accelerator), and to the high-speed expansion ports 2510, which may accept various expansion cards (not shown). In the implementation, the low-speed interface 2512 is coupled to the storage device 2506 and the low-speed expansion port 2514. The low-speed expansion port 2514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2500 may be implemented in a number of different forms, as shown in the figure. For example, it may be implemented as a standard server 2520, or multiple times in a group of such servers. In addition, it may be implemented in a personal computer such as a laptop computer 2522. It may also be implemented as part of a rack server system 2524. Alternatively, components from the computing device 2500 may be combined with other components in a mobile device (not shown), such as a mobile computing device 2550. Each of such devices may contain one or more of the computing device 2500 and the mobile computing device 2550, and an entire system may be made up of multiple computing devices communicating with each other.

The mobile computing device 2550 includes a processor 2552, a memory 2564, an input/output device such as a display 2554, a communication interface 2566, and a transceiver 2568, among other components. The mobile computing device 2550 may also be provided with a storage device, such as a micro-drive or other device, to provide additional storage. Each of the processor 2552, the memory 2564, the display 2554, the communication interface 2566, and the transceiver 2568, are interconnected using various buses, and several of the components may be mounted on a common motherboard or in other manners as appropriate.

The processor 2552 can execute instructions within the mobile computing device 2550, including instructions stored in the memory 2564. The processor 2552 may be implemented as a chipset of chips that include separate and multiple analog and digital processors. The processor 2552 may provide, for example, for coordination of the other components of the mobile computing device 2550, such as control of user interfaces, applications run by the mobile computing device 2550, and wireless communication by the mobile computing device 2550.

The processor 2552 may communicate with a user through a control interface 2558 and a display interface 2556 coupled to the display 2554. The display 2554 may be, for example, a TFT (Thin-Film-Transistor Liquid Crystal Display) display or an OLED (Organic Light Emitting Diode) display, or other appropriate display technology. The display interface 2556 may comprise appropriate circuitry for driving the display 2554 to present graphical and other information to a user. The control interface 2558 may receive commands from a user and convert them for submission to the processor 2552. In addition, an external interface 2562 may provide communication with the processor 2552, so as to enable near area communication of the mobile computing device 2550 with other devices. The external interface 2562 may provide, for example, for wired communication in some implementations, or for wireless communication in other implementations, and multiple interfaces may also be used.

The memory 2564 stores information within the mobile computing device 2550. The memory 2564 can be implemented as one or more of a computer-readable medium or media, a volatile memory unit or units, or a non-volatile memory unit or units. An expansion memory 2574 may also be provided and connected to the mobile computing device 2550 through an expansion interface 2572, which may include, for example, a SIMM (Single In Line Memory Module) card interface. The expansion memory 2574 may provide extra storage space for the mobile computing device 2550, or may also store applications or other information for the mobile computing device 2550. Specifically, the expansion memory 2574 may include instructions to carry out or supplement the processes described above, and may include secure information also. Thus, for example, the expansion memory 2574 may be provide as a security module for the mobile computing device 2550, and may be programmed with instructions that permit secure use of the mobile computing device 2550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 2552), perform one or more methods, such as those described above. The instructions can also be stored by one or more storage devices, such as one or more computer- or machine-readable mediums (for example, the memory 2564, the expansion memory 2574, or memory on the processor 2552). In some implementations, the instructions can be received in a propagated signal, for example, over the transceiver 2568 or the external interface 2562.

The mobile computing device 2550 may communicate wirelessly through the communication interface 2566, which may include digital signal processing circuitry where necessary. The communication interface 2566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2568 using a radio-frequency. In addition, short-range communication may occur, such as using a Bluetooth®, Wi-Fi™, or other such transceiver (not shown). In addition, a GPS (Global Positioning System) receiver module 2570 may provide additional navigation- and location-related wireless data to the mobile computing device 2550, which may be used as appropriate by applications running on the mobile computing device 2550.

The mobile computing device 2550 may also communicate audibly using an audio codec 2560, which may receive spoken information from a user and convert it to usable digital information. The audio codec 2560 may likewise generate audible sound for a user, such as through a speaker, e.g., in a handset of the mobile computing device 2550. Such sound may include sound from voice telephone calls, may include recorded sound (e.g., voice messages, music files, etc.) and may also include sound generated by applications operating on the mobile computing device 2550.

The mobile computing device 2550 may be implemented in a number of different forms, as shown in the figure. For example, it may be implemented as a cellular telephone 2580. It may also be implemented as part of a smart-phone 2582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In certain embodiments, the present invention provides a system comprising a computer or computer readable medium in which a cGAS crystal structure, or coordinates thereof, is embedded and/or displayed.

In some embodiments, the present invention provides a method of designing and/or characterizing an cGAS modulator, which method comprises steps of:
(i) using a provided system to assess one or more structural features of the cGAS modulator; and
(ii) performing one or more in vitro, in vivo or cell-based assays to characterize the cGAS modulator.

In some embodiments, the method further comprises the step of performing a competition experiment between the cGAS modulator and a known cGAS modulator, substrate, or product. In some embodiments, the method further comprises the step of defining the three-dimensional shape of the inhibitor.

In some embodiments, the present invention provides a computer system containing a set of information to perform a design or characterization of an cGAS inhibitor having a user interface comprising a display unit, the set of information comprising:

(i) logic for inputting an information regarding a binding of a cGAS protein to a moiety known to bind cGAS protein;
(ii) logic for design a candidate cGAS inhibitor based on the binding of the cGAS protein to the moiety known to bind cGAS protein;
(iii) logic for determining an information regarding a binding of the cGAS protein to the candidate cGAS inhibitor; and
(iv) logic for making a conclusion regarding a cGAS inhibitory properties of the candidate cGAS inhibitor based on the determination of step (iii).

In some embodiments, the present invention provides a computer-readable storage medium containing a set of information for a general purpose computer having a user interface comprising, a display unit, the set of information comprising:
(i) logic for inputting an information regarding a binding of a cGAS protein to a chemical known to binding cGAS protein;
(ii) logic for design a candidate cGAS inhibitor based on the binding of the cGAS protein to the chemical known to bind cGAS protein;
(iii) logic for determining an information regarding a binding of the cGAS protein to the candidate cGAS inhibitor; and
(iv) logic for making a conclusion regarding a cGAS inhibitory properties of the candidate cGAS inhibitor based on the determination step of step (iii).

In some embodiments, the present invention provides an electronic signal or carrier wave that is propagated over the internet between computers comprising a set of information for a general purpose computer having a user interface comprising a display unit, the set of information comprising a computer-readable storage medium containing a set of information for a general purpose computer having a user interface comprising a display unit, the set of information comprising:
(i) logic for inputting an information regarding a binding of a cGAS protein to a chemical known to bind cGAS protein;
(ii) logic for designing a candidate cGAS inhibitor based on the binding of the cGAS protein to the chemical known to bind cGAS protein;
(iii) logic for determining an information regarding a binding of the cGAS protein to the candidate cGAS inhibitor; and
(iv) logic for making a conclusion regarding a cGAS inhibitory properties of the candidate cGAS inhibitor based on the determination of step (iii).

EXAMPLES

The following coordinates have been deposited in the RCSB Protein Data Bank, with which the skilled artisan will be familiar, and correspond to Tables 1-7 referenced herein. See also Gao et al. *Cell* 153, 1094-1107 (2013), including supplementary materials, the entire contents of which are hereby incorporated by reference herein. Furthermore, in the context of the ensuing FIGS. 1-4, 7, and 8-11, the data presented in Tables 1-7 of U.S. provisional patent application No. 61/819,369, filed May 3, 2013, is hereby incorporated by reference.

TABLE E1

| Sample | PDB code | rcsb code [1] | Table |
|---|---|---|---|
| cGAS | 4K8V | RCSB079037 | 1 |
| cGAS + DNA | 4K96 | RCSB079048 | 2 |
| cGAS + DNA + ATP | 4K97 | RCSB079049 | 3 |
| cGAS + DNA + 5'-pppG(2',5')pG | 4K98 | RCSB079050 | 4 |
| cGAS + DNA + 5'-pppdG(2',5')pdG | 4K99 | RCSB079051 | 5 |
| cGAS + DNA + 5'-pG(2',5')pA | 4K9A | RCSB079052 | 6 |
| cGAS + DNA + c[G(2',5')pA(3',5')p] | 4K9B | RCSB079053 | 7 |

[1] One method of accessing the RCSB Protein Data Bank is online at www.rcsb.org.

Example 1

Crystal Structures
Protein Expression and Purification

The gene encoding mouse cGAS was purchased from Open Biosystems Inc. The sequences corresponding to full-length and residues 147-507 of cGAS were inserted into a modified pRSFDuet-1 vector (Novagen), in which cGAS was separated from the preceding $His_6$-SUMO tag ("$His_6$" disclosed as SEQ ID NO: 52) by an ubiquitin-like protease (ULP1) cleavage site. The gene sequences were subsequently confirmed by sequencing. The fusion proteins were expressed in BL21 (DE3) RIL cell strain. The cells were grown at 37° C. until OD600 reached approx. 0.6. The temperature was then shifted to 18° C. and the cells were induced by addition of isopropyl β-D-1-thiogalactopyranoside (IPTG) to the culture medium at a final concentration of 0.3 mM. After induction, the cells were grown overnight. The fusion protein was purified over a Ni-NTA affinity column. The $His_6$-SUMO tag ("$His_6$" disclosed as SEQ ID NO: 52) was removed by ULP1 cleavage during dialysis against buffer containing 40 mM Tris-HCl, 0.3 M NaCl, 1 mM DTT, pH 7.5. After dialysis, the protein sample was further fractionated over a Heparin column, followed by gel filtration on a 16/60 G200 Superdex column. The final sample of cGAS (full-length) and cGAS (147-507) contain about 30 mg/ml protein, 20 mM Tris, 300 mM NaCl, 1 mM DTT, pH 7.5. The Se-methionine substituted protein was expressed in Se-methionine (Sigma) containing M9 medium and purified using the same protocol used for the wild-type protein. All the mutants were cloned and purified using the same protocol as used for preparation of the wild-type protein.

Crystallization

For crystallization of cGAS (147-507) in the free state, the protein was first diluted into about 15 mg/ml and then mixed with equal volume reservoir solution (0.1 M HEPES, 0.1 M $MgAc_2$, 20% PEG3350, pH 7.6) at 4° C. by using hanging drop vapor diffusion method.

For cGAS (147-507)-dsDNA binary complex, the sample was prepared by direct mixing protein with a 16-bp DNA (1-nt 5'-overhang at either end: upper strand 5'-AAATTGC-CGAAGACGAA-3'(SEQ ID NO: 47); lower strand 5'-TTTCGTCTTCGGCAATT-3' (SEQ ID NO: 48)) in a 1:1.2 molar ratio. The crystals were generated by hanging drop vapor diffusion method at 20° C., from drops mixed from 1 μl of cGAS-dsDNA solution and 1 μl of reservoir solution (0.1 M MES, 8% MPD, pH 6.6). The crystals of Se-methionine substituted cGAS (147-507) in complex with dsDNA were grown under the same condition.

The cGAS (147-507)-dsDNA-ATP, cGAS (147-507)-dsDNA-GTP, and cGAS (147-507)-dsDNA-3'-dGTP ternary complexes were prepared by mixing protein with dsDNA in a 1:1.2 molar ratio, and then incubated in the presence of ATP/GTP/3'-dGTP (5 mM) and $MgCl_2$ (10 mM) for 0.5 h at room temperature. The crystals for cGAS (147-507)-dsDNA-ATP complex were generated by hanging drop vapor diffusion method at 20° C., from drops mixed from 1 μl of cGAS-dsDNA-ATP solution and 1 μl of reservoir solution (0.1 M HEPES, 0.2 M CaAc$_2$, 20% PEG300, pH 7.7). For cGAS (147-507)-dsDNA-GTP and cGAS (147-507)-dsDNA-3'-dGTP complexes, the crystals were generated by sitting drop vapor diffusion method at 20° C., by mixing equal volume reservoir solution (for GTP: 0.1 M NaAc, 10% MPD, pH 5.0; for 3'-dGTP: 0.1 M NaAc, 12% MPD, pH 5.2) with the samples.

The cGAS (147-507)-dsDNA-GMP+ATP and cGAS (147-507)-dsDNA-GTP+ATP ternary complexes were prepared by mixing protein with dsDNA in a 1:1.2 molar ratio, and then incubated with GMP/GTP (5 mM), ATP (5 mM) and MgCl$_2$ (10 mM) for 0.5 h at room temperature. The crystals for cGAS (147-507)-dsDNA-GMP+ATP complex were generated by sitting drop vapor diffusion method at 20° C., from drops mixed cGAS-dsDNA-GMP+ATP solution with equal volume reservoir solution (0.1 M MES, 40% MPD, pH 6.0). The crystals for cGAS (147-507)-DNA-GTP+ATP complex were generated over two weeks by sitting drop vapor diffusion method at 20° C., by mixing equal volume reservoir solution (0.1 M HEPES, 0.2 M MgCl$_2$, 30% PEG300, pH 7.5) with the sample.

Structure Determination

The heavy atom derivative crystal of the free state was generated by soaking in a reservoir solution with 5 mM thimerosal for 24 h. The diffraction data sets for cGAS (147-507) in free state (both native and Hg-derivative) and DNA-bound state (both native and Se-derivative) were collected at the Brookhaven National Laboratory. The data sets for all the ternary complexes were collected at the Advanced Photo Source (APS) at the Argonne National Laboratory. The diffraction data were indexed, integrated and scaled using the HKL2000 program (Otwinowski and Minor, 1997). The structure of Hg-substituted cGAS (147-507) in free state and Se-substituted cGAS (147-507) in DNA bound state were both solved using single-wavelength anomalous dispersion method as implemented in the program PHENIX (Adams et al., 2010). The model building was carried out using the program COOT (Emsley et al., 2010) and structural refinement was carried out using the program PHENIX (Adams et al., 2010). The statistics of the data collection and refinement for free and binary structures are shown in Table S1. The structures of all the ternary complexes were solved using molecular replacement method in PHASER (McCoy et al., 2007) using the binary structure as the search model. The model building was conducted using the program COOT (Emsley et al., 2010) and structural refinement was conducted using the program PHENIX (Adams et al., 2010). The statistics of the data collection and refinement are shown in Table S2 and S3.

TABLE S1

Data collection and refinement statistics for structures of cGAS in free and DNA bound state

| Crystal | cGAS | cGAS + DNA |
|---|---|---|
| Beam line | NSLS-29X | NSLS-29X |
| Wavelength | 0.9790 | 0.9790 |
| Space group | P2$_1$ | C2 |
| Unit cell | | |
| a, b, c (Å) | 86.6, 84.1, 124.7 | 181.9, 93.8, 75.5 |
| α, β, γ (°) | 90.0, 92.7, 90.0 | 90.0, 97.7, 90.0 |
| Resolution (Å) | 50-2.0 (2.07-2.00)$^a$ | 50-2.1 (2.18-2.10)$^a$ |
| R$_{merge}$ | 0.179 (0.493) | 0.089 (0.511) |
| I/σ (I) | 15.7 (3.6) | 15.8 (3.1) |
| Completeness (%) | 99.3 (98.6) | 99.8 (100) |
| Redundancy | 7.6 (7.7) | 5.5 (5.3) |
| Number of unique reflections | 118611 | 74352 |
| R$_{work}$/R$_{free}$ (%) | 17.5/20.8 | 20.2/22.6 |
| Number of non-H atoms | | |
| Protein/DNA | 11957 | 7257 |
| Water | 1357 | 722 |
| Ion | 4 | 2 |
| Average B factors (Å$^2$) | | |
| Protein | 34.01 | 40.90 |
| DNA | | 68.30 |
| Water | 35.56 | 43.80 |
| Ion | 13.80 | 56.96 |
| R.m.s. deviations | | |
| Bond lengths (Å) | 0.010 | 0.003 |
| Bond angles (°) | 1.207 | 0.947 |

$^a$Highest resolution shell (in Å) shown in parentheses.

TABLE S2

Data collection and refinement statistics of ternary complexes of cGAS and dsDNA with ATP, GTP, and 3'-dGTP

| Crystal | cGAS + DNA + ATP | cGAS + DNA + GTP [5'-pppG(2',5')pG] | cGAS + DNA + 3'-dGTP [5'-pppdG(2',5')pdG] |
|---|---|---|---|
| Beam line | APS-24ID-C | APS-24ID-E | APS-24ID-E |
| Wavelength | 0.9823 | 0.9792 | 0.9792 |
| Space group | I222 | I222 | I222 |
| Unit cell | | | |
| a, b, c (Å) | 86.2, 99.4, 131.5 | 85.4, 97.9, 133.5 | 85.1, 97.6, 131.4 |
| α, β, γ (°) | 90.0, 90.0, 90.0 | 90.0, 90.0, 90.0 | 90.0, 90.0, 90.0 |
| Resolution (Å) | 50-2.4 (2.54-2.41)$^a$ | 50-1.9 (2.04-1.94)$^a$ | 50-2.0 (2.05-1.95)$^a$ |
| R$_{merge}$ | 0.079 (0.577) | 0.067 (0.643) | 0.079 (0.700) |
| I/σ (I) | 14.2 (2.4) | 20.5 (2.2) | 17.5 (2.3) |
| Completeness (%) | 99.6 (97.8) | 98.9 (93.5) | 100 (100) |
| Redundancy | 6.3 (6.3) | 9.1 (5.6) | 10.7 (10.7) |
| Number of unique reflections | 22099 | 41225 | 40199 |
| R$_{work}$/R$_{free}$ (%) | 19.3/23.6 | 15.7/19.9 | 17.6/21.2 |

TABLE S2-continued

Data collection and refinement statistics of ternary
complexes of cGAS and dsDNA with ATP, GTP, and 3'-dGTP

| Crystal | cGAS + DNA + ATP | cGAS + DNA + GTP [5'-pppG(2',5')pG] | cGAS + DNA + 3'-dGTP [5'-pppdG(2',5')pdG] |
|---|---|---|---|
| Number of non-H atoms | | | |
| Protein/DNA | 3492 | 3521 | 3521 |
| Water | 147 | 363 | 318 |
| Ion | 3 | 3 | 3 |
| Other ligands | 31 | 55 | 53 |
| Average B factors (Å$^2$) | | | |
| Protein | 51.83 | 35.77 | 38.17 |
| DNA | 83.79 | 64.04 | 64.83 |
| Water | 44.70 | 40.68 | 40.78 |
| Ion | 35.56 | 21.95 | 35.32 |
| Other ligands | 58.44 | 32.66 | 43.53 |
| R.m.s. deviations | | | |
| Bond lengths (Å) | 0.007 | 0.018 | 0.008 |
| Bond angles (°) | 1.190 | 2.183 | 1.718 |

$^a$Highest resolution shell (in Å) shown in parentheses.

TABLE S3

Data collection and refinement statistics of ternary complexes
of cGAS and dsDNA with GMP + ATP and GTP + ATP

| Crystal | cGAS + DNA + GMP + ATP [5'-pG(2',5')pA] | cGAS + DNA + GTP + ATP c[G(2',5')pA(3',5')p] |
|---|---|---|
| Beam line | APS-24ID-C | APS-24ID-E |
| Wavelength | 0.9795 | 0.9792 |
| Space group | I222 | I222 |
| Unit cell | | |
| a, b, c (Å) | 85.4, 98.0, 131.3 | 85.3, 98.3, 130.0 |
| α, β, γ (°) | 90.0, 90.0, 90.0 | 90.0, 90.0, 90.0 |
| Resolution (Å) | 50-2.3 (2.39-2.26)$^a$ | 50-2.3 (2.38-2.26)$^a$ |
| $R_{merge}$ | 0.059 (0.303) | 0.084 (0.904) |
| I/σ (I) | 31.5 (4.8) | 17.6 (2.4) |
| Completeness (%) | 98.3 (89.2) | 100 (100) |
| Redundancy | 12.1 (5.5) | 9.7 (9.9) |
| Number of unique reflections | 25590 | 25950 |
| $R_{work}/R_{free}$ (%) | 16.8/21.0 | 17.6/21.8 |
| Number of non-H atoms | | |
| Protein/DNA | 3521 | 3518 |
| Water | 209 | 189 |
| Ion | 1 | 1 |
| Other ligands | 46 | 45 |
| Average B factors (Å$^2$) | | |
| Protein | 43.30 | 48.35 |
| DNA | 74.18 | 71.50 |
| Water | 43.86 | 43.94 |
| Ion | 30.20 | 25.89 |
| Other ligands | 54.77 | 89.75 |
| R.m.s. deviations | | |
| Bond lengths (Å) | 0.005 | 0.010 |
| Bond angles (°) | 1.433 | 1.933 |

$^a$Highest resolution shell (in Å) shown in parentheses.

Structure of Cyclic GMP-AMP Synthase (cGAS)

We have solved the 2.0 Å crystal structure of cGAS (construct 147-507) (FIG. 8A) in the free state (FIGS. 1 A and 8B). The protein adopts a bilobal scaffold with mixed α/β topology (FIG. 1A; x-ray statistics in Table S1) characteristic of members of the nucleotidyltransferase superfamily. A DALI search identified ILF2/NF45, which contains a nucleotidyltransferase fold (PDB: 4AT8) (Wolkowicz and Cook, 2012), as most closely resembling the fold of cGAS, with a Z score of 15.1 and r.m.s.d of 3.8 Å. In addition, the free state of human oligoadenylate synthetase 1 (OAS1) (PDB: 1PX5) (Hartmann et al. 2003) exhibited a Z score of 13.3 and a r.m.s.d. of 4.1 Å (comparison of cGAS and OAS1 in the free state in stereo in FIG. 8C).

Structure of Binary Complex of cGAS with Bound dsDNA

We have cocrystallized cGAS bound to a 16-bp complementary dsDNA (plus 1-nt 5'-overhang at either end) and solved the structure of the binary complex at 2.1 Å resolution (x-ray statistics in Table S1). The structure of the binary complex is shown in FIG. 1B. The majority of the intermolecular contacts in the binary cGAS-dsDNA complex (summarized in FIG. 1C) are between cGAS and the sugar-phosphate backbone of the DNA (FIG. 9A, B), with only one base-specific contact (FIG. 9B). The superposed structures of cGAS in the free (light gray) and dsDNA-bound (dark gray) states are shown in FIG. 1D. There are large conformational changes on formation of the binary dsDNA complex as can be seen within a β-sheet segment containing catalytic Glu211, Asp213 and Asp307 residues (FIG. 1E), as well for loop and helical segments within the catalytic pocket containing Ser199 (FIG. 1F). Thus, a β-sheet segment shifts by 5.1 Å on complex formation (FIG. 9C), as does Arg161 involved in base-specific recognition by 9.2 Å (FIG. 9D), as do Tyr and Lys residues within loop segments by up to 17.6 Å (FIG. 9E). Equally important, a very narrow entrance leads to the catalytic pocket for cGAS in the free state (FIG. 1G), while this entrance widened significantly in the binary complex with DNA (FIG. 1H). The cGAS fold in the dsDNA bound state is similar to that reported recently for the OAS1 in the dsRNA bound state plus 2'-dATP (PDB: 4IG8) (Donovan et al. 2013) (comparison of proteins in complexes in stereo in FIG. 9D; Z score of 18.2 and r.m.s.d. of 3.2 Å between the two protein folds).

Structure of Ternary Complex of cGAS with dsDNA and Bound ATP

We cocrystallized cGAS bound to dsDNA and ATP and solved the structure of the ternary complex at 2.4 Å resolution. The ATP is bound in the catalytic pocket positioned within the interior of the cGAS in the ternary complex (FIG. 2A). There is close superposition of the binary complex of cGAS and dsDNA with the ternary complex containing bound ATP as shown in FIG. 2B, with essentially minimal conformational changes in either the β-sheet segment carrying the catalytic acidic residues (FIG. 2C) or the loop and helix segments forming the catalytic pocket (FIG. 2D) on ternary complex formation. The only notable change is the movement of the side chain of Glu211 towards the other two acidic residues in the ternary complex (FIG. 2C). The triphosphate group of ATP is hydrogen bonded to polar side chains (Ser199, Ser420 and Lys402), while two bound cations (tentatively assigned to $Mg^{2+}$) serve a bridging role for interactions between the triphosphate and the side chains of catalytic acidic residues (Glu211, Asp213 and Asp307) (FIG. 2E). In addition, the adenine ring of bound ATP stacks over Tyr421 in one direction and partially over the guanidinium group of Arg364 in the other direction (FIG. 2F).

It should be noted that we observe additional weak electron density (dark gray contours in FIG. 2G) that is unaccounted for at this time in the 2.4 Å structure of the ternary complex. The additional density could be either water molecules or an AMP molecule with modest (30%) occupancy. A view of the bound ATP looking into the catalytic pocket of the ternary complex is shown in FIG. 2H.

Structure of Ternary Complex of cGAS with dsDNA and Bound 5'-pppG(2',5)pG

We cocrystallized cGAS bound to dsDNA and GTP and solved the structure of the ternary complex at 1.9 Å resolution. The structure of the ternary complex is shown in FIG. 3A (x-ray statistics in Table S2). Notably, phosphodiester bond formation has occurred in the catalytic pocket yielding the bound ligand 5'-pppGpG (shown positioned in the catalytic pocket in space-filling representation in FIG. 3A). Importantly, minimal conformational changes occurred on proceeding from the binary complex to the ternary complex with bound 5'-pppGpG (FIG. 10A-C).

Strikingly, the GpG linkage of 5'-pppGpG is 2',5' rather than the anticipated 3',5', with the first and second G residues in addition adopting syn and anti glycosidic torsion orientations, respectively (FIG. 10D). The triphosphate group of 5'-pppG(2',5')pG is coordinated to two cations (FIG. 3B), with the first G stacked on Tyr421, while the second G uses its Watson-Crick edge to hydrogen bond with polar side chains (Thr197, Ser366 and Ser368), and its Hoogsteen edge to hydrogen bond with Arg364 (FIG. 3C). The observed 5'-pppG(syn)(2',5')pG(anti) topology can be traced with a high degree of confidence because of the clear density observed for this intermediate of the reaction in the 1.9 Å structure of the ternary complex (2Fo-Fc map in FIG. 3D, with two views of the Fo-Fc omit map shown in FIG. 10E). A view of the bound 5'-pppG(2',5')pG looking into the catalytic pocket of the ternary complex shown is in FIG. 3E. We have superposed the structures of bound 5'-pppG(2',5')pG (gray) and ATP (dark gray) in their respective ternary complexes with cGAS and dsDNA, and observe that the first G of the bound 5'-pppG(2',5')pG is positioned in the plane of the bound ATP (FIG. 10F). The two bound cations have been tentatively assigned to $Mg^{2+}$ based on omit maps (FIG. 10G) and the octahedral coordination around each cation (FIG. 10H, I).

We also grew crystals of the ternary complex with 3'-dGTP, and observed formation of the related 5'-pppdG (2',5')pdG intermediate (cannot form a 3',5' linkage) in the 2.1 Å structure of this complex (x-ray statistics in Table S2).

Structure of Ternary Complex of cGAS with dsDNA and Bound 5'-pG(2',5)pA

We have also cocrystallized cGAS in the presence of dsDNA, GMP, and ATP and solved the structure of a complex at 2.3 Å resolution (structural statistics in Table S3). By using GMP rather than GTP, we hoped to trap the intermediate following formation of the first phosphodiester bond, and observed indeed the bound linear product of 5'-pG(syn)(2',5')pA(anti) (FIG. 3F, G). No $Mg^{2+}$ cations were observed in the absence of a triphosphate moiety in the product. Notably, attempts at cocrystallization of cGAS with dsDNA, GTP, and AMP only yielded crystals that diffracted very poorly (12 Å resolution). We observed good superposition of the intermediates 5'-pppG(syn)(2',5')pG(anti) (in dark gray) and 5'-pG(syn)(2',5')pA(anti) (in light gray) as shown in FIG. 3H.

Structure of Ternary Complex of cGAS with dsDNA and Bound c[G(2',5)pA (3',5')p]

We cocrystallized cGAS with dsDNA, GTP, and ATP and solved the structure of the complex at 2.3 Å resolution. These crystals took two weeks to grow, unlike other crystals mentioned above, that grew within a few days. The structure of the ternary complex is shown in FIG. 4A (x-ray statistics in Table S3). Most unexpectedly, the bound small ligand shown in a space-filling representation in FIG. 4A, is a cyclic dinucleotide. Notably, no conformational changes occurred on proceeding from the binary complex to the ternary complex with bound cyclic dinucleotide, with even the side chain of Glu211 adopting identical orientations (FIG. 11A-C).

Figure 4:
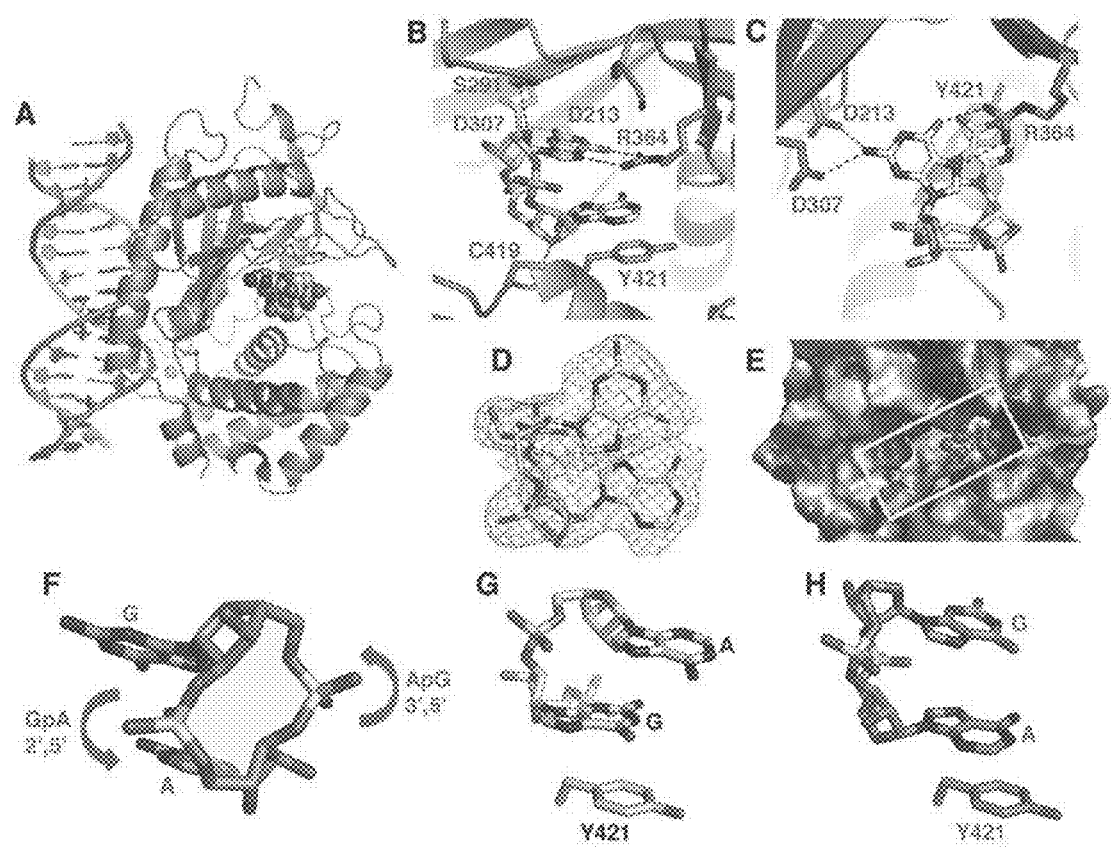
FIG. 4, comprising panels A-H, shows Structures of the Ternary Complex of cGAS, DNA with Bound Product c[G(2',5')pA(3',5')p]. (A) 2.3 Å crystal structure of the ternary complex of cGAS bound to dsDNA and product c[G(2',5')pA(3',5')p]. The protein and DNA are shown in ribbon, with bound product c[G(2',5')pA(3',5')p] in a space-filling representation. (B, C) Two alternate views of intermolecular contacts between product c[G(2',5')pA(3',5')p] and catalytic pocket residues in the ternary complex. (D) 2Fo-Fc electron density map contoured at 1.2σ of bound c[G(2',5')pA(3',5')p] in the catalytic pocket of the ternary complex. (E) View of bound c[G(2',5')pA(3',5')p] in a space-filling representation positioned towards on end of the catalytic pocket, with the protein in an electrostatic representation. (F) A view of c[G(2',5')pA(3',5')p] highlighting the 2',5' linkage at the GpA step and the 3',5' linkage at the ApG step. (G) Stacking of the G residue of 5'-pG(2',5')pA on Tyr 421 in its ternary complex with cGAS and dsDNA. (H) Stacking of the A residue of c[G(2',5')pA(3',5')p] on Tyr 421 in its ternary complex with cGAS and dsDNA.
Figure 11:
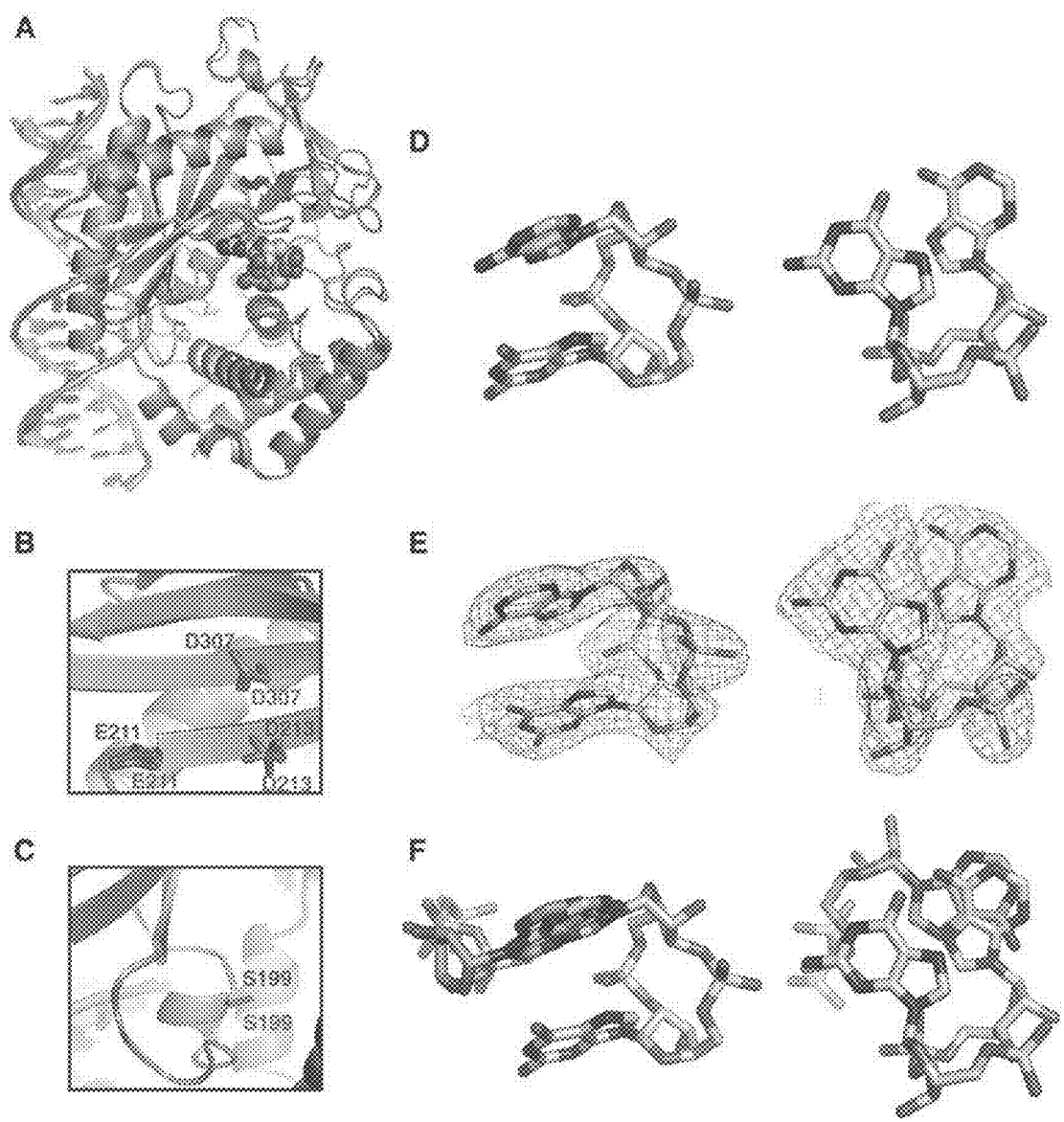
FIG. 11, comprising panels A-F, shows Structures of cGAS and c[G(2',5')pA(3',5')p] Bound in the Catalytic Pocket of the Ternary Complex Formed upon Crystallization with GTP+ATP. (A) Superposed structures of the binary complex of cGAS and DNA (gray) and the ternary complex with added GTP+ATP for which the bound product is c[G(2',5')pA(3',5')p] (dark gray) obtained from crystallization with ATP and GTP. (B, C) No conformational changes occurred in the backbone within the β-sheet (panel B) and catalytic pocket (panel C) segments on proceeding from the binary complex to the ternary complex with bound c[G(2', 5')pA(3',5')p]. (D) Two alternate views of the bound product cGAMP in the catalytic pocket of the ternary complex. Note that the bound ligand c[G(2',5')pA(3',5')p]revealed a 2',5' phosphodiester linkage within the GpA step. Based on HPLC comparison, the structure of c[G(2',5')pA(3',5')p] is shown with a 3',5' linkage at the ApG step. Both G and A residues adopt anti alignments at their glycosidic bonds. (E) Two alternate views of the Fo-Fc omit electron density map contoured at 3.00 of bound c[G(2',5')pA(3',5')p] in the catalytic pocket of the ternary complex. (F) Two alternate views of the superposed structures of bound c[G(2',5')pA (3',5')p] (gray) and ATP (dark gray) in their respective ternary complexes with cGAS and dsDNA.
Figure 12:
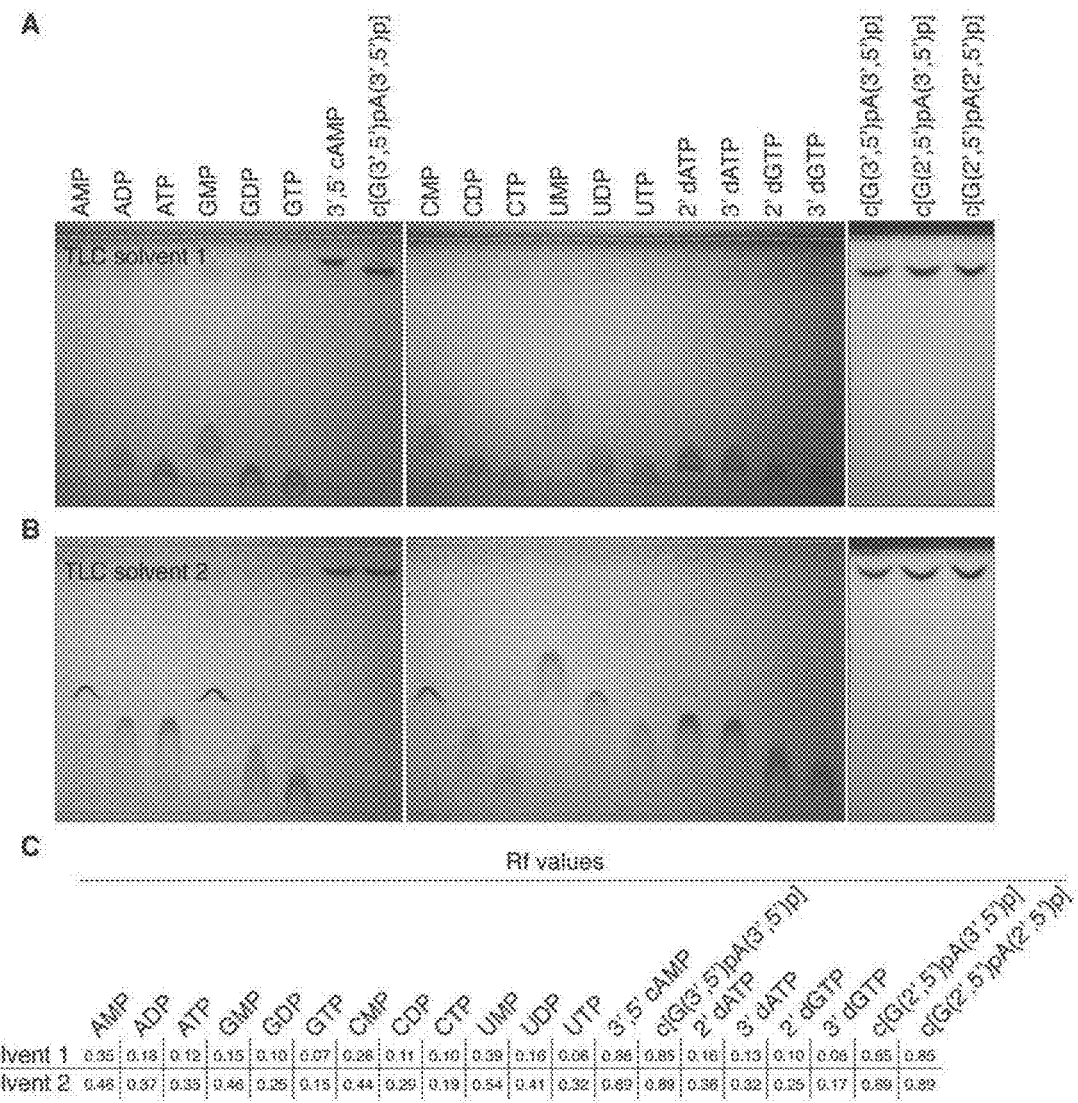
FIG. 12, comprising panels A-C, shows Thin-layer Chromatography (TLC) Conditions for Monitoring Formation of Cgamp. (A, B) Indicated nucleotides were spotted on high-performance silica gel TLC plates, resolved by various solvent systems, and visualized by UV. Two mobile phase conditions were used (A and B). Solvent system 1 was used in the majority of experiments for detection of c[G(2',5')pA (3',5')p], whereas solvent 2 was used for a better separation of the mono and tri-phosphorylated linear intermediates. Dashed lines indicate the solvent fronts. (C) Calculated Rf values.

Importantly, we can trace the GpA step in the bound cyclic dinucleotide without ambiguity (the 3'-OH of G can be traced) and establish that this linkage is 2',5' (FIG. 11D). On the other hand, the linkage at the ApG step in the bound cyclic dinucleotide could be either 2',5' or 3',5' based on the observed density, and cannot be assigned with certainty solely based on structure. We have undertaken the refinement with a 3',5' linkage at the ApG step based on evidence outlined later and prepared the drawings in FIGS. 4 and 11 with 2',5' linkage at the GpA step and 3',5' linkage at the ApG step. We can distinguish G from A based on the observed density for the 2-amino group of G, and note that both adopt anti alignments in the bound cyclic dinucleotide {c[G(2',5') pA(3',5')p]} (FIG. 11D). The A residue of the bound c[G(2', 5')pA(3',5')p] is stacked on Tyr421 (FIG. 4B, C), while the G residue of the bound c[G(2',5')pA(3',5')p] is anchored in place through hydrogen bonding to the side chains of Asp213, Asp307 and Arg364 (FIG. 4B,C). Further, the A and G residues partially stack on each other. The 2Fo-Fc electron density for the bound c[G(2',5')pA(3',5')p] is shown in FIG. 4D, with omit maps shown in FIG. 11E. A view of the bound c[G(2',5')pA(3',5')p] looking into the catalytic pocket of the ternary complex is shown in FIG. 4E, with the c[G(2',5')pA (3',5')p]bound towards one end of the opening. We also do not observe bound cations, given that c[G(2',5')pA(3',5')p] does not contain triphosphates, and the G base directly coordinates with Asp213 and Asp307 (FIG. 4C). We have superposed the structures of bound c[G(2',5')pA(3',5')p] and ATP in their respective ternary complexes with cGAS and dsDNA, and observe that the A of the bound c[G(2',5')pA (3',5')p] is positioned in the plane of the bound ATP (FIG. 11F).

A view of c[G(2',5')pA(3',5')p] highlighting the 2',5' linkage at the GpA step and the 3',5' linkage at the ApG step is shown in FIG. 4F. We note that in the ternary complex with 5'-pG(2',5')pA linear product, it is the G base that stacks on Tyr421 (FIGS. 3G and 4G), while in the ternary complex with c[G(2',5')pA(3',5')p] product, it is the A base that stacks on Tyr421 (FIG. 4C, H). Thus, the linear product and cyclic final product adopt different alignments within the catalytic pocket.

Example 2

Biochemical Characterization of cGAS Activity

Figure 5:
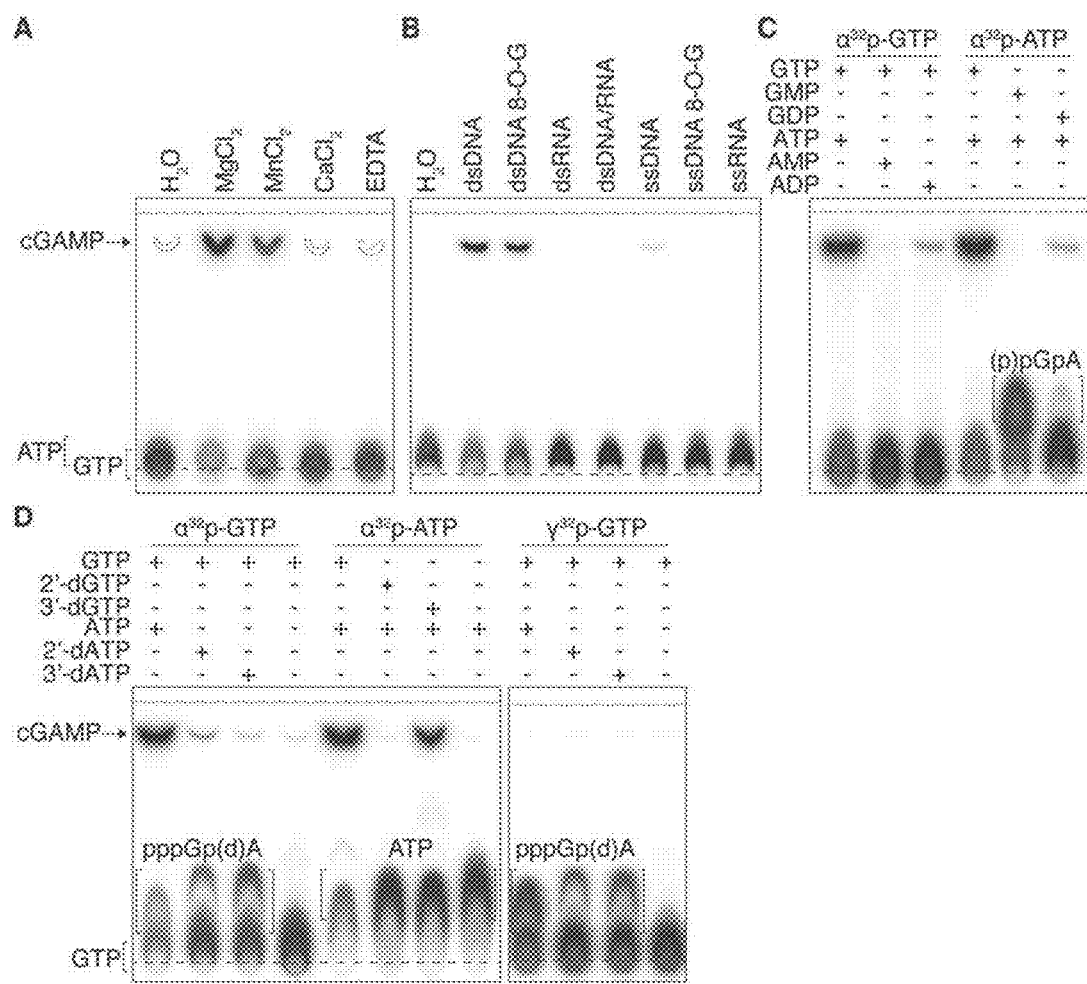
FIG. 5, comprising panels A-D, shows Characterization of c[G(2',5')pA(3',5')p] Formation by cGAS. Generation of c[G(2',5')pA(3',5')p] and linear products and intermediates were assayed by thin-layer chromatography (TLC) using purified recombinant truncated (A panel, amino acids 147-507, used in crystallization studies) and full-length cGAS (B-D panels, amino acids 1-507). Long- and short-dashed lines indicate the origin and solvent fronts, respectively. (A) A 45-nt dsDNA was incubated with cGAS (x-y) in reaction buffer containing indicated divalent cation (or EDTA) and $\alpha^{32}$p-ATP and -GTP. Chemically synthesized cGAMP containing both 3',5' linkages was co-spotted in every sample and its migration, visualized by UV, is indicated (dashed outlines). (B) cGAS was incubated with single (ss) or double (ds) stranded DNA, RNA, DNA/RNA duplex, or 8-oxoguanine (8-O-G) modified DNA of similar sequence and c[G(2',5')pA(3',5')p] formation was monitored using $\alpha^{32}$p-ATP. (C) Mono- and di-phosphorylated adenosine and guanosine were used as substrates to determine order of c[G(2',5')pA(3',5')p] formation. Slow-migrating 2',5'-linked intermediate species when cGAS and dsDNA is incubated with $\alpha^{32}$p-ATP and GMP (5'-pGpA) or GDP (5'-ppGpA). (D) dsDNA-dependent cGAMP reaction intermediates were visualized by using 2' or 3' dATP and dGTP. Slow migrating intermediate species, corresponding to pppGpA (lane 1) or pppGpdA (lanes 2 and 3), are seen by changing TLC mobile phase composition. Intermediate species were confirmed using $\gamma^{32}$p-GTP.

To validate the structural results, we established an activity assay using thin-layer chromatography (FIG. 11) and monitored cyclic dinucleotide c[G(2',5')pA(3',5')p] formation from ATP and GTP using purified recombinant full-length and truncated cGAS proteins. cGAS required the presence of dsDNA and $Mg^{2+}$ or $Mn^{2+}$ for activity (FIG. 5A-B). We tested c[G(2',5')pA(3',5')p] formation as a function of dsDNA length and found that dsDNA of 36 bp or longer were optimal, yet the 16 bp dsDNA used for crystallography elicited some activity (FIG. 13A). Double-stranded RNA, a DNA/RNA duplex, or single-stranded DNA or RNA did not stimulate cyclic dinucleotide formation (FIG. 5B). The trace amount of c[G(2',5')pA(3',5')p] detected for the specific ssDNA used in this experiment was attributable to a stretch of sequence complementarity, and the substitution of G by 8-oxoguanine (8-oxoG) was sufficient to destabilize its predicted interaction and eliminate the residual cGAS activity. Replacement of guanine by 8-oxoG within the dsDNA did not alter cGAS activity.

We quantified the activity of cGAS to yield c[G(2',5')pA(3',5')p] under multiple turnover conditions. Over 78% (s.d.+/−2.6%, n=5) of the original ATP and GTP provided was converted to c[G(2',5')pA(3',5')p] within 40 min leading to an estimated observed rate constant of 0.19 $min^{-1}$ and involving over 750 turnovers per enzyme molecule.

To determine the order of intermediate formation, we first substituted GTP by GMP or GDP (FIG. 5C). Both compounds led to the formation of the respective 5'-pG(2',5')pA product and 5'-ppG(2',5')pA intermediates, and only 5'-ppG(2',5')pA could react further to yield a reduced amount of the cyclic-dinucleotide. Substitution of ATP by ADP or AMP resulted in no product or intermediate formation, with only ADP (with GTP) leading to the generation of reduced levels of c[G(2',5')pA(3',5')p].

In order to determine the involvement of 2' or 3'-hydroxyl (OH) groups of GTP and ATP for formation of c[G(2',5')pA(3',5')p], we tested 2'- and 3'-deoxyguanosine triphosphate and 2' and 3' and deoxyadenosine triphosphate as substrates for cGAS (FIGS. 5D and 13B). 2'-dGTP was unable to form a cyclic dinucleotide, unlike 3'-dGTP, indicating that the 2'-OH of guanosine was required for the formation of the linkage with the α-phosphate at the 5' position of adenosine. In contrast, both 2'- and 3'-dATP led to markedly reduced formation of cyclic GA-dinucleotides, although 2'-dATP+GTP yielded noticeably more product. In both cases, we observed accumulation of 5'-pppG(2',5')pdA reaction intermediates (FIG. 5D, lanes 2 and 3), which migrated slightly faster than the all ribose intermediate (5'-pppG(2',5')pA, lane 1).

Example 3

Identification of c[G(2',5)pA(3',5')p] as the Product Formed by dsDNA-Dependent cGAS Activity The syntheses and purification of the three isomeric cGAMP molecules, c[G(2',5')pA(2',5')p] (2',5' linkages at GpA and ApG steps) 6, c[G(2',5')pA(3',5')p] (2',5' at GpA step and 3',5' at ApG step) 11, and c[G(3',5')pA(3',5')p] (3',5' at GpA and ApG steps) 15 shown in FIG. 14 were carried out using procedures previously reported by the Jones laboratory (Gaffney et al. 2010; Gaffney and Jones, 2012). The identity of the three isomeric cGAMP molecules 6, 11 and 15 (FIG. 14) was validated from heteronuclear NMR analysis using through-bond connectivities. The experimental NMR data for c[G(2',5')pA(3',5')p] is outlined in FIG. 15, with the proton and carbon chemical shifts for all three isomeric GMP molecules listed in Table S4.

Figure 6:
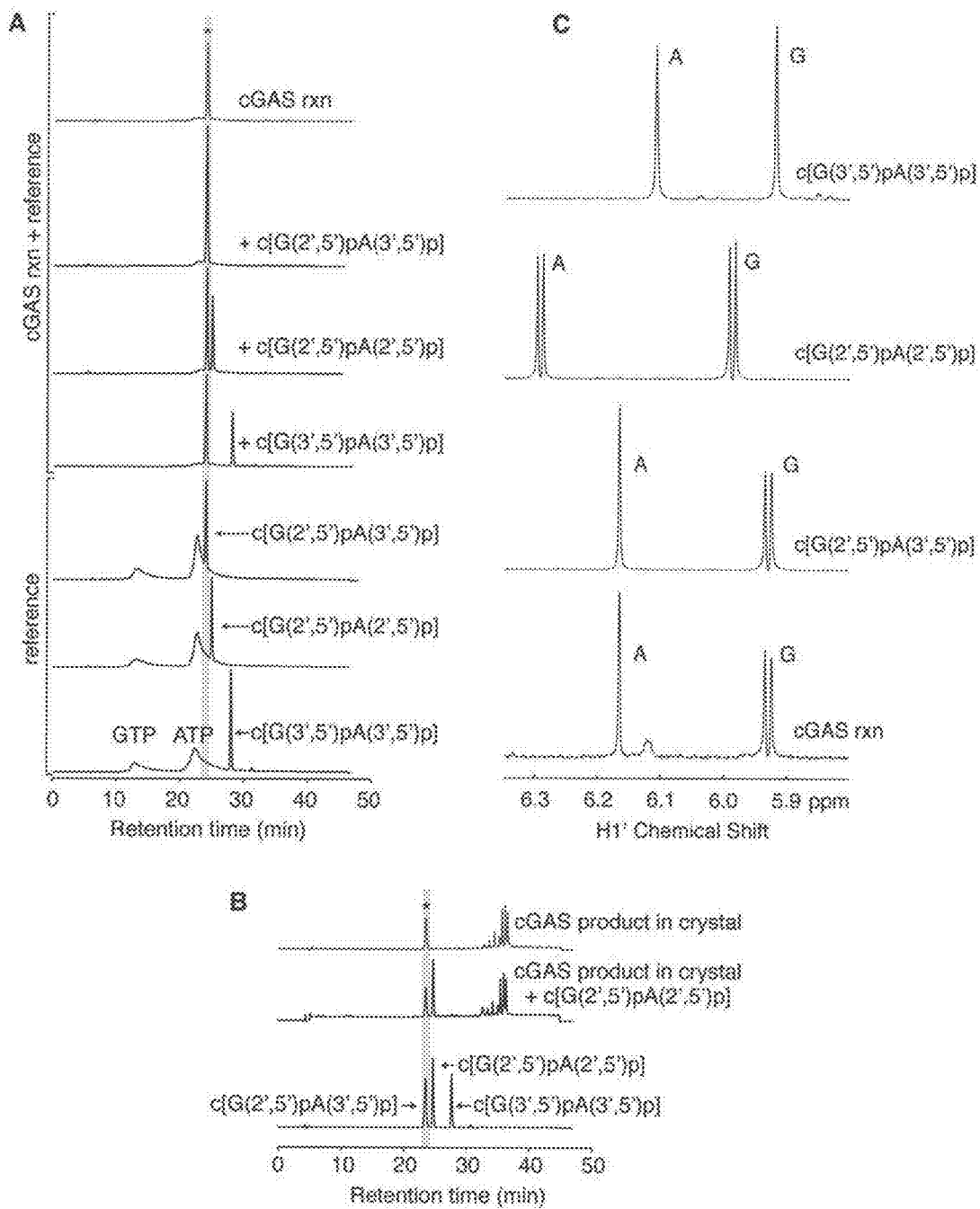
FIG. 6, comprising panels A-C, shows Definitive Identification of c[G(2',5')pA(3',5')p] as the Enzymatic Product of cGAS. (A) UV 260 nm chromatographs of GTP, ATP, c[G(2',5')pA(2',5')p], c[G(3',5')pA(3',5')p], c[G(2',5')pA(3',5')p] and cGAS reaction (rxn, asterisk) solutions from reverse-phase HPLC analyses. cGAS reaction samples were injected alone or with addition of indicated reference standards. Shaded region shows the retention time corresponding to the elution of c[G(2',5')pA(3',5')p]. (B) UV 260 nm chromatographs from HPLC analysis of the cGAS product obtained from dissolved crystals when injected alone (top trace), or co-injected with c[G(2',5')pA(2',5')p] reference compound (middle trace). Additional unidentified peaks were present in the dissolved crystal solution, but elute later. The three reference cGAMP compounds were co-injected due to a change (0.5 sec) in the retention time of c[G(2',5')pA(3',5')p] as a result of applying the dissolved crystal solution to the column. (C) NMR spectra of the sugar H1' proton region of three chemically synthesized cGAMP reference compounds with the cGAS rxn in 99.9% D$_2$O in 10 mM K$_2$HPO$_4$—KH$_2$PO$_4$ (pH 6.6) buffer. The NMR spectrum of the cGAS rxn corresponds to c[G(2',5')pA(3',5')p] reference compound. The H1' proton is a doublet ($^3J_{HH}$=9 Hz) when the phosphate is attached to the 2'-position, but a singlet when the phosphate is attached to the 3'-position, reflecting the different puckers of the five-membered sugar ring dependent on the position of the attached phosphate group.
Figure 7:
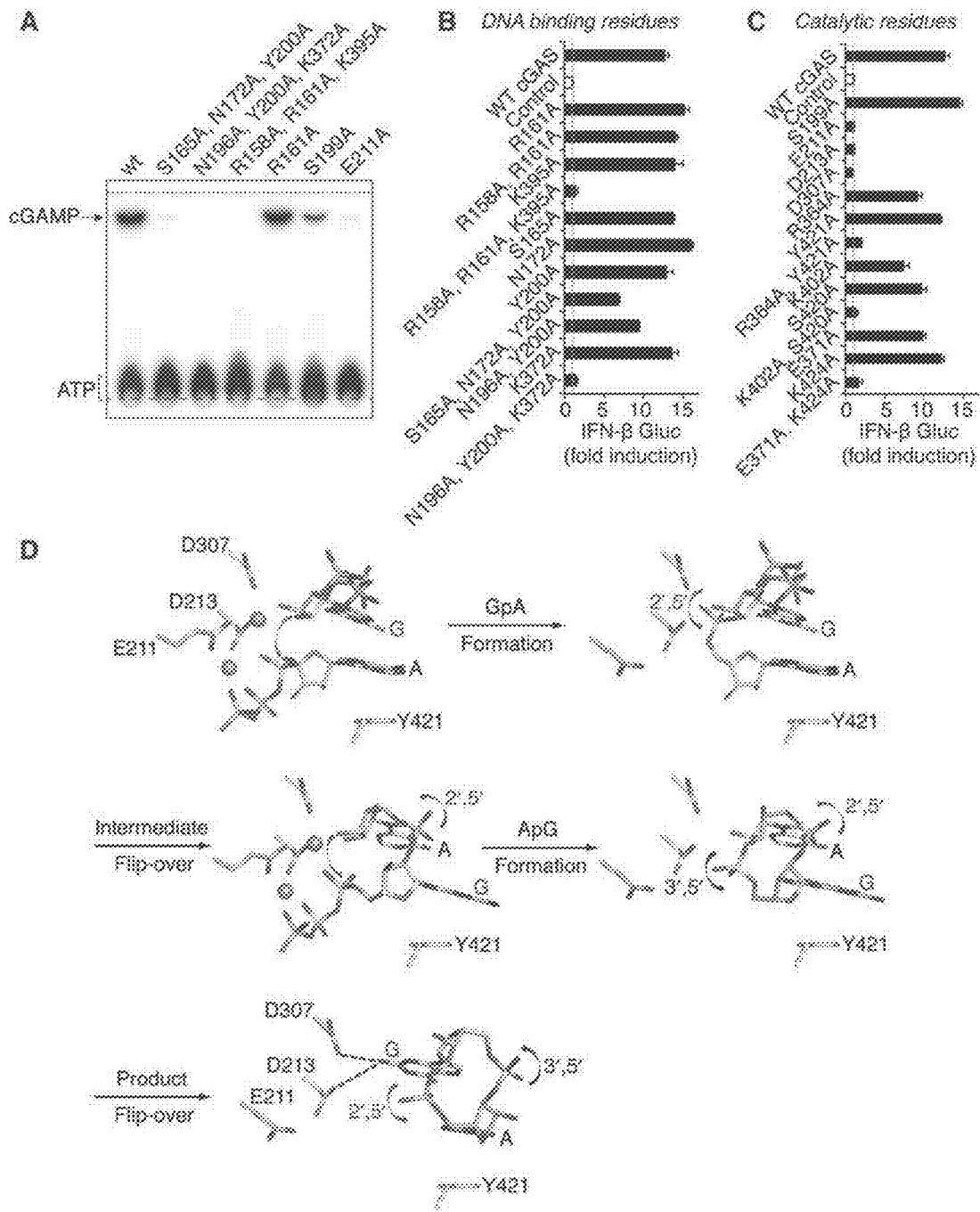
FIG. 7, comprising panels A-D, shows Functional analysis of cGAS Mutants and the Model for Two-step Generation of c[G(2',5')pA(3',5')p]. (A) Levels of c[G(2',5')pA(3',5')p] formation by cGAS full-length wt and indicated mutants were compared by TLC analysis. Long- and short-dashed lines indicate the origin and solvent fronts, respectively. (B, C) Expression vectors of murine cGAS WT, or carrying single and multiple alanine mutations of DNA binding (panel B) and catalytic (panel C) residues were transiently transfected into HEK 293 cells together with an IFN-β Gluc reporter, and constitutive STING and Firefly luc expression plasmids. In this setting expressed cGAS is engaged in the cytosol by the co-transfected DNA plasmids. Gluc values were determined in triplicate, 36 h after transfection, normalized to Firefly luc, and are shown as fold induction over control plasmid (as mean±s.e.m). Data in panels B and C are representative of 3-5 independent experiments for each mutant. (D) A schematic representation of a proposed model associated with a two-step generation of c[G(2',5')pA(3',5')p] within the single catalytic pocket of cGAS. In this model, the first step involves formation of a 5'-pppGpA intermediate followed by formation of c[G(2',5')pA(3',5')p]. Note, also that the bound ligand is believed to undergo two flip-overs on the pathway to c[G(2',5')pA(3',5')p] formation.
Figure 8A:
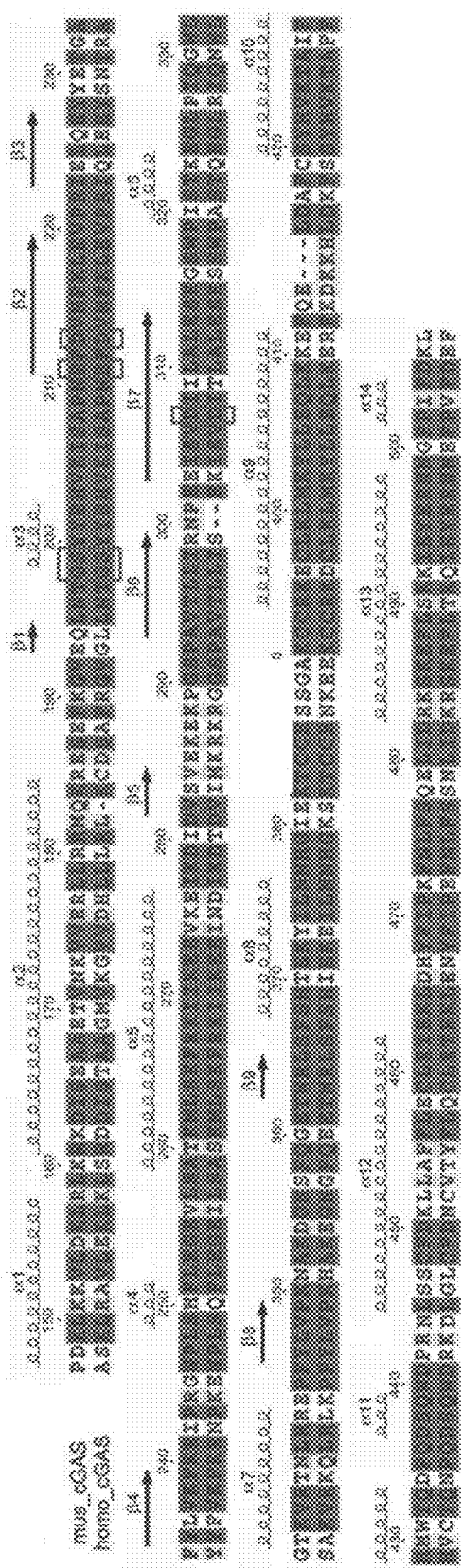
FIG. 8A-C. Sequence Alignment and Crystal Structure of cGAS in the Free State and Comparison with Human OAS1. (A) Sequence alignment of cGAS from mouse (SEQ ID NO: 53) and human (SEQ ID NO: 54) (construct used for structural studies) spanning amino acids 147 to 507 (C-terminus). The putative catalytic residues are indicated in boxes. (B) Two alternate views of the structure of cGAS in the free state. The backbone of the protein is shown in a ribbon representation and colored in light gray. (C) Stereo view of superposed structures of cGAS (light gray) and human oligoadenylate synthetase 1 (OAS1) (black; PDB: 1PX5) in the free state. The r.m.s.d between structures is 4.1 Å.
Figure 8B:
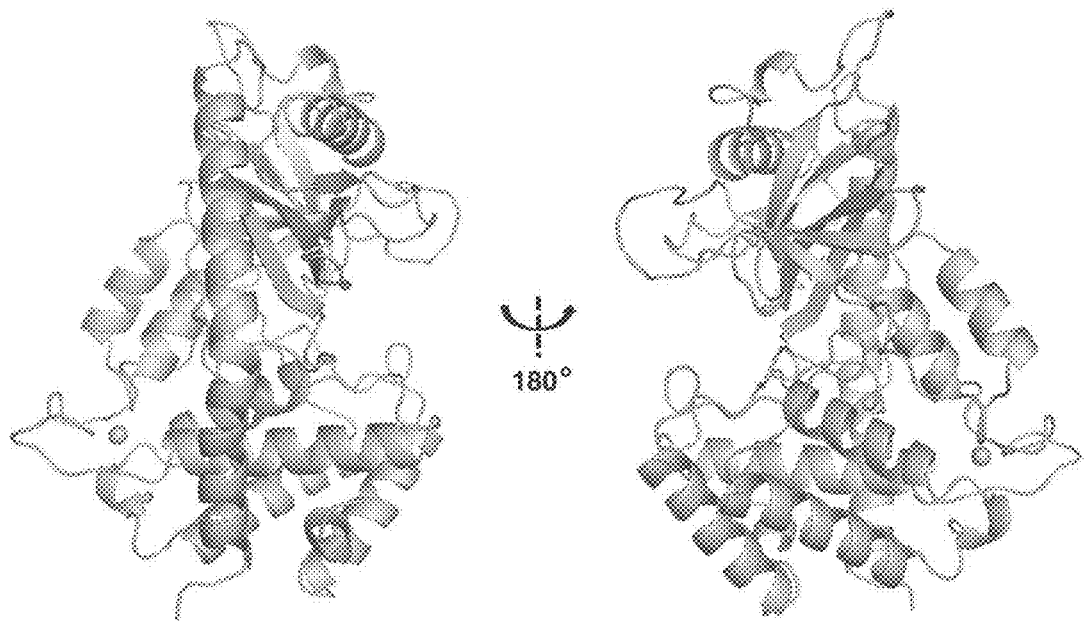
Figure 8C:
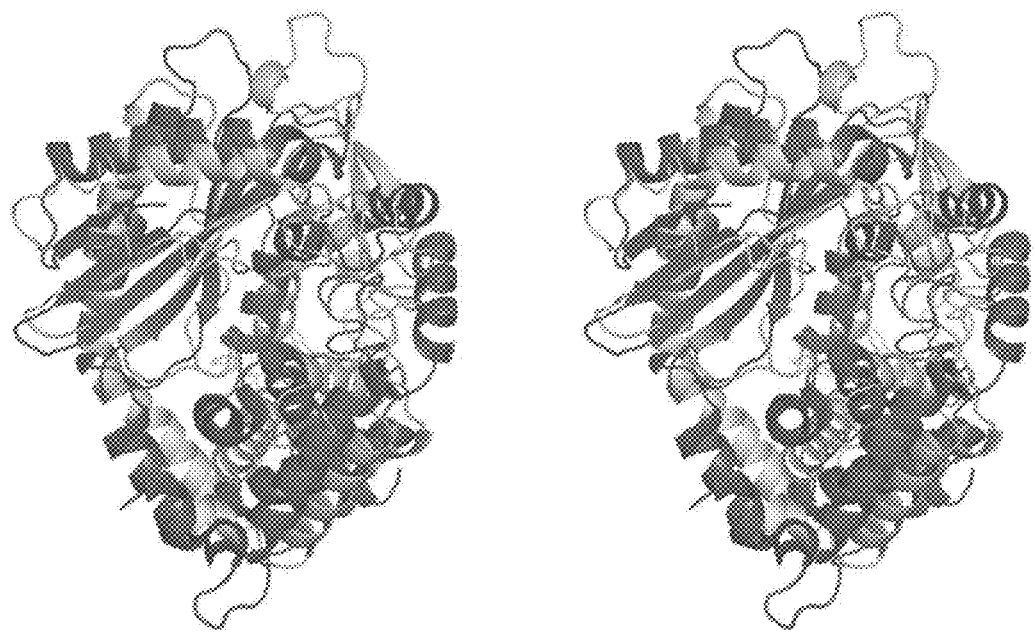
Figure 9:
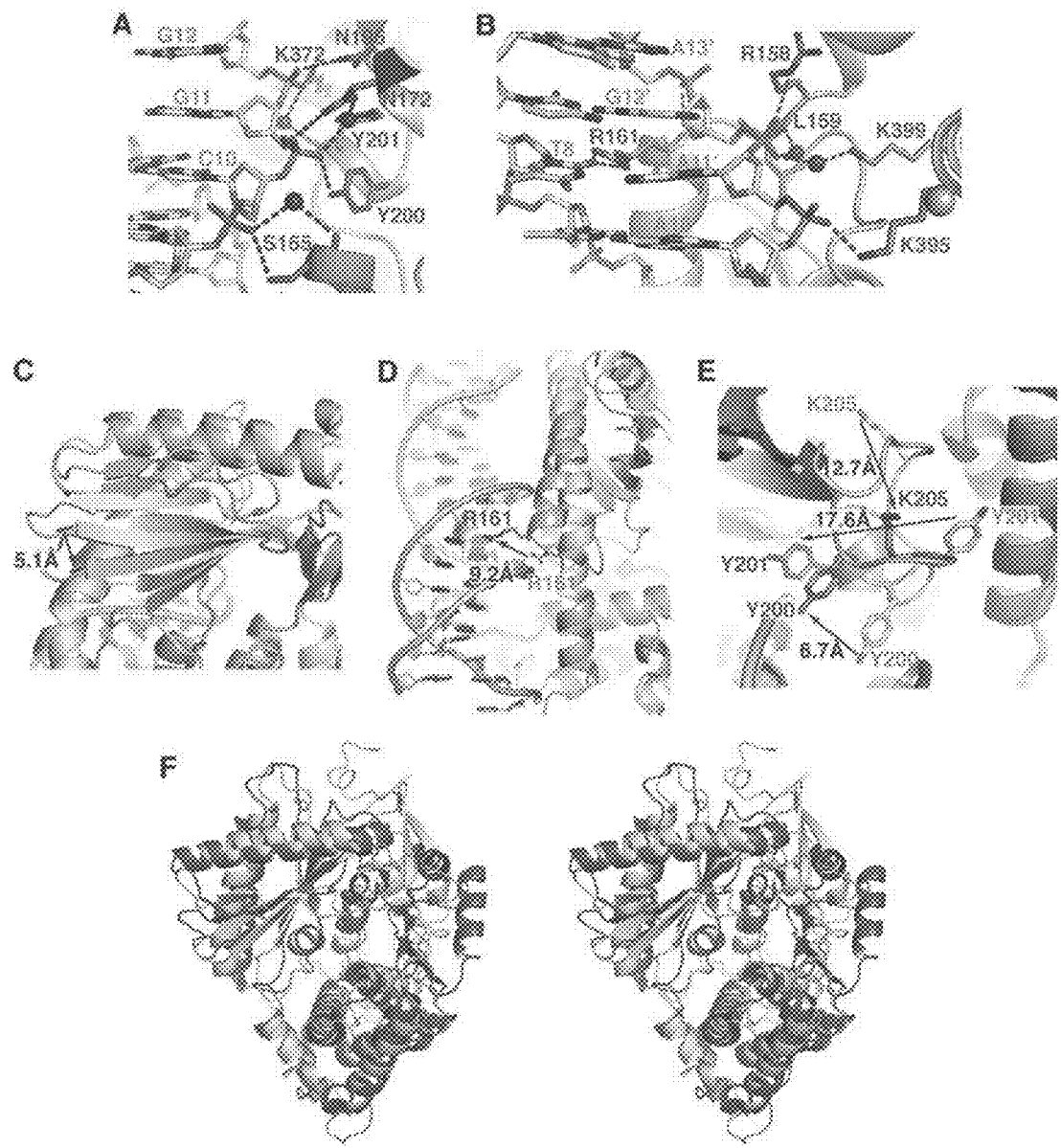
FIG. 9, comprising panels A-F, shows Molecular Recognition Features in the Structure of cGAS Bound to dsDNA and Comparison with hOAS1 Bound to dsRNA and 2'-Datp. (A, B) Examples of intermolecular contacts between cGAS and dsDNA. Water molecules are shown as black spheres, with hydrogen bonds are indicated by dashed lines. We observe one sequence-specific hydrogen bond between the side chain of Arg161 and the O2 carbonyl of T8 as shown in panel B. (C, D, E) Examples of conformational shifts on proceeding from cGAS in the free state (light gray) to the binary complex with bound dsDNA (gray). A shift of 5.1 Å is observed in the β-sheet segment on complex formation (panel C). A long α-helix breaks into two segments, with one segment moving towards the dsDNA on complex formation, including the side chain of Arg161, which moves by 9.2 Å (panel D). Several Tyr and Lys residues within loop segments shift between 6.7 and 17.6 Å on complex formation (panel E). (F) Stereo view of the superposed structures of the protein components of cGAS in the dsDNA bound state (light gray) and OAS1 in the dsRNA bound state plus 2'-dATP (black, PDB: 4IG8). The r.m.s.d between structures is 3.2 Å. The dsDNA bound to cGAS and dsRNA bound to OAS1 are omitted from depiction for clarity.
Figure 10:
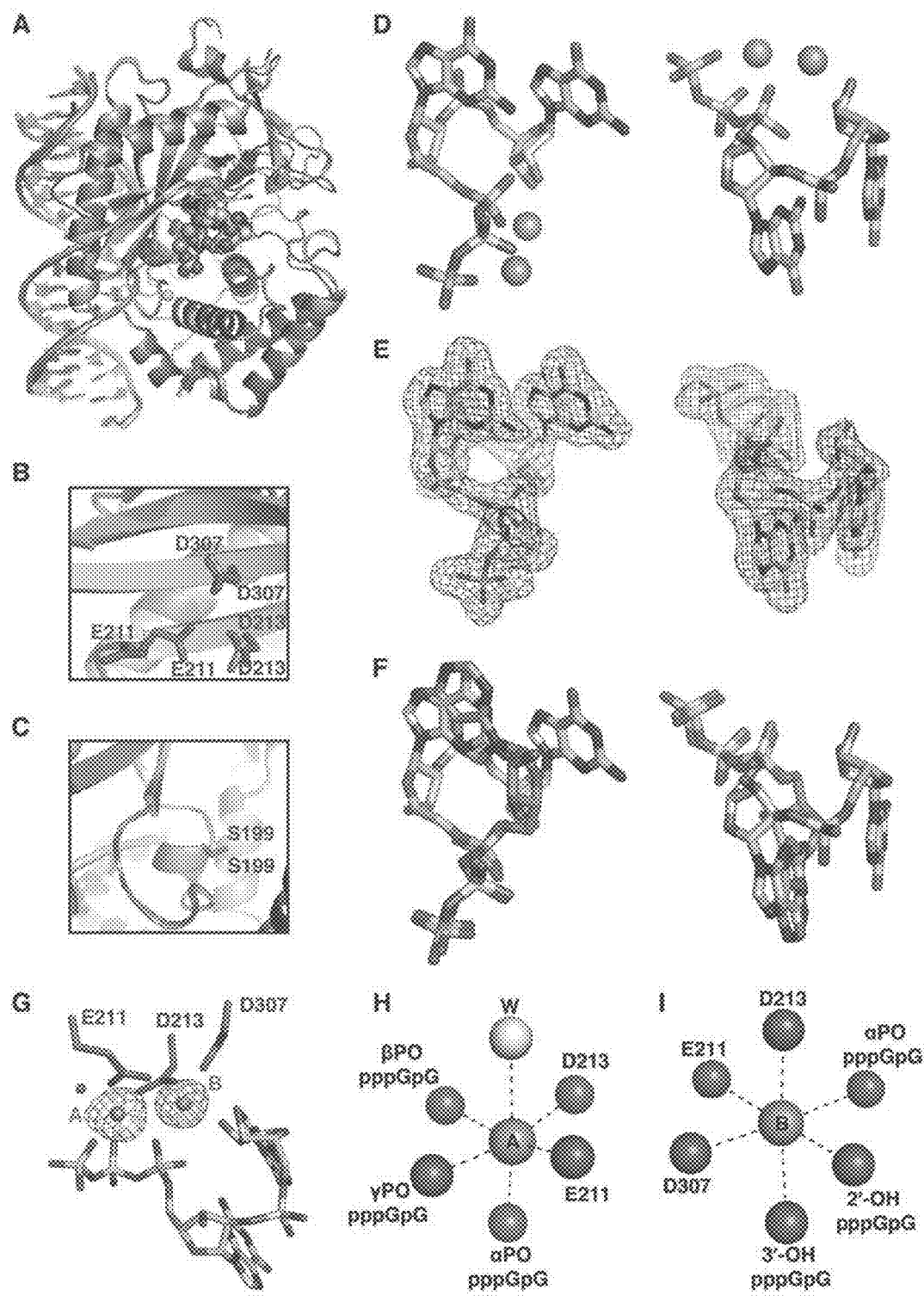
FIG. 10, comprising panels A-I, shows Structures of cGAS with 5'-pppG(2',5')pG in the Catalytic Pocket of its Ternary Complex Formed upon Crystallization with GTP. (A) Superposed structures of the binary complex of cGAS with DNA (gray) and the ternary complex with bound 5'-pppG(2',5')pG intermediate product (dark gray). (B, C) Minimal changes are observed in the backbone within the β-sheet (panel B) and catalytic pocket (panel C) segments on proceeding from the binary complex to the ternary complex with bound 5'-pppG(2',5')pG. (D) Two alternate views of the bound 5'-pppG(2',5')pG in the catalytic pocket of the ternary complex. $Mg^{2+}$ cations are shown as spheres. Note that the alignment of bound ligand is 5'-pppG(syn)p(2',5')pG(anti). (E) Two alternate views of the omit Fo-Fc omit electron density map contoured at 3.00 of bound 5'-pppG(2',5')pG in the catalytic pocket of the ternary complex. (F) Two alternate views of the superposed structures of bound 5'-pppG (2',5')pG (gray) and ATP (dark gray) in their respective ternary complexes with cGAS and dsDNA. (G) Omit map recorded at 40 identifying two bound cations in the structure of the ternary complex. (H, I) Octahedral coordination geometry around the two bound cations in the structure of the ternary complex.

We analyzed the product generated by dsDNA-dependent cGAS activity using reverse-phase high-performance liquid chromatography (HPLC) and compared its elution profile to chemically synthesized c[G(3',5')pA(3',5')p], c[G(2',5')pA(2',5')p], and c[G(2',5')pA(3',5')p] compounds (FIGS. 6A and 13D). A prominent peak consistently eluted from the HPLC system at precisely 23.5 min, which corresponded to the elution profile of c[G(2',5')pA(3',5')p]. Co-injection with c[G(3',5')pA(3',5')p] or c[G(2',5')pA(2',5')p]demonstrated that the cGAS reaction product does not co-elute, unlike co-injection with chemically synthesized c[G(2',5')pA(3',5')p].

To demonstrate that the in vitro produced cyclic dinucleotide matched the molecule determined crystallographically, we analyzed by HPLC the dissolved cGAS crystals that had been co-incubated with DNA, ATP, and GTP (FIG. 6B). A peak corresponding to c[G(2',5')pA(3',5')p] was observed, distinct from the c[G(2',5')pA(2',5')p] co-injected reference molecule as before. Additional unidentified peaks of longer retention times were also seen. Presumably, these unidentified compounds originating from the crystallization buffer and/or additives were not completely removed despite washing the crystals prior to HPLC analysis.

In addition, cGAS-generated c[G(2',5')pA(3',5')p] was purified by HPLC and subjected to one-dimensional NMR analysis. Its NMR spectrum in the sugar H1' region is identical to that of chemically synthesized standard c[G(2',5')pA(3',5')p] and distinct from chemically synthesized c[G(2',5')pA(2',5')p] and c[G(3',5')pA(3',5')p] (FIG. 6C). Thus, both HPLC (FIG. 6A) and NMR (FIG. 6C) independently validate that the product generated by cGAS is c[G(2',5')pA(3',5')p].

Example 4

Functional Analysis of cGAS Mutant Proteins

We next assayed the biochemical and functional consequences of mutations on cGAS in its capacity to form c[G(2',5')pA(3',5')p] in vitro and to stimulate the type I interferon pathway in cells. We generated alanine-substitution mutants corresponding to amino acid residues that the co-crystal structures revealed to be involved in dsDNA binding or cGAS activity. For in vitro cGAS activity assays, we generated and purified six recombinant mutant cGAS forms; four were predicted to eliminate dsDNA-binding and two point mutant proteins were substituted with alanine at potentially key catalytic residues. Incubation of DNA with mutant cGAS proteins led to little or no c[G(2',5')pA(3',5')p] formation for all but two mutants (R161A, S199A, FIG. 7A).

To assess the impact on cGAS function in cells, we generated additional alanine mutants of cGAS for expression in mammalian cells. The full-length cGAS mutants together with STING and an IFN-β luciferase reporter were transiently expressed in HEK 293 cells. In this assay cGAS is engaged by the co-transfected DNA plasmids, and WT cGAS expression resulted in close to 15-fold enhanced luciferase activity compared to a control plasmid (FIG. 7B). Single mutations of DNA binding residues, including Arg161 responsible for the only direct interaction with a DNA base, were not sufficient to impair cGAS activity. However, ablation of interactions with two or three consecutive phosphodiesters in either DNA strand (FIG. 1C, 9B-C) resulted in diminished, or entirely abrogated cGAS function (FIG. 7B). At the catalytic site, single mutants Glu211, Asp213 or Asp307 affecting the binding of divalent cations (FIG. 2E, 3B) all resulted in non-functional cGAS (FIG. 7C). Furthermore, abrogation of cGAS activity required mutation of both amino acid residues involved in (i) the binding of ATP (or GTP) gamma phosphate (Lys402, Ser420; FIG. 2E, 3B), (ii) the binding of ATP adenosine (Glu371, Lys424; FIG. 2F), or (iii) the base stacking of ATP and c[G(2',5')pA(3',5')p] (Arg364, Tyr 421; FIG. 2F, 4B), while single mutants of these residues only slightly impaired cGAS function (FIG. 7C). Gly198 and Ser199 are highly conserved residues that were found to undergo significant conformational changes upon ligand binding (FIG. 1F, 2D). Nevertheless, single mutations G198A and S199A did not severely impair cGAS function, but the double mutant of these positions was not functional (FIG. 13E). Similarly, conversion of the highly mobile Gly198 to sterically restricted proline abrogated cGAS activity (FIG. 13E).

Example 5

Studies on Conformational Transitions, Bond Formation, and Intermediates Conformational Transitions in cGAS on Complex Formation Our structural studies highlight the fact that cGAS undergoes a pronounced conformational change upon binding of dsDNA (FIG. 1D), whereby it repositions catalytic residues Glu211, Asp213, Asp307, as well as Ser199 (FIG. 1E, F), while at the same time opening access to the catalytic pocket (FIG. 1G, H). In essence, cGAS adopts a catalytically competent conformation only when engaging dsDNA, thereby accounting for its role as a cytosolic dsDNA sensor. By contrast, only minimal conformational changes that are restricted to the side chain of Glu211 are observed when proceeding from the binary complex of cGAS and dsDNA to the ternary complex with ATP (FIG. 2B-D) and GTP (where the pocket contains off-pathway intermediate 5'-pppG(2',5')G; FIG. 10A-C), with no change observed even for the side chain of Glu211 on formation of the ternary complex with ATP+GTP (where the pocket contains product c[G(2',5')pA(3',5')p]; FIG. 11A-C).

Phosphodiester Bond Formation in Catalytic Pocket

The structural and functional experiments both established phosphodiester bond formation in the catalytic pocket after binding of dsDNA to cGAS, in the absence of any additional components. The structural studies on cGAS in the presence of dsDNA and GTP identified accumulation of linear reaction intermediate 5'-pppG(2',5')pG (FIG. 3B,C), while in the presence GMP and ATP identified accumulation of linear reaction product 5'-pG(2',5')pA. While not wishing to be bound by any particular theory, it is believed that the former intermediate is off-pathway and therefore impaired for the formation of the second phosphodiester bond to form a cyclic product, given that the first G is syn, and the distance is long between the 2'-OH (or 3'-OH) of the second G and the α-phosphate of the triphosphate moiety. Nevertheless, these results suggest that formation of c[G(2',5')pA(3',5')p] is likely to occur in a stepwise manner, involving formation of sequential phosphodiester bonds to yield the cyclic dinucleotide product. By contrast, structural studies on cGAS in the presence of dsDNA, GTP, and ATP resulted in formation of c[G(2',5')pA(3',5')p] (FIG. 4B, C), without accumulation of an intermediate and consistent with an on-pathway reaction involving formation of a pair of sequential phosphodiester linkages.

Positioning of G and a Residues of Bound c[G(2',5)pA(3',5)p]

The G and A residues of c[G(2',5')pA(3',5')p] adopt distinct positions in the structure of the ternary complex with cGAS and dsDNA. The A residue of the bound c[G(2',5') pA(3',5')p] is stacked on Tyr421 (FIG. 4B) and occupies the position of the adenine ring in the ATP complex (FIG. 2F) and the first base in the 5'-pppG(2',5')pG (FIG. 3C) and 5'-pG(2',5')pA (FIG. 3G) complexes. The A residue of bound c[G(2',5')pA(3',5')p] is not involved in any intermolecular hydrogen bonds and hence could potentially be replaced by even a pyrimidine (C or U) residue. By contrast, the G residue of bound c[G(2',5')pA(3',5')p], which is partially stacked over the A residue, forms a network of intermolecular hydrogen bonds involving its Watson-Crick and Hoogsteen edges (FIG. 4B, C) and cannot be replaced by any of the other three bases (C, A and U). Thus, the cGAS-binding pocket has distinct recognition elements that distinguish between G and A and hence can bind c[G(2',5')pA(3',5')p] in a unique orientation.

In agreement with the crystallographic data, the biochemical results indicate a strong preference for GTP, consistent with the elaborate amino acid interactions observed in the structure between cGAS and this base. Incubation of cGAS with GTP alone, as well as GTP plus either CTP or UTP, can lead to cyclical dinucleotide formation (FIG. 13C). While ATP alone does not yield any cyclic or intermediate products, incubation with UTP results in some cyclic product formation, suggesting that UTP can also substitute for GTP albeit at a much reduced reaction rate. Together, these findings indicate that cGAS has more relaxed requirements for the second nucleotide compared to the first guanosine.

Structural Comparison of Linear 5'-pG(2',5)pA and Cyclic c[G(2',5)pA (3',5')p] Product We observe a striking difference in alignment within the catalytic pocket between the off-pathway linear 5'-pG(syn) (2',5')pA(anti) product (FIG. 3F, G) and cyclic 5'-pG(anti) (2',5')A(anti) product (FIG. 4B, C). In the former case, it is the G base that stacks over Tyr421 (FIG. 3G), while in the latter it is the A base that stacks over Tyr421 (FIG. 4C). The two alignments are compared in stereo where the linear 5'-pG(2',5')pA is shown in FIG. 4G and the cyclic c[G(2', 5')pA(3',5')p] in FIG. 4H. This implies that the intermediate may have to rearrange its orientation by a complete flip-over within the catalytic pocket prior to the cyclization reaction. This may not be too surprising since judging from the three basic (Glu211, Asp213 and Asp307) and one polar (Ser199) amino acid lining the catalytic pocket, there is only a single set of catalytic residues and hence following the first phosphodiester bond formation, the intermediate may have to realign so as to facilitate the second phosphodiester bond formation to complete cyclization.

Phosphodiester Linkages

A clear assumption in the earlier studies leading to the identification of cyclic GAMP as a second messenger generated by the cytoplasmic dsDNA sensor cGAS (Sun et al. 2013; Wu et al. 2013) was that both phosphodiester linkages were of a 3',5' nature. Such 3',5' linkages have been observed previously in structures of bacterial second messenger c-di-GMP bound to both STING (Yin et al 2010; Ouyang et al. 2012; Huang et al. 2012; Shu et al. 2012) and riboswitches (Smith et al. 2009; Kulshina et al. 2009). Nevertheless, the mass spectroscopic approach utilized (Wu et al. 2013) cannot distinguish between 3',5' and 2',5' linkages for one or both phosphodiester bonds of cyclic GAMP.

The first indication of a 2',5' linkage emerged from the structure of cGAS, dsDNA and GTP, where an off-pathway product formed in the catalytic pocket, exhibited a 5'-pppG (2',5')pG linkage (FIG. 3B, C). In addition, pG(2',5')pA was observed in the structure of cGAS, dsDNA and GMP+ATP (FIG. 3F, G). More importantly, a 2',5' linkage was also observed for the GpA step of the bound c[G(2',5')pA(3',5')p] product in the catalytic pocket in the structure of cGAS, dsDNA and GTP+ATP (FIG. 4B, C).

Figure 13:
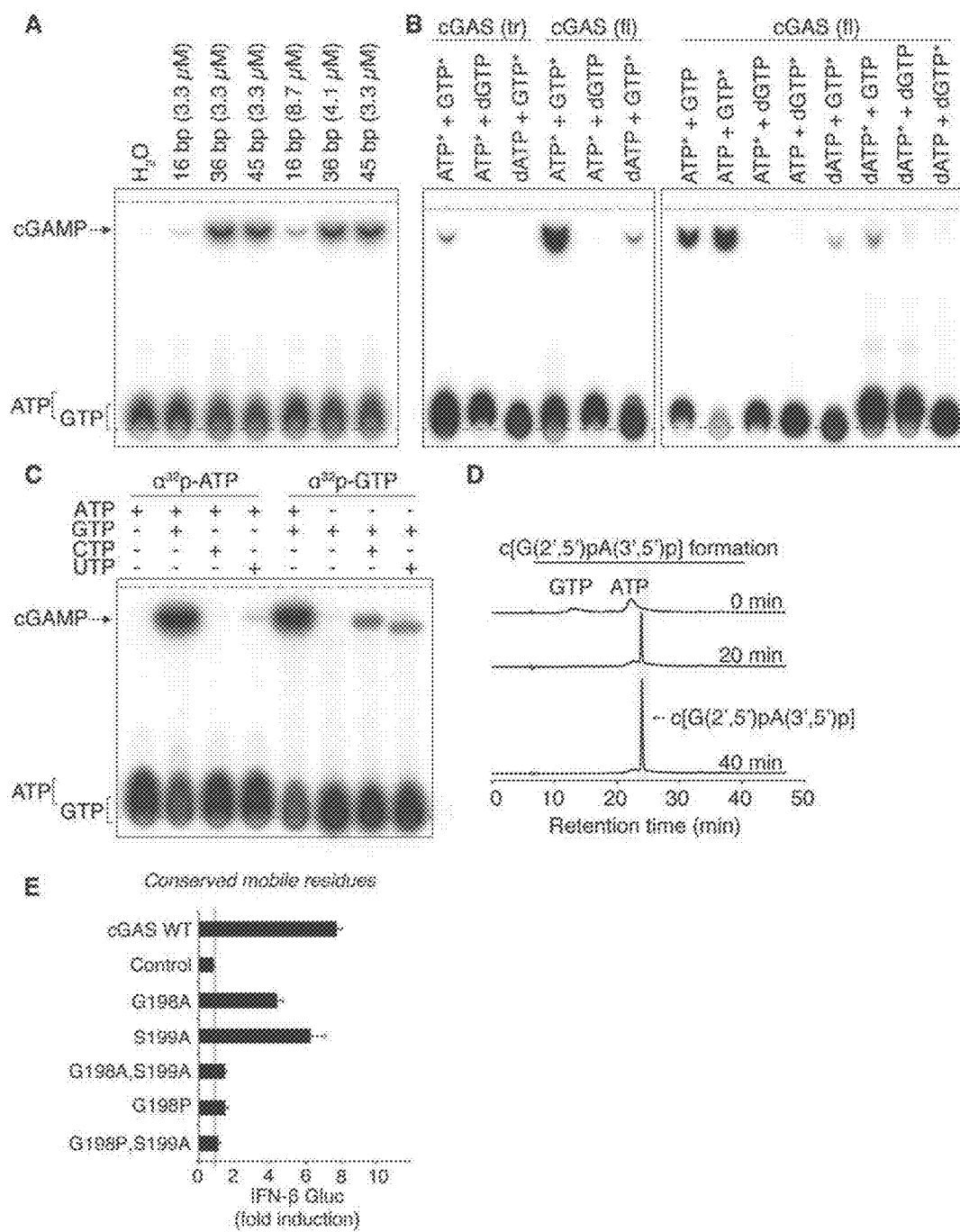
FIG. 13, comprising panels A-E, shows dsDNA-length and Nucleotide Requirements of cGAS Activity. (A) Full-length cGAS was incubated with equimolar or mass-normalized quantities of 16-, 36-, or 45-nt dsDNA then assayed for cGAMP formation. Long- and short-dashed lines in panels A-C, indicate the origin and solvent fronts, respectively. (B) Truncated (tr) and full-length (fl) cGAS was incubated with 45 bp dsDNA in reaction buffer containing the various indicated nucleotides. cGAS (tr) exhibits activity, albeit less than cGAS (fl). c[G(2',5')pA(3',5')p] forms using 2'-dATP, when 2'-dATP or GTP was radiolabelled, but not at all when 2'-dGTP was used. 2'-dATP with 2'-dGTP yielded no c[G(2',5')pA(3',5')p], indicating that blockage of the 2' OH positions in adenosine, and more importantly guanosine, prevented c[G(2',5')pA(3',5')p] production. Asterisks (*) denote which nucleotides were supplemented with an $\alpha^{32}$p-radiolabelled form. dNTP indicates the triphosphorylated 2'-deoxynucleotide. (C) Full-length cGAS was incubated in reaction buffer containing dsDNA and the indicated combination of ribonucleotides, then analyzed by TLC. Trace amounts of cyclic product were formed upon incubation of $\alpha^{32}$p-ATP with UTP, or $\alpha^{32}$p-GTP with GTP, CTP, and UTP. Optimal product formation requires GTP and ATP. The low level of cyclic product formation with UTP and ATP, but no ATP alone, suggests that UTP can be accommodated at the GTP binding site but reduced in affinity and/or activity. The migrations of all products are consistent with formation of cyclical dinucleotides. (D) HPLC analysis of dsDNA-dependent cGAS generation of c[G(2',5')pA(3',5')p] over time. A single cGAS reaction was initiated and samples were analyzed by HPLC at indicated times. (E) Highly conserved residues G198 and S199 were mutated to alanine, or G198 to proline to reduce steric flexibility. Expression plasmids for mutant and WT cGAS were transiently transfected into HEK 293 cells together with an IFN-β Gluc reporter, and constitutive STING and Firefly luc expression plasmids. Gluc values were determined in triplicate, 36 h after transfection, normalized to Firefly luc, and are shown as fold induction over Control plasmid (as mean±s.e.m). Data are representative of 3 independent experiments for each mutant.
Figure 14A:
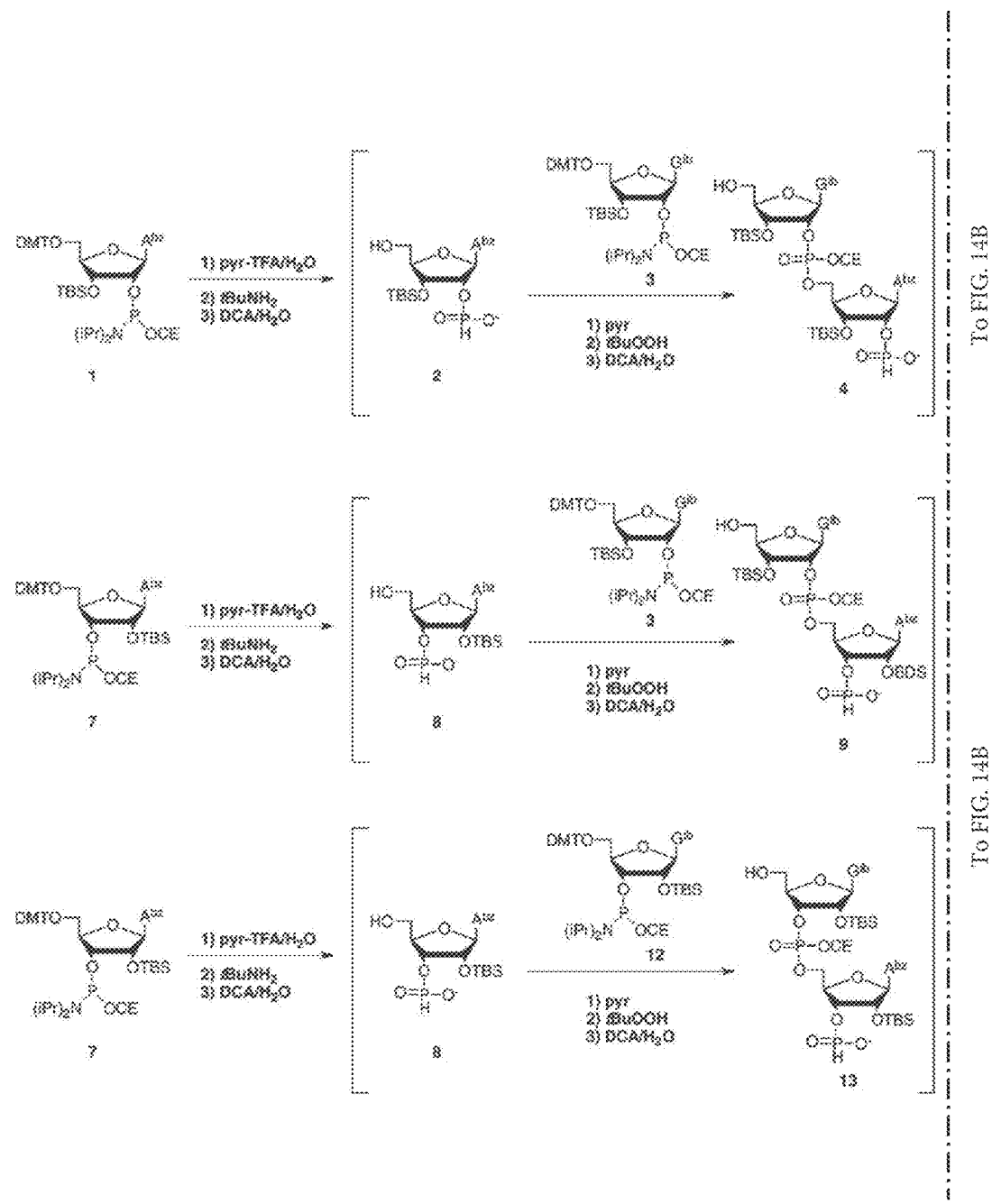
FIG. 14A-B. Syntheses of cGAMP isomers. Synthesis of cGAMP containing 2',5' linkages at both GpA and ApG steps (6) (top panel). Synthesis of cGAMP containing 2',5' at GpA step and 3',5' at ApG step (11) (middle panel). Synthesis of cGAMP containing 3',5' linkages at both GpA and ApG steps (15) (bottom panel).
Figure 14B:
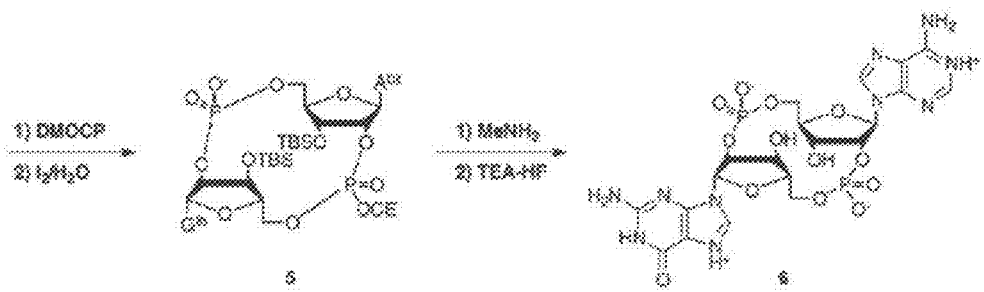
Figure 14B:
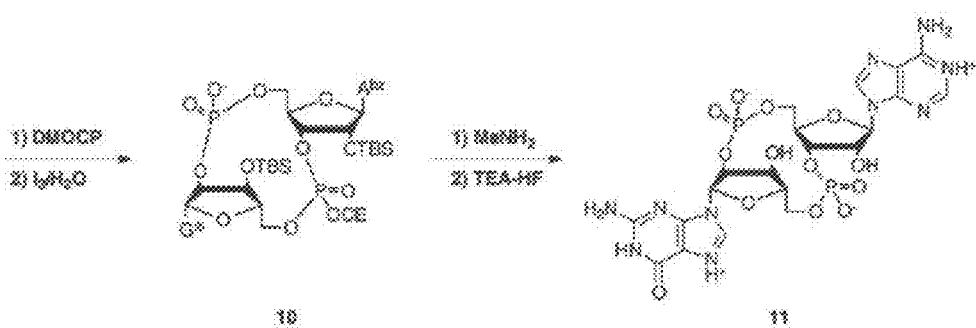
Figure 14B:
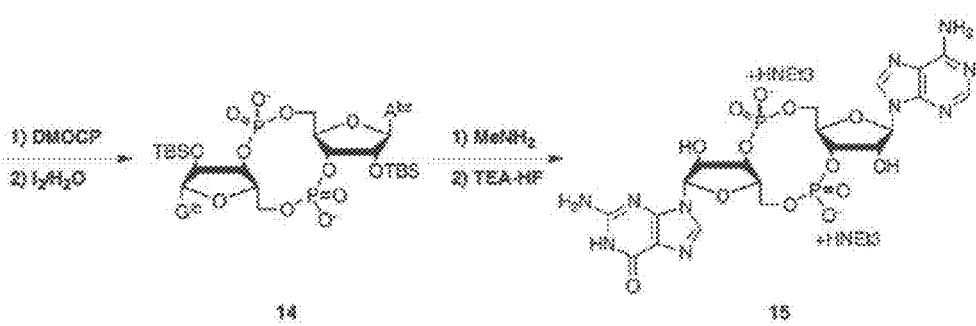
Figure 15B:
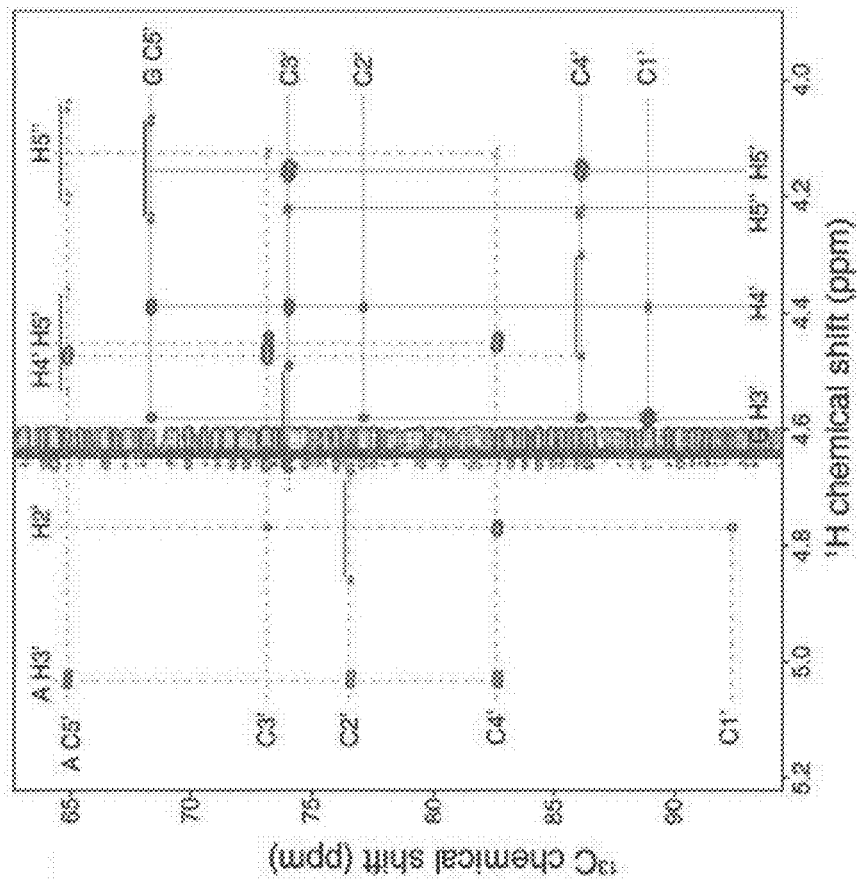
FIG. 15A-D. Resonance assignments of c[G(2',5')pA(3',5')p] from HMBC, COSY, and HSQC two-dimensional NMR spectra. (A) HMBC spectrum showing correlations between aromatics and the sugar C1'-H1'. (B) HMBC spectrum showing correlations within sugar rings. In (A) and (B), correlations within the guanine base are connected by solid lines and assignments are specified on the upper and left edges for protons and carbons respectively, while correlations within the adenine base are connected by dashed lines and assignments are specified on the lower and right edges for protons and carbons respectively; The large unsuppressed 1-bond C—H couplings are indicated by blue lines connecting the coupled pairs of signals. (C) Double quantum filtered COSY spectrum. Guanine correlations are connected by solid lines and resonances are labeled on the cross peaks above the diagonal; Adenine correlations are connected by dashed lines and resonances are labeled on the cross peaks below the diagonal. (D) Aliphatic HSQC spectrum summarizing sugar proton and carbon assignments. See also FIG. 6C and Table S4.
Figure 15A:
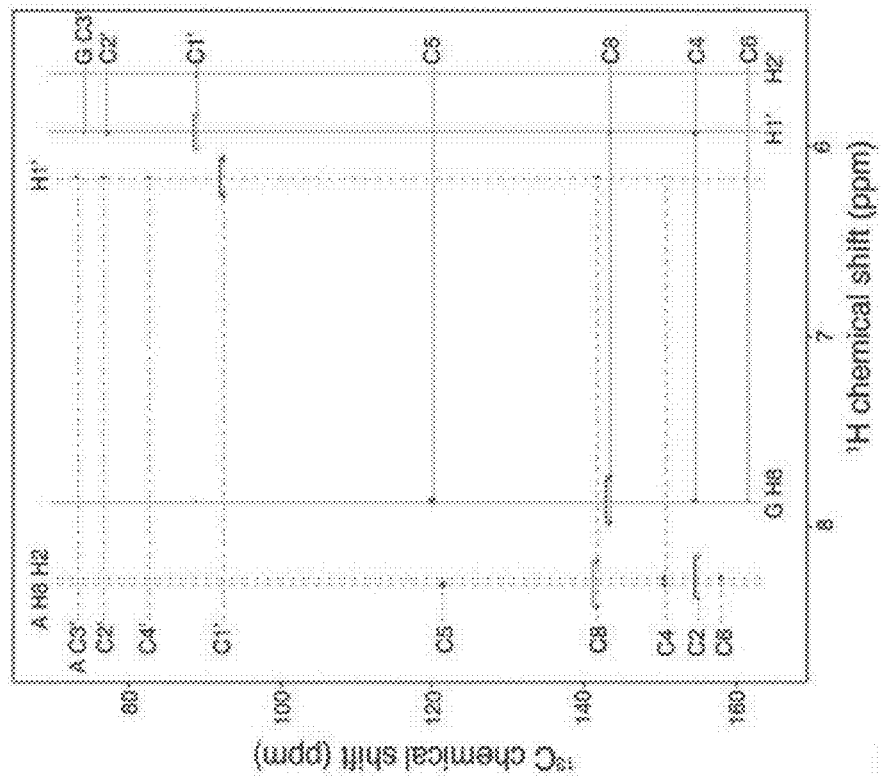
Figure 15D:
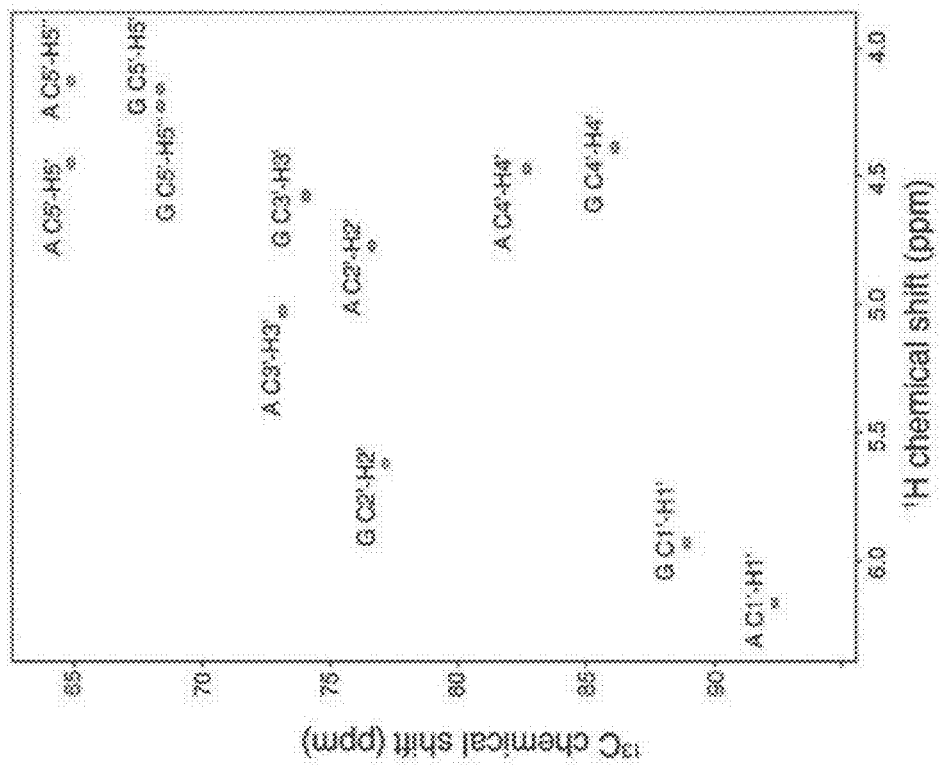
Figure 15C:
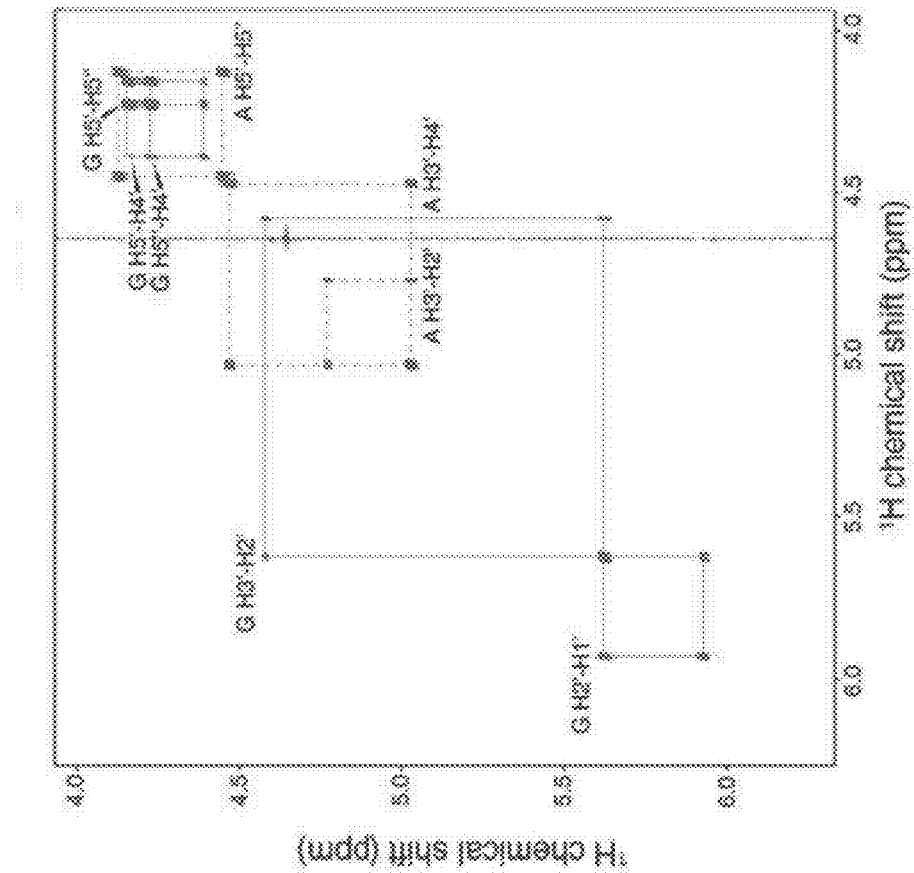
Figure 16B:
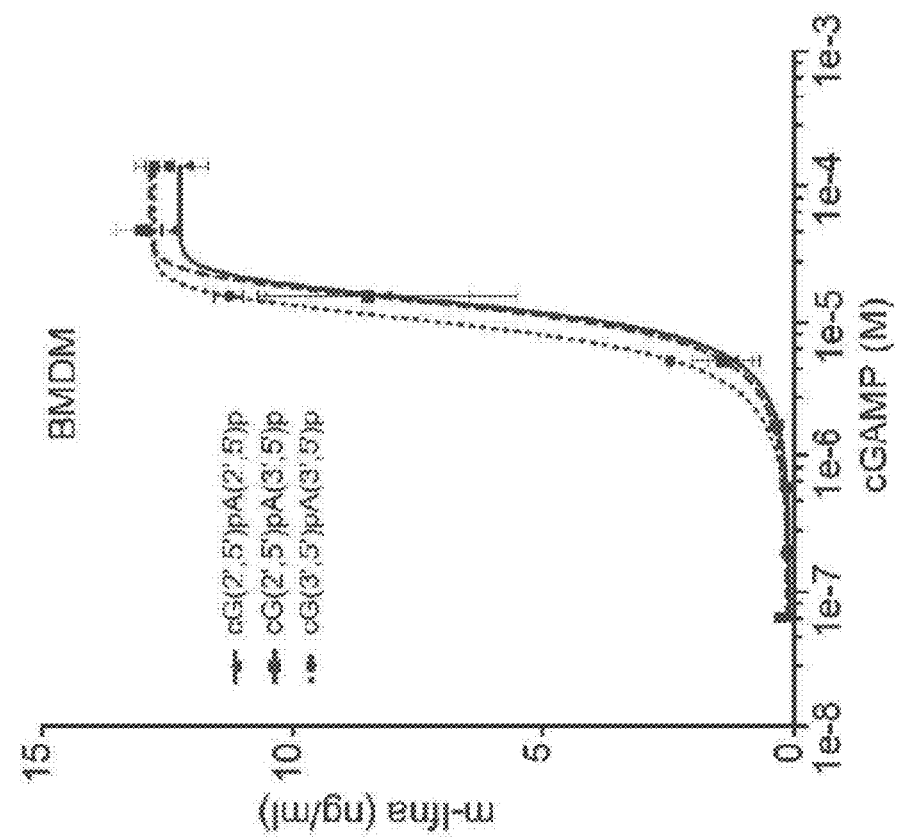
FIG. 16A-D. STING-dependent induction of murine alpha-interferon and human CXCL10 by cGAMP compounds. The dose-dependent biological activities of indicated cGAMP isomers were measured by enzyme-linked immunosorbent assay (ELISA), quantifying for the induction of endogenous murine α-interferon (m-Ifna) or human CXCL10 (h-CXCL10) proteins. (A-B), Mouse bone marrow derived macrophages (BMDM) were either treated first with Digitonin (Dig) to permeabilize plasma membranes prior to cGAMP addition (A) or cGAMP isomers were passively delivered to cells by addition in culture medium (B). (C), cGAMP activation was also measured in human THP-1 cells. Data are representative of 2 independent experiments, each done in triplicate (error bars, s.e.m.). (D), The half maximal effective concentration ($EC_{50}$) values were estimated based on 4-parametric sigmoidal dose-response curves; 95% confidence interval ranges (CI) are provided.
Figure 16A:
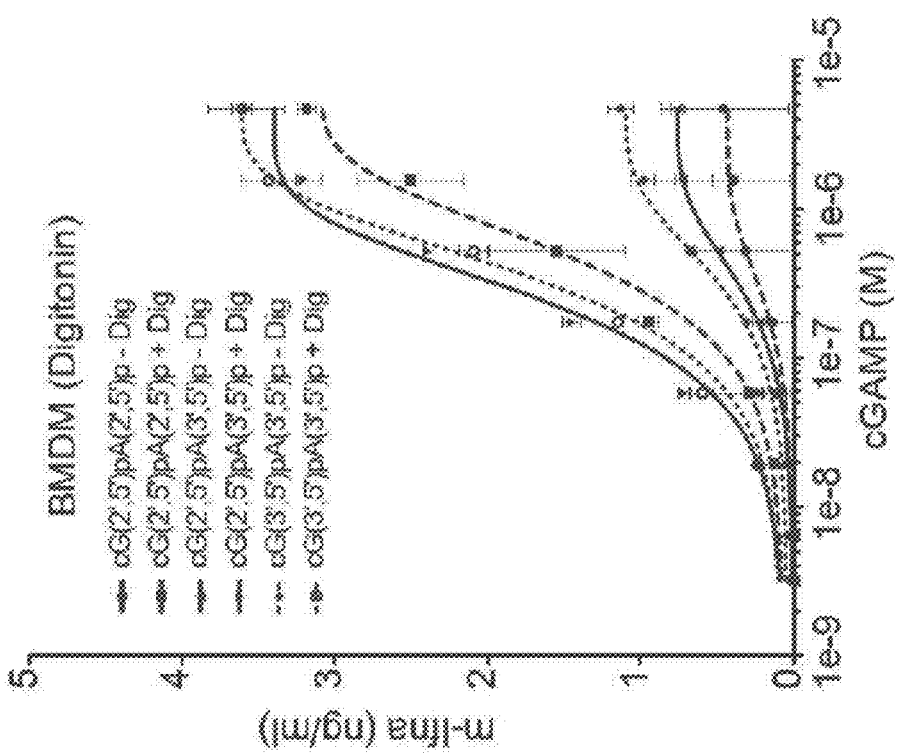
Figures 16C, 16D:
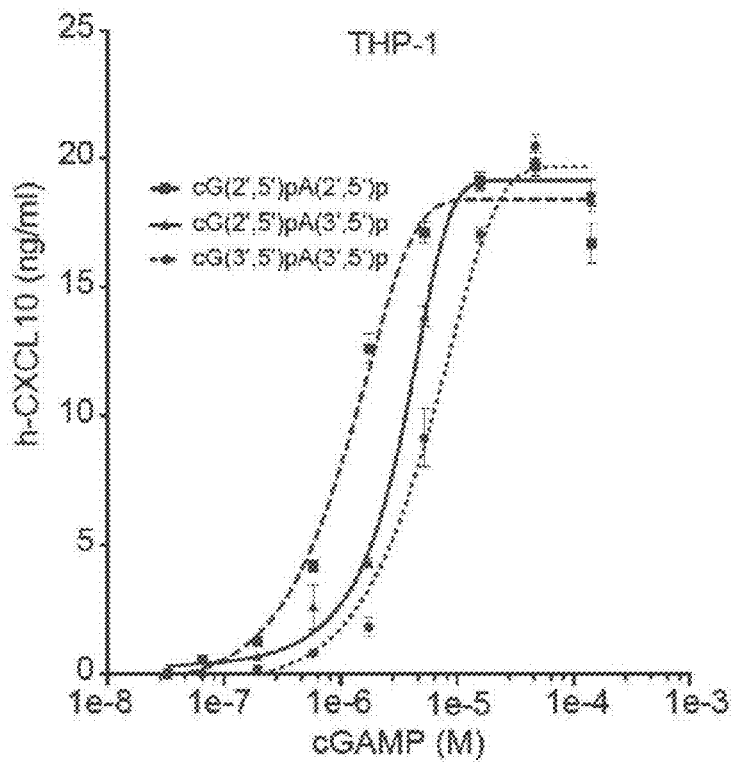

Our initial biochemical analyses indicated that the 2',5' linkage between GTP and ATP occurs first, prior to the cyclization of the adenosine back to guanosine. This evidence was further supported by the observation that incubation of 2'-dATP with 2'-dGTP could not react to form any cyclic reaction products (FIG. 13). In the second step, formation of a cyclical dinucleotide via the 2' or 3' OH of adenosine can proceed even when the other position is blocked through removal of oxygen, although there was an observable preference for utilization of 2'-dATP. Cyclic dinucleotide production in either case was very inefficient, suggesting that both positions may participate in the formation of a transition state for efficient phosphate hydrolysis and cyclization. This perplexing result, combined with ternary structural data concerning the connection from adenosine to guanosine, prompted us to further examine whether cGAS would ultimately have a preference for generating a 2',5' or 3',5' link for cyclization.

We observed a single HPLC peak, distinct from two cyclic-GA dinucleotide reference molecules (either both 2',5' or both 3',5' linkages) and coincident with c[G(2',5')pA (3',5')p], as the product of dsDNA-dependent cGAS activity (FIG. 6A). This conclusion was validated from an independent NMR study (FIG. 6C). While biological production of cyclic dinucleotides appears evolutionarily conserved from prokaryotes to eukaryotes, their formation based on the chemical linkages is distinct. In the case of cGAS, formation of c[G(2',5')pA(3',5')p] appears similar to the 2',5' oligoadenylates generated by OAS but also to the 3',5' dinucleotide linkages created by bacterial cyclases (Sadler and Williams, 2008; Kodym et al. 2009; Donovan et al. 2013).

Potential Benefits of 2',5' (GA Step) and 3',5' (AG Step) Linkages in c[G(2',5)pA(3',5)p]

It is not clear why cGAS prefers to generate both a 2',5' (GpA step) and 3',5' (ApG step) cyclic GA-dinucleotide. A 2',5' phosphodiester bond is uncommon and few nucleases are known to be able to hydrolyze such a linkage (Kubota et al. 2004). Without wishing to be bound by any particular theory, 2',5' linkages might promote greater stability in cells to enable effective transduction of the second messenger, but the 3',5' linkage may facilitate its breakdown by numerous conventional endonucleases to prevent prolonged interferon response. Taken together, our structure and functional studies have identified the chemical nature of metazoan cGAMP, highlighting the role of 2',5' linkages in second messengers that activate the type I interferon pathway.

Implications of cGAS dsDNA-Binding Mutants

Structural studies have identified intermolecular protein-DNA contacts on formation of the cGAS-dsDNA complex (FIG. 1C). Since these are primarily of an electrostatic nature and involve non-specific recognition of the DNA phosphodiester backbone, they have been classified into three sets of triple mutants, with the in vitro (FIG. 7A) and cellular assays (FIG. 7B) establishing complete loss in activity and ability to stimulate interferon production for the S165A, N172A, K372A triple mutant, the N196A, Y200A, K372A triple mutant and the R158A, R161A, K395A triple mutant, and partial loss in activity for the S165A, N172A, Y200A triple mutant. This reinforces the importance of complex formation between cGAS and dsDNA for the catalytic activity of cGAS.

Implications of cGAS Catalytic Pocket Mutants

Structural studies of ternary complexes of cGAS and dsDNA with bound NTPs have identified Glu211, Asp213, Asp307 as important catalytic residues for phophodiester bond formation. All three catalytic acidic residues are functionally dead on replacement by Ala as observed in either in vitro (FIG. 7A; Glu211A) or cellular (FIG. 7C, all three catalytic residues) assays, while the S199A mutation retained substantial activity. Tyr421 is involved in stacking interactions with A, while Arg364 is hydrogen bonded with G in the cGAMP ternary complex (FIG. 4B, C). Dual mutation of Y421A, R364A result in loss in the majority of activity in cellular assays (FIG. 7C).

Role of Divalent Cations

Structural studies of ternary complexes of dsDNA-bound cGAS with ligands have shown that the triphosphate moieties of ATP (FIG. 2E, F) and 5'-pppG(2',5')pG (FIG. 3B, C) are coordinated to a pair of cations (tentatively assigned to $Mg^{2+}$). Indeed, functional studies have highlighted the importance of divalent cations to phosphodiester bond formation. Omission of divalent cations or use of EDTA prevented c[G(2',5')pA(3',5')p] formation, whereas $Mg^{2+}$ and $Mn^{2+}$ promoted cGAS activity (FIG. 5A).

Comparison with Cytoplasmic dsRNA Sensor OAS1

In a parallel study to our contribution, structural studies and biochemical assays have been recently reported on the characterization of the dsRNA sensor human oligoadenylate synthetase 1 (OAS1) which polymerizes ATP into linear 2',5'-linked oligoadenylate (Donovan et al. 2013). The crystallographic studies unequivocally demonstrated conformational transitions in OAS1 on proceeding from the free state (Hartmann et al. 2003) to the ternary complex with bound dsRNA and 2'-dATP (Donovan et al. 2013), which follow a similar pattern to those observed by us in this study for complex formation of cGAS with dsDNA and bound ligands. Thus, three catalytic Glu residues of OAS1 are brought into close proximity on formation of the ternary complex with dsRNA and 2'-dATP, thereby creating the coordination geometry for binding of two $Mg^{2+}$ ions and 2'-dATP (Donovan et al. 2013), similar to what we observe for the cGAS system. Given that the only available structures were for free OAS1 (Hartmann et al. 2003) and its ternary complex with dsRNA and bound ligand (Donovan et al. 2013), these authors were not in a position to determine how the conformational transition was partitioned between steps reflecting conversion from free OAS1 to the binary complex with dsRNA and conversion from the binary complex to the ternary complex in the presence of 2'-dATP. Our results on the cytosolic dsDNA sensor cGAS suggest that the major conformational transition will most likely be restricted for the step involving conversion of OAS1 from the free state to the dsRNA-binding complex, with minimal changes on addition of 2'-dATP to form the ternary complex.

In addition to similarities mentioned above, there are also differences in protein-nucleic acid recognition principles between the cGAS dsDNA sensor (our study) and the OAS1 dsRNA sensor (Donovan et al. 2013), in that cGAS targets the sugar-phosphate backbone of dsDNA within a central segment of the dsDNA duplex (FIG. 1C), while OAS1 targets the sugar-phosphate backbone of dsRNA by contacting two minor groove segments separated by 30 Å (Donovan et al. 2013). The helical parameters of dsRNA and dsDNA are very distinct, and different recognition principles are used in protein-dsRNA (reviewed in Lunde et al. 2007) and protein-dsDNA (reviewed in Huffman and Brennan, 2002) complexes. Nevertheless, common principles are utilized to generate the critical catalytic site architecture, which in turn couples nucleic acid recognition (dsRNA or dsDNA in the cytoplasm) with the cascade of downstream events leading to an antiviral state including type I interferon response (cGAS) and RNase L activation (OAS1).

Further, the formation of linear 2',5'-linked iso-RNA mediated by OAS1 parallels the formation of c[G(2',5')pA (3',5')p] containing 2',5' linkage at the GpA step by cGAS. Thus, unlike earlier sole emphasis on 3',5' linkages as observed previously for bacterial second messenger c-di-GMP (reviewed in Romling et al. 2013), we highlight that the metazoan second messenger c[G(2',5')pA(3',5')p] utilizes mixed linkages involving 2',5' at the GpA step and 3',5' at the ApG step.

cGAS Contains a Single Active Site for Step-Wise Phosphodiester Bond Formation

Previous studies have established that diguanylate cyclase PleD forms a head-to-tail homodimer to form a reaction center at its interface, so that the intermediate does not have to change its orientation on the pathway to form c-di-GMP (Chan et al. 2004). By contrast, in our current studies of ternary complexes of cGAS, dsDNA and bound ligands, we observe no evidence for dimer or higher order oligomer formation in the crystal. Further, the ligand-binding pocket in our structures is buried within the cGAS topology and is not located on the surface, as it is in PleD (Chan et al. 2004).

Indeed, cGAS contains a single active site for the sequential phosphodiester bond formation steps, a feature quite remarkable given that the ligands are GTP and ATP and that the GpA linkage which forms first is 2'-5' and the ApG linkage which forms second is 3',5', resulting in generation of c[G(2',5')pA(3',5')p]. Without wishing to be bound by any particular theory, we outline a model for formation of c[G(2',5')pA(3',5')p] from GTP and ATP within the single catalytic pocket of dsDNA-bound cGAS in FIG. 7D. In this model, the first step involves formation of a 5'-pppGpA intermediate followed in the second step by formation of c[G(2',5')pA(3',5')p]. Note, also that the bound ligand is believed to undergo two flip-overs on the pathway to c[G (2',5')pA(3',5')p] formation.

Implications for the Di-Nucleotide Cyclase DncV

In an earlier study, the bacterial dinucleotide cyclase DncV was shown to generate cyclic GMP-AMP (cGAMP) (Davies et al. 2012). This first report on formation of cGAMP raises the interesting question as to the nature of the pair of phosphodiester linkages in this bacterial system.

Example 6

NMR Spectral Analysis of Synthesized cGAMP Linkage Isomers

Lyophilized cGAMP linkage isomers were dissolved in 99.9% $D_2O$ in 10 mM $K_2HPO_4$—$KH_2PO_4$ (pH 6.6) buffer. All NMR experiments are conducted at 35° C. on a Bruker 900 MHz spectrometer at New York Structural Biology Center. Resonance assignments are made based on HMBC (2 s recycling delay, 0.8 s $^1H$ acquisition time, 20 ms $^{13}C$ acquisition time, phase-insensitive $^{13}C$ acquisition, and anti-phase $^1H$ detection with absolute value mode processing), double-quantum filtered COSY (2 s recycling delay, 0.8 s direct acquisition time, 12 ms indirect acquisition time), and HSQC experiments (1 s recycling delay, 48 ms $^1H$ acquisition time, 20 ms $^{13}C$ acquisition time). The 1D proton spectra with water presaturation are accumulated over 8 scans for the synthesized cGAMP linkage isomers standards and 128 scans for the bio-enzymatically produced cGAS reaction.

Example 7

Thin Layer Chromatography (TLC) Analysis
Preparation of Oligonucleotides for TLC Assays Oligonucleotides used for biochemical assays of cGAS nucleotidyltransferase activity are listed in Table S6. Oligodeoxynucleotides were synthesized in-house using a 3400 DNA synthesizer (Applied Biosystems), oligoribonucleotides were purchased (Dharmacon). Double-stranded DNA, RNA, and DNA/RNA duplexes were annealed in 70 mM Tris-HCl pH 7.6, 10 mM $MgCl_2$, 5 mM DTT, at equimolar concentrations by incubation initiated at 95° C. followed by a 0.1° C. decrease per second to 25° C. in a Peltier thermoycler (MJ Research), and verified for annealing by agarose gel electrophoresis prior to use.

TLC Analysis of c[G(2',5)pA(3',5)p] Formation

Purified recombinant full length (fl, amino acids 1-507) and truncated (tr, amino acids 147-507) murine cGAS, including truncated mutant versions 1-6, were incubated in 20 µL reactions containing: 1 µM cGAS, 3.3 µM dsDNA, 5 mM $MgCl_2$, 150 mM NaCl, 20 mM Tris-HCl, pH 7.5 at 25° C., 1 mM DTT, 10% glycerol, 1 mM each of nucleotides (typically ATP and GTP), and $\alpha^{32}P$ or $\gamma^{32}P$ radiolabelled NTPs or dNTPs at 37° C. for 40 min. Reactions were stopped by addition of 20 µL of 50 mM EDTA. 2 µL of reaction solution was spotted onto high-performance TLC plates (HPTLC silica gel, 60 Å pores, $F_{254}$, 10×10 cm, cat #1.05628.0001, EMD Millipore) and products were separated with Solvent 1 ($NH_4HCO_3:C_2H_5OH:H_2O$ [0.2 M:30%:70%], w:v:v) or 2 ($NH_4HCO_3:C_2H_5OH:H_2O$ [0.025 M:30%:70%], w:v:v) at 25° C. for 1 h. Reaction products were visualized by UV (254 nm) and phosphorimaging (Typhoon FLA 9500, GE Healthcare). Images were processed using Adobe Photoshop and Illustrator CS5. The TLC conditions used were largely based on a protocol established to separate 3',5' cAMP (Higashida et al, 2012).

Example 8

Quantitation of cGAS Reaction Products

The yield of c[G(2',5')pA(3',5')p] generated was calculated by densitometry analysis of TLC experiments, using FIJI (ImageJ 1.47i) or spectrophotometrically (absorbance at 260 nm, $E_{260}=25.4\times10^3$) after purification from HPLC. For densitometry analyses, the fraction of $\alpha^{32}P$-labelled c[G(2', 5')pA(3',5')p] over total radioactivity per lane (c[G(2',5')pA (3',5')p]plus remaining $\alpha^{32}P$-labelled ATP or GTP) was calculated.

Example 9

Preparation of cGAS Reaction Products for High-Performance Liquid Chromatography Analysis In vitro generated c[G(2',5')pA(3',5')p] reaction products, or washed and dissolved cGAS crystals, were treated with 25 units of Benzonase (Novagen, cat. #70746, Purity >90%) for 30 min at 37° C., heat inactivated for 10 min at 95° C., then centrifuged at 21,000 g for 15 min (Sorvall Legend Micro 21R, Thermo Scientific); the supernatant was used for HPLC analysis. Reaction products, with or without 3-8 nmoles of chemically synthesized all 3',5' cGAMP, all 2',5' cGAMP, or c[G(2',5')pA(3',5')p] were subjected to reverse-phase HPLC analysis (AKTA Purifier, GE Healthcare) using a C18 column (25 cm×4.5 mm, 5 µM pore, Supelco Analytical). Analytes were monitored by UV 260 and 280 nm. A 0-10% solvent B (2 column volume), 10-50% solvent B (2 column volume) two-step linear gradient was used; solvent A (triethylammonium acetate:acetonitrile:$H_2O$ [0.1 M:3%:97%], w:v:v) and solvent B (methanol:acetonitrile: $H_2O$ [45%:45%: 10:], v:v:v).

Preparation of cGAS Reaction Product for 1D NMR Analysis

100 µl of in vitro generated c[G(2',5')pA(3',5')p] reaction product was benzonase and heat treated as before, prior to fractionation by HPLC. Three serial HPLC runs were performed (two 40 µl and one 20 µl reaction injection), and the peak corresponding to c[G(2',5')pA(3',5')p] was collected into a 15 ml falcon tube (approx. 4.5 ml total). Solvent removal was accomplished by vacuum centrifuge (Vacufuge, Eppendorf) for 3 days at room temperature until completely dry.

Example 10

Cellular Assays
Generation of cGAS Point Mutants

The murine cGAS CDS was inserted into a modified pMAX-cloning vector (Amaxa, Cologne, Germany). Site-directed mutagenesis was performed using the Quikchange method (Agilent, Santa Clara, Calif.) using Pfu Ultra Hot Start DNA Polymerase (Agilent) or KOD Hot Start DNA Polymerase (Merck, Darmstadt, Germany). The murine STING CDS and Firefly Luciferase (Promega, Madison, Wis.) were cloned into an EF1-promoter-modified pLenti6 (Invitrogen, Carlsbad, Calif.) expression plasmid. pGL3 IFN-beta Gluc reporter was obtained from Brian Monks (Institute of Innate Immunity, University of Bonn, Germany). All constructs were verified by sequencing of the CDS.

Luciferase Assay $3 \times 10^4$ HEK293 cells per 96-well were reverse-transfected in triplicates with a mixture of pGL3-IFNbeta-Gluc (50 ng), pLenti-EF1-Fluc (25 ng), pLenti-EF1-mSTING (25 ng) and cGAS-expression plasmid (25 ng, pMAX-cGAS WT or mutants) or Control plasmid pMAX-GFP (Amaxa) using Trans-IT LT1 (MirusBio, Madison, Wis.). After 36 h cells were lysed in passive lysis buffer. Firefly and gaussia Luciferase activities were determined on an EnVision reader (Perkin Elmer, Waltham, Mass.) using the respective substrates D-luciferin and coelenterazine (PJK GmbH, Kleinblittersdorf, Germany). IFNbeta-Gluc values were normalized to constitutive firefly luciferase values and fold induction was calculated in relation to control-plasmid pMAX-GFP.

Example 11

Synthesis of Cyclic GA-Dinucelotides

Preparation of all 2',5'-cGAMP (6, FIG. 14), c[G(2',5')pA(3',5')p] (11, FIG. 14), and all 3',5'-cGAMP (15, FIG. 14) were carried out using the procedure previously reported by the Jones laboratory (Gaffney et al. 2010; Gaffney and Jones 2012). To adenosine phosphoramidite, 1 or 7, (0.784 g, 0.793 mmol) dissolved in 5 mL of $CH_3CN$ and water (0.028 mL, 1.6 mmol, 2 equiv) was added pyridinium trifluoroacetate (0.184 g, 0.95 mmol, 1.2 equiv). After 1 min, 6 mL of tert-$BuNH_2$ was added. After another 10 min, the mixture was concentrated. To the residue dissolved in 10 mL of $CH_2Cl_2$ was added $H_2O$ (0.14 mL, 7.9 mmol, 10 equiv), followed by 10 mL of 6% dichloroacetic acid (DCA, 7.5 mmol) in $CH_2Cl_2$. After 10 min, the reaction was quenched by addition of pyridine (1.2 mL, 15 mmol, 2 equiv rel to DCA). The mixture was then concentrated, and the residue was dissolved in 7 mL of $CH_3CN$ and concentrated again. This process was repeated two more times, the last time leaving the A H-phosphonate, 2 or 8, in 2 mL. To this solution was added a dried solution of G amidite, 3 or 12 (1.00 g, 1.03 mmol, 1.3 equiv) in 3 mL $CH_3CN$. After 2 min, anhydrous tert-butyl hydroperoxide 5.5 M in decane (0.43 mL, 2.4 mmol, 3 equiv) was added. After 30 min, 0.20 g of $NaHSO_3$ dissolved in 0.5 mL $H_2O$ was added. The mixture was stirred for 5 min, and then concentrated. The residual oil was dissolved in 14 mL of $CH_2Cl_2$, followed by addition of $H_2O$ (0.15 mL, 8.5 mmol, 10 equiv) and then 14 mL of 6% DCA (9.8 mmol) in $CH_2Cl_2$. After 10 min, the reaction was quenched with 9 mL of pyridine. The mixture was concentrated to a small volume, 25 mL more pyridine was added, and the solution was concentrated again, leaving the linear dimer, 4, 9, or 13, in 17 mL. To this solution was added 5,5-dimethyl-2-oxo-2-chloro-1,3,2-dioxaphosphinane (DMOCP, 0.54 g of 95% reagent, 2.8 mmol, 3.5 equiv). After 10 min, the reaction was quenched by addition of $H_2O$ (0.50 mL, 28 mmol, 10 equiv rel to DMOCP), and $I_2$ (0.26 g, 1.0 mmol, 1.3 equiv) was added immediately. After 5 min, the mixture was poured into 120 mL of $H_2O$ containing 0.17 g $NaHSO_3$. After 5 min of stirring, 3.4 g of $NaHCO_3$ was slowly added. After 5 min more of stirring, the aqueous solution containing solid was partitioned with 135 mL 1:1 EtOAc:$Et_2O$. The separated aqueous layer was then partitioned with an additional 35 mL of 1:1 EtOAc:$Et_2O$.

The organic layers containing 5, 10, or 14 were combined and concentrated to an oil. For 14, the oil was dissolved in 5 mL $CH_3CN$ and the cyanoethyl group was removed by addition of 5 mL of tert-$BuNH_2$ for 10 min. The residue was purified on a 80 g $SiO_2$ column, using a gradient of 0 to 25% $CH_3OH$ in $CH_2Cl_2$ over 50 min. 5 and 10 were directly purified on $SiO_2$ without tert-$BuNH_2$ treatment. In each case the residue after purification was treated with 21 mL of $CH_3NH_2$ in anhydrous EtOH (33% by weight, 168 mmol, 212 equiv rel to the amino protecting groups). After 4 h at room temperature, the mixture was concentrated to a solid, to which 3 mL of pyridine and 1 mL of $Et_3N$ were added. The mixture was concentrated to an oil, and this process was repeated two more times to convert the tert-$BuNH_3^+$ to the $Et_3NH^+$ salt. To the oil was added 1 mL of pyridine, and the flask was placed in an oil bath at 55° C. $Et_3N$ (7.5 mL) and $Et_3N.3HF$ (2.6 mL, 48 mmol $F^-$, 30 eq rel to each TBS) were added simultaneously. The mixture was stirred at 55° C. After 3 h, the flask was removed from the oil bath and HPLC grade acetone (70 ml) was slowly added to the stirring mixture. After 10 min, the solid was collected by filtration, washed 5× with 3 mL portions of acetone, and dried in a desiccator over KOH overnight. This process gave pure 15, but 6 and 11 were purified on a 19×300 mm Prep Nova-Pak C18 column using a gradient of 2 to 20% $CH_3CN$ in 0.1 M $NH_4HCO_3$.

Analytical reversed phase HPLC was carried out on a Waters 2965 system with a photodiode array detector, using an Atlantis C18 column, 100 Å, 4.6 mm×50 mm, 3.0 µm. Gradients of $CH_3CN$ and 0.1 M triethylammonium acetate buffer (pH 6.8) were used with a flow rate of 1.0 mL/min. Low resolution ESI-MS was routinely acquired using a Waters Micromass single quadrupole LCZ system. LCMS of 6, 11, and 15 displayed m/z (M-H) 673 (calculated for $C_{20}H_{23}N_{10}O_{13}P_2^-$: 673).

Example 12

STING-Dependent Induction of Murine Alpha-Interferon and Human CXCL10 by cGAMP Compounds.
THP-1 Culture and Assay Conditions THP-1 cells were cultured in RPMI1640 with 10% FBS, sodium pyruvate and penicillin/streptomycin (Gibco, Life Technologies). $8 \times 10^4$ cells were plated per 96-well in 100 µl of Medium and equilibrated for 2 h at 37° C./5% CO2. To generate macrophage-like cells, 8×104 THP-1 cells were differentiated overnight with 10 ng/ml PMA (Sigma), medium was changed and cells were incubated for additional 24 h prior to stimulation.

BMDM Culture and Assay Conditions

Bone marrow derived macrophage cells (BMDM) were flushed from femurs of C57BL/6 mice. Erythrocytes were lysed (PharmLyse, BD Biosciences) and 1×107 cells per Petri dish were incubated in DMEM 10% FBS, sodium pyruvate and penicillin/streptomycin (Gibco, Life Technologies) with 30% L929-supernatant for 7 days. Cells were harvested with PBS 2 mM EDTA and plated at a density of 1×105 cells per 96-well. BMDMs were digitonin-permeabilized or control-treated in the presence of indicated cGAMP concentrations for 30 min, then supplemented with fresh medium. Supernatants were taken after 18 h and cytokines were determined by ELISA.

Cell Permeabilization/Stimulation

Cell permeabilization for delivery of cyclic di-nucleotides was performed as previously described(Woodward et al., 2010). Briefly, supernatant was removed and cells were covered with 50 µl Perm-buffer (50 mM HEPES pH 7.0, 100 mM KCl, 3 mM MgCl2, 1 mM ATP, 0.1 mM GTP, 0.1 mM DTT, 85 mM sucrose, 0.2% BSA)+/−10 µg/ml digitonin and serial dilutions of cGAMP isomers, followed by 30 min incubation at 37° C. Perm-buffer was then removed and cells were covered with 100 µl of pre-warmed medium. Viability of permeabilized cells was >50% compared to untreated, as monitored by light microscopy and Cell Titer Blue (Roche).

Supernatants were collected 16 h after stimulation and cytokines were determined by ELISA and HEK-Blue™ IFN-α/β bioassay, respectively.

ELISA

Human CXCL-10 was determined by ELISA (BD Opteia human IP-10 ELISA-Set) according to manufacturer's recommendations. Murine Ifna was determined by sandwich-ELISA: Monoclonal rat-anti Ifna (clone RMMA-1) was used as capture antibody, recombinant Ifna was used as standard and polyclonal rabbit serum against Ifna for detection (all from PBL Interferon Source, Piscataway N.J., USA), followed by anti-rabbit HRP (Bio-Rad).

Fitting of Dose-Response Curves 4-parametric sigmoidal dose-response curves and EC50 values were analyzed with Graph Pad Prism (Graph Pad Software, La Jolla Calif., USA).

TABLE S4

Proton and carbon chemical shifts for cGAMPs

| | | c[G(3',5')pA(3',5')p] | c[G(2',5')pA(2',5')p] | c[G(2',5')pA(3',5')p] |
|---|---|---|---|---|
| Proton chemical shifts list | | | | |
| G | H8 | 7.96 | 7.85 | 7.86 |
| | H1' | 5.92 | 5.99 | 5.93 |
| | H2' | 4.72 | 5.31 | 5.62 |
| | H3' | 4.91 | 4.66 | 4.58 |
| | H4' | 4.39 | 4.45 | 4.39 |
| | H5' | 4.35 | 4.13 | 4.15 |
| | H5" | 4.07 | 4.21 | 4.22 |
| A | H8 | 8.35 | 8.21 | 8.31 |
| | H2 | 8.13 | 8.11 | 8.27 |
| | H1' | 6.11 | 6.29 | 6.17 |
| | H2' | 4.76 | 5.23 | 4.77 |
| | H3' | 4.92 | 4.69 | 5.03 |
| | H4' | 4.45 | 4.51 | 4.47 |
| | H5' | 4.38 | 4.16 | 4.45 |
| | H5" | 4.09 | 4.24 | 4.13 |
| Carbon chemical shifts list | | | | |
| G | C8 | 139.72 | 142.36 | 143.29 |
| | C5 | 118.97 | 119.88 | 120.06 |
| | C4 | 153.09 | 154.55 | 154.53 |
| | C1' | 92.23 | 89.13 | 88.90 |
| | C2' | 76.14 | 78.77 | 77.11 |
| | C3' | 73.18 | 73.87 | 74.05 |
| | C4' | 82.58 | 86.18 | 86.11 |
| | C5' | 65.03 | 67.59 | 68.38 |
| A | C8 | 142.13 | 142.57 | 141.61 |
| | C6 | 157.97 | 157.89 | 157.97 |
| | C5 | 121.44 | 121.10 | 121.47 |
| | C4 | 150.63 | 152.22 | 150.52 |
| | C2 | 155.32 | 155.08 | 155.05 |
| | C1' | 92.56 | 87.63 | 92.36 |
| | C2' | 76.23 | 82.04 | 76.58 |
| | C3' | 73.16 | 74.75 | 73.17 |
| | C4' | 82.75 | 87.03 | 82.68 |
| | C5' | 65.05 | 68.01 | 64.89 |

TABLE S5

Primers used in the Quickchange mutagenesis PCRs (Metabion, Martinsried, D):

| Primer Name | Sequence (5'-3') | SEQ ID NO: |
|---|---|---|
| N196A_Y200A | caaaggtgtggagcagctggccactggcagcgcctatgaacatgtgaagatt | 1 |
| N196A_Y200A_antisense | aatcttcacatgttcataggcgctgccagtggccagctgctccacacctttg | 2 |
| K372A | cctctctttctctcacactgaagcgtacattttgaataatcacggg | 3 |
| K372A_antisense | cccgtgattattcaaaatgtacgcttcagtgtgagagaaagagagg | 4 |
| S165A | ttgaaacgcaaagatatcgcggaggcggccg | 5 |
| S165A_antisense | cggccgcctccgcgatatctttgcgtttcaa | 6 |
| N172A | ggcggccgagacggtggctaaagttgtggaacgc | 7 |
| N172A_antisense | gcgttccacaactttagccaccgtctcggccgcc | 8 |
| Y200A | gcagctgaacactggcagcgcctatgaacatgtgaagatt | 9 |
| Y200A_antisense | aatcttcacatgttcataggcgctgccagtgttcagctgc | 10 |
| R158A_R161A | agaaggtgctggacaaattggcattgaaagccaaagatatctcggaggcgg | 11 |
| R158A_R161A_antisense | ccgcctccgagatatctttggctttcaatgccaatttgtccagcaccttct | 12 |
| K395A | aatcttccggagcaaaatgctgcagagcagaatgtttaaaattaatgaaatacc | 13 |
| K395A_antisense | ggtatttcattaattttaaacattctgctctgcagcattttgctccggaagatt | 14 |
| R161A | ggacaaattgagattgaaagccaaagatatctcggaggcg | 15 |
| R161A_antisense | cgcctccgagatatctttggctttcaatctcaatttgtcc | 16 |
| G198P_S199A | gtggagcagctgaacactgccgcctactatgaacatgtgaag | 17 |
| G198P_S199A_antisense | cttcacatgttcatagtaggcggcagtgttcagctgctccac | 18 |
| G198A | ggagcagctgaacactgccagctactatgaacatg | 19 |
| G198A_antisense | catgttcatagtagctggcagtgttcagctgctcc | 20 |
| G198P | gtggagcagctgaacactcccagctactatgaacatgt | 21 |
| G198P_antisense | acatgttcatagtagctgggagtgttcagctgctccac | 22 |
| G198P_G199A | ggtgtggagcagctgaacactcccgcctactatgaacatgtgaagatt | 23 |
| G198P_S199A_antisense | aatcttcacatgttcatagtaggcgggagtgttcagctgctccacacc | 24 |
| S199A | ggagcagctgaacactggcgcctactatgaacatgtgaag | 25 |
| S199A_antisense | cttcacatgttcatagtaggcgccagtgttcagctgctcc | 26 |
| E211A | tgtgaagatttctgctcctaatgcatttgatgttatgtttaaactgg | 27 |
| E211A_antisense | ccagtttaaacataacatcaaatgcattaggagcagaaatcttcaca | 28 |
| K402A | gcaaaatgctgcagaaaagaatgtttaaaattaatggcatacctttggaacagttgaaaaaa | 29 |
| K402A_antisense | ttttttcaactgttccaaaggtatgccattaattttaaacattcttttctgcagcattttgc | 30 |
| S420A | ttcaagagctggatgcattctgtgcctaccatgtga | 31 |
| S420A_antisense | tcacatggtaggcacagaatgcatccagctcttgaa | 32 |
| E371A | gcctctctttctctcacactgcaaagtacattttgaataatcac | 33 |
| E371A_antisense | gtgattattcaaaatgtactttgcagtgtgagagaaagagaggc | 34 |
| K424A | gcattctgttcctaccatgtggcaactgccatctttcacatgtg | 35 |
| K424A_antisense | cacatgtgaaagatggcagttgccacatggtaggaacagaatgc | 36 |
| R364A | tcaaggagagacctgggccctctctttctctcac | 37 |

TABLE S5-continued

Primers used in the Quickchange mutagenesis PCRs (Metabion, Martinsried, D):

| Primer Name | Sequence (5'-3') | SEQ ID NO: |
|---|---|---|
| R364A_antisense | gtgagagaaagagagggcccaggtctctccttga | 38 |
| Y421A | gctggatgcattctgttccgcccatgtgaaaactgccatc | 39 |
| Y421A_antisense | gatggcagttttcacatgggcggaacagaatgcatccagc | 40 |
| mcGASfwXhoI | atatatctcgagatggaagatccgcgtagaagga | 41 |
| mcGASrevBglII | atatatagatctctatcaaagcttgtcaaaaattggaaacccat | 42 |

TABLE S6

Oligonucleotides utilized for TLC analyses:

| Oligonucleotide Name | Sequence (5'-3') | SEQ ID NO: |
|---|---|---|
| 45 mer DNA (top strand) | tacagatctactagtgatctatgactgatctgtacatgatctaca | 43 |
| 45 mer DNA (bottom strand) | tgtagatcatgtacagatcagtcatagatcactagtagatctgta | 44 |
| 45 mer RNA (top strand) | uacagaucuacuagugaucuaugacugaucuguacaugaucuaca | 45 |
| 45 mer RNA (bottom strand) | uguagaucauguacagaucagucauagaucacuaguagaucugua | 46 |
| 17 mer DNA (top strand) | aaattgccgaagacgaa | 47 |
| 17 mer DNA (bottom strand) | tttcgtcttcggcaatt | 48 |
| 36 mer DNA (top strand) | acacacacacacacacacacacacacacacacacac | 49 |
| 36 mer DNA (bottom strand) | ctctctctctctctctctctctctctctctctctct | 50 |

Bold and underlined nucleotides represent 8-oxoguanosines that were utilized in separately generated modified oligos. Oligonucleotides were synthesized in-house 3400 DNA synthesizer (Applied Biosystems) or purchased (Dharmacon).

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr. D Biol. Crystallogr. 66, 213-221.

Burckstummer, T., Baumann, C., Blumi, S., Dixit, E., Durnberger, G., Jahn, H., Planyavsky, M., Bilban, M., Colinge, J., Bennet, K. L. et al. (2009). An orthogonal proteomic-genomic screen identifies AIM2 as a cytoplasmic DNA sensor for the inflammasome. Nat. Immunol. 10, 266-272.

Chan, C., Paul, R., Samoray, D., Amiot, N. C., Giese, B., Jenal, U. and Schirmer, T. (2004). Structural basis of activity and allosteric control of diguanylate cyclase. Proc. Natl. Acad. Scis. USA. 101, 17084-17089.

Davies, B. W., Bogard, R. W., Young, T. S., and Mekalanos, J. J. (2012). Coordinated regulation of accessory genetic elements produces cyclic di-nucleotides for V. cholerae virulence. Cell 149, 358-370.

Donovan, J., Dufner, M., and Korennykh, A. (2013). Structural basis for cytosolic double-stranded RNA surveillance by human oligoadenylate synthetase 1. Proc. Natl. Acad. Sci. USA 110, 1652-1657.

Egli, M., Gessner, R. V., Williams, L. D., Quigley, G. J., van der Marel, G. A., van Boom, J. H., Rich, A., and Frederick, C. A. (1990). Atomic-resolution structure of the cellulose synthase regulator cyclic diguanylic acid. Proc. Natl. Acad. Sci. USA 87, 3235-3239.

Emsley, P., Lohkamp, B., Scott, W. G., and Cowtan, K. (2010). Features and development of Coot. Acta Crystallogr. D Biol. Crystallogr. 66, 486-501.

Fernandes-Alnemri, T., Yu, J. W., Datta, P., Wu, J., and Alnemri, E. S. (2009). AIM2 activates the inflammasome and cell death in response to cytoplasmic DNA. Nature 458, 509-513.

Gaffney, B. L., and Jones, R. A. (2012). One-flask syntheses of cyclic diguanosine monophosphate (c-di-GMP). Current Protocols in Nucleic Acid Chemistry 14, 14.18.11-14.18.17.

Gaffney, B. L., Veliath, E., Zhao, J., and Jones, R. A. (2010). One-flask syntheses of c-di-GMP and the [Rp,Rp] and [Rp,Sp] thiophosphate analogues. Org Lett 12, 3269-3271.

Hartmann, R., Justesen, J., Sarkar, S. N., Sen, G. C., and Yee, V. C. (2003). Crystal structure of the 2'-specific and double-stranded RNA-activated interferon-induced antiviral protein 2'-5'-oligoadenylate synthetase. Mol. Cell 12, 1173-1185.

Higashida, H., Hossain, K. Z., Takahagi, H., and Noda, M. (2002). Measurement of adenylyl cyclase by separating cyclic AMP on silica gel thin-layer chromatography. Anal. Biochem. 308, 106-111.

Hornung, V., Ablasser, A., Charrel-Dennis, M., Bauernfeind, F., Horvath, G., Caffrey, D. R., Latz, E., and Fitzgerald, K. A. (2009). AIM2 recognizes cytosolic dsDNA and forms a caspase-1-activating inflammasome with ASC. Nature 458, 514-518.

Hornung, V., and Latz, E. (2010). Intracellular DNA recognition. Nat. Rev. Immunol. 10, 123-130.

Huang, Y. H., Liu, X. Y., Du, X. X., Jiang, Z. F., and Su, X. D. (2012). The structural basis for the sensing and binding of cyclic di-GMP by STING. Nat Struct Mol Biol 19, 728-730.

Huffman, J. L. and Brennan, R. G. (2002). Prokaryotic transcription regulators: more than just the helix-turn-helix motif. 12, 98-106.

Ishikawa, H., and Barber, G. N. (2008). STING is an endoplasmic reticulum adaptor that facilitates innate immune signalling. Nature 455, 674-678.

Jin, L., Waterman, P. M., Jonscher, K. R., Short, C. M., Reisdorph, N. A., and Cambier, J. C. (2008). MPYS, a novel membrane tetraspanner, is associated with major histocompatibility complex class II and mediates transduction of apoptotic signals. Mol. Cell Biol. 28, 5014-5026.

Jin, T., Perry, A., Jiang, J., Smith, P., Curry, J. A., Unterholzner, L., Jiang, Z., Horvath, G., Rathinam, V. A., Johnstone, R. W., et al. (2012). Structures of the HIN domain:DNA complexes reveal ligand binding and activation mechanisms of the AIM2 inflammasome and IFI16 receptor. Immunity 36, 561-571.

Keating, S. E., Baran, M., and Bowie, A. G. (2011). Cytosolic DNA sensors regulating type I interferon induction. Trends Immunol. 32, 574-581.

Kerur, N., Veettil, M. V., Sharma-Walia, N., Bottero, V., Sadagopan, S., Otageri, P., and Chandran, B. (2011). IFI16 acts as a nuclear pathogen sensor to induce the inflammasome in response to Kaposi Sarcoma-associated herpesvirus infection. Cell Host Microbe 9, 363-375.

Kodym, R., Kodym, E., and Story, M. D. (2009). 2'-5'-Oligoadenylate synthetase is activated by a specific RNA sequence motif. Biochem. Biophys. Res. Commun. 388, 317-322.

Krasteva, P. V., Giglio, K. M., and Sondermann, H. (2012). Sensing the messenger: the diverse ways that bacteria signal through c-di-GMP. Protein Sci. 21, 929-948.

Kubota, K., Nakahara, K., Ohtsuka, T., Yoshida, S., Kawaguchi, J., Fujita, Y., Ozeki, Y., Hara, A., Yoshimura, C., Furukawa, H. et al. Identification of 2'-phophodiesterase, which plays a role in 2-5 A system reulated by interferon. J. Biol. Chem., 279, 37832-37841.

Kulshina, N., Baird, N. J., and Ferre-D'Amare, A. R. (2009). Recognition of the bacterial second messenger cyclic diguanylate by its cognate riboswitch. Nat. Struct. Mol. Biol. 16, 1212-1217.

Lee, E. R., Baker, J. L., Weinberg, Z., Sudarsan, N., and Breaker, R. R. (2010). An allosteric self-splicing ribozyme triggered by a bacterial second messenger. Science 329, 845-848.

Lunde, B. M., Moore, C. and Varani, G. (2007). RNA-binding proteins: modular design for efficient function. Nat. Rev. Mol Cell. Biol. 8, 479-490.

McCoy, A. J., Grosse-Kunstleve, R. W., Adams, P. D., Winn, M. D., Storoni, L. C., and Read, R. J. (2007). Phaser crystallographic software. J. Appl. Crystallogr. 40, 658-674.

O'Neill, L. A. (2013). Immunology. Sensing the dark side of DNA. Science 339, 763-764.

Otwinowski, Z., and Minor, W. (1997). Processing of X-ray Diffraction Data Collected in Oscillation Mode. Methods in Enzymology 276, 307-326.

Ouyang, S., Song, X., Wang, Y., Ru, H., Shaw, N., Jiang, Y., Niu, F., Zhu, Y., Qiu, W., Parvatiyar, K., et al. (2012). Structural analysis of the STING adaptor protein reveals a hydrophobic dimer interface and mode of cyclic di-GMP binding. Immunity 36, 1073-1086.

Romling, U., Galperin, M. Y., and Gomelsky, M. (2013). Cyclic di-GMP: the First 25 Years of a Universal Bacterial Second Messenger. Microbiol. Mol. Biol. Rev. 77, 1-52.

Ross, P., Weinhouse, H., Aloni, Y., Michaeli, D., Weinberger-Ohana, P., Mayer, R., Braun, S., de Vroom, E., van der Marel, G. A., van Boom, J. H., et al. (1987). Regulation of cellulose synthesis in Acetobacter xylinum by cyclic diguanylic acid. Nature 325, 279-281.

Sadler, A. J., and Williams, B. R. (2008). Interferon-inducible antiviral effectors. Nat. Rev. Immunol. 8, 559-568.

Schirmer, T., and Jenal, U. (2009). Structural and mechanistic determinants of c-di-GMP signalling. Nat. Rev. Microbiol. 7, 724-735.

Shu, C., Yi, G., Watts, T., Kao, C. C., and Li, P. (2012). Structure of STING bound to cyclic di-GMP reveals the mechanism of cyclic dinucleotide recognition by the immune system. Nat. Struct. Mol. Biol. 19, 722-724.

Smith, K. D., Lipchock, S. V., Ames, T. D., Wang, J., Breaker, R. R., and Strobel, S. A. (2009). Structural basis of ligand binding by a c-di-GMP riboswitch. Nat. Struct. Mol. Biol. 16, 1218-1223.

Sudarsan, N., Lee, E. R., Weinberg, Z., Moy, R. H., Kim, J. N., Link, K. H., and Breaker, R. R. (2008). Riboswitches in eubacteria sense the second messenger cyclic di-GMP. Science 321, 411-413.

Sun, L., Wu, J., Du, F., Chen, X., and Chen, Z. J. (2013). Cyclic GMP-AMP synthase is a cytosolic DNA sensor that activates the type I interferon pathway. Science 339, 786-791.

Sun, W., Li, Y., Chen, L., Chen, H., You, F., Zhou, X., Zhou, Y., Zhai, Z., Chen, D., and Jiang, Z. (2009). ERIS, an endoplasmic reticulum IFN stimulator, activates innate immune signaling through dimerization. Proc. Natl. Acad. Sci. USA 106, 8653-8658.

Takaoka, A., Wang, Z., Choi, M. K., Yanai, H., Negishi, H., Ban, T., Lu, Y., Miyagishi, M., Kodama, T., Honda, K., et al. (2007). DAI (DLM-1/ZBP1) is a cytosolic DNA sensor and an activator of innate immune response. Nature 448, 501-505.

Unterholzner, L., Keating, S. E., Baran, M., Horan, K. A., Jensen, S. B., Sharma, S., Sirois, C. M., Jin, T., Latz, E., Xiao, T. S., et al. (2010). IFI16 is an innate immune sensor for intracellular DNA. Nat. Immunol. 11, 997-1004.

Wolkowicz, U. M., and Cook, A. G. (2012). NF45 dimerizes with NF90, Zfr and SPNR via a conserved domain that has a nucleotidyltransferase fold. Nucleic Acids Res. 40, 9356-9368.

Woodward, J. J., Iavarone, A. T., and Portnoy, D. A. (2010). c-di-AMP Secreted by Intracellular *Listeria monocytogenes* Activates a Host Type I Interferon Response. Science (New York, N.Y. 328, 1703-1705.

Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

Yang, P., An, H., Liu, X., Wen, M., Zheng, Y., Rui, Y., and Cao, X. (2010). The cytosolic nucleic acid sensor LRRFIP1 mediates the production of type I interferon via a beta-catenin-dependent pathway. Nat. Immunol. 11, 487-494.

Yin, Q., Tian, Y., Kabaleeswaran, V., Jiang, X., Tu, D., Eck, M. J., Chen, Z. J., and Wu, H. (2012). Cyclic di-GMP sensing via the innate immune signaling protein STING. Mol. Cell 46, 735-745.

Zhang, Z., Yuan, B., Bao, M., Lu, N., Kim, T., and Liu, Y. J. (2011). The helicase DDX41 senses intracellular DNA mediated by the adaptor STING in dendritic cells. Nat. Immunol. 12, 959-965.

Zhong, B., Yang, Y., Li, S., Wang, Y. Y., Li, Y., Diao, F., Lei, C., He, X., Zhang, L., Tien, P., et al. (2008). The adaptor protein MITA links virus-sensing receptors to IRF3 transcription factor activation. Immunity 29, 538-550.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

We claim:

1. A pharmaceutical composition comprising a compound of Formula II:

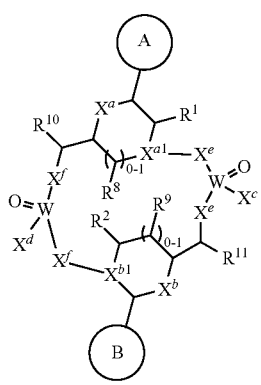

II or a pharmaceutically acceptable salt thereof, and a pharmaceutically acceptable carrier, wherein:

Ring A is selected from the group consisting of:

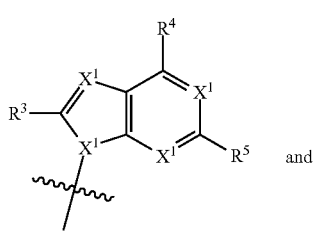

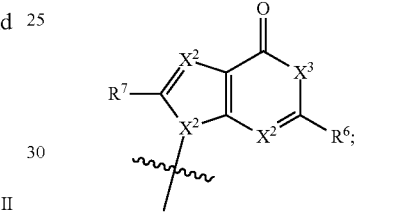

Ring B is selected from the group consisting of:

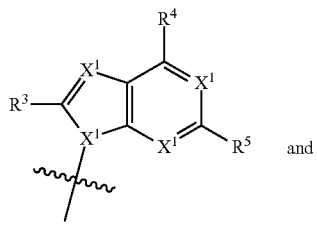

and

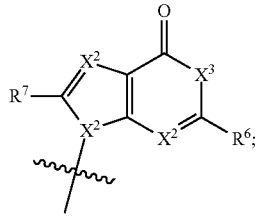

each $X^1$ and $X^2$ is independently —CR— or —N—, wherein each R is independently hydrogen or $C_{1-6}$ aliphatic;

$X^3$ is —NH—;

$X^a$ and $X^b$ are independently —O— or —S—;

$X^{a1}$ and $X^{b1}$ are —CH;

$X^c$ and $X^d$ are independently oxygen or sulfur;

each $X^e$ and $X^f$ is —O—;

each W is P;

each $R^1$ and $R^2$ is independently selected from the group consisting of hydrogen, halogen, —CN, —$OR^a$ wherein $R^a$ is hydrogen or $C_{1-6}$ aliphatic, —N(R)$_2$ wherein each R is independently hydrogen or $C_{1-6}$ aliphatic, and $C_{1-12}$ aliphatic optionally substituted with one or more substituents independently selected from the group consisting of halogen, —OR°, and —N(R°)$_2$, wherein each R° is independently hydrogen or $C_{1-6}$ aliphatic;

each $R^3$, $R^4$, $R^5$, $R^6$, and $R^7$ is independently selected from the group consisting of hydrogen, halogen, —CN, —OR wherein R is hydrogen or $C_{1-6}$ aliphatic, —SR wherein R is hydrogen or $C_{1-6}$ aliphatic, —N(R)$_2$ wherein each R is independently hydrogen or $C_{1-6}$ aliphatic, —C(O)N(R)$_2$ wherein each R is independently hydrogen or $C_{1-6}$ aliphatic, —NHC(O)R wherein R is hydrogen, $C_{1-6}$ aliphatic, or phenyl, and $C_{1-12}$ aliphatic optionally substituted with one or more substituents independently selected from the group consisting of halogen, —OR°, and —N(R°)$_2$, wherein each R° is independently hydrogen or $C_{1-6}$ aliphatic;

the subindex of the carbon atoms to which each $R^8$ and $R^9$ is attached is 0; and each $R^{10}$ and $R^{11}$ is independently hydrogen or $C_{1-2}$ alkyl.

2. The pharmaceutical composition of claim 1, wherein Ring A is

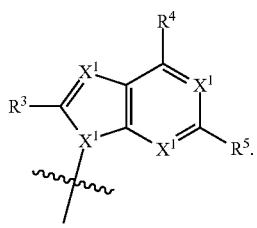

3. The pharmaceutical composition of claim 2, wherein Ring B is

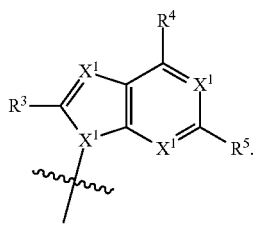

4. The pharmaceutical composition of claim 1, wherein Ring B is

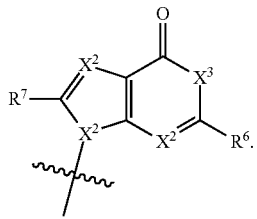

5. The pharmaceutical composition of claim 1, wherein each $X^1$ is —N—.

6. The pharmaceutical composition of claim 1, wherein each $X^2$ is —N—.

7. The pharmaceutical composition of claim 1, wherein $X^a$ is —O—.

8. The pharmaceutical composition of claim 1, wherein $X^b$ is —O—.

9. The pharmaceutical composition of claim 1, wherein $X^c$ and $X^d$ are both oxygen.

10. The pharmaceutical composition of claim 1, wherein $X^c$ and $X^d$ are both sulfur.

11. The pharmaceutical composition of claim 1, wherein each $R^1$ and $R^2$ is independently selected from the group consisting of hydrogen, halogen, —NH$_2$, and —OR$^a$, wherein $R^a$ is hydrogen or $C_{1-6}$ alkyl.

12. The pharmaceutical composition of claim 11, wherein at least one of $R^1$ and $R^2$ is —OH.

13. The pharmaceutical composition of claim 1, wherein each $R^1$ and $R^2$ is independently selected from the group consisting of hydrogen, halogen, —NH$_2$, and —OR$^a$, wherein $R^a$ is hydrogen or $C_{1-6}$ alkyl; and each $R^{10}$ and $R^{11}$ is hydrogen.

14. The pharmaceutical composition of claim 1, wherein each $R^3$, $R^4$, $R^5$, $R^6$, and $R^7$ is independently selected from the group consisting of hydrogen, halogen, —OH, —SH, —NH$_2$, and —C(O)NH$_2$.

15. The pharmaceutical composition of claim 14, wherein each $R^1$ and $R^2$ is independently selected from the group consisting of hydrogen, halogen, —NH$_2$, and —OR$^a$, wherein $R^a$ is hydrogen or $C_{1-6}$ alkyl.

16. The pharmaceutical composition of claim 1, wherein each $R^3$, $R^5$, and $R^7$ is independently selected from the group consisting of hydrogen and halogen.

17. The pharmaceutical composition of claim 16, wherein each $R^3$, $R^5$, and $R^7$ is hydrogen.

18. The pharmaceutical composition of claim 1, wherein each $R^4$ and $R^6$ is independently selected from the group consisting of hydrogen, halogen, and —NH$_2$.

19. The pharmaceutical composition of claim 18, wherein $R^4$ and $R^6$ are each —NH$_2$.

20. The pharmaceutical composition of claim 1, wherein $R^{10}$ and $R^{11}$ are hydrogen.

21. The pharmaceutical composition of claim 1, wherein the compound is of formula II-a:

II-a

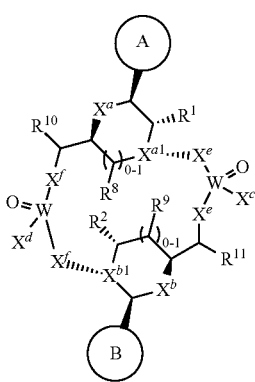

or a pharmaceutically acceptable salt thereof.

22. The pharmaceutical composition of claim 1, wherein the compound is of formula X, XI, XII, XIII, XIV, XV, or XVI:

121 122
-continued
X 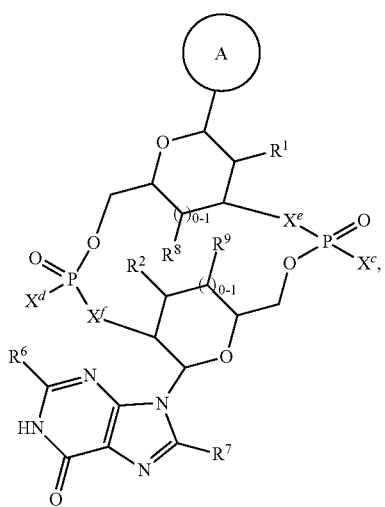 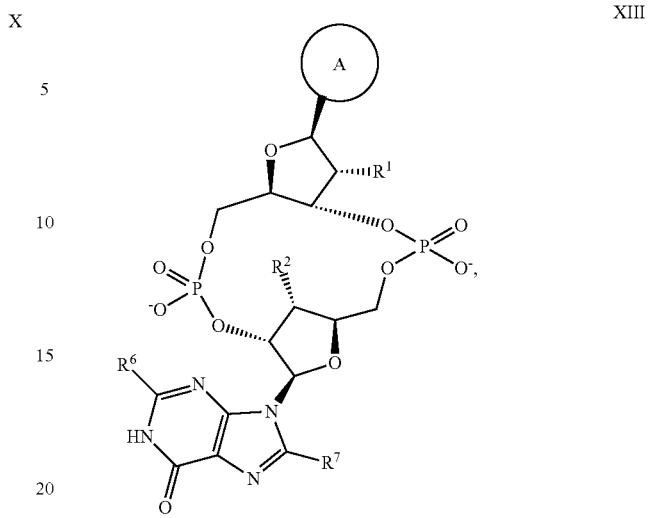 XIII
XI 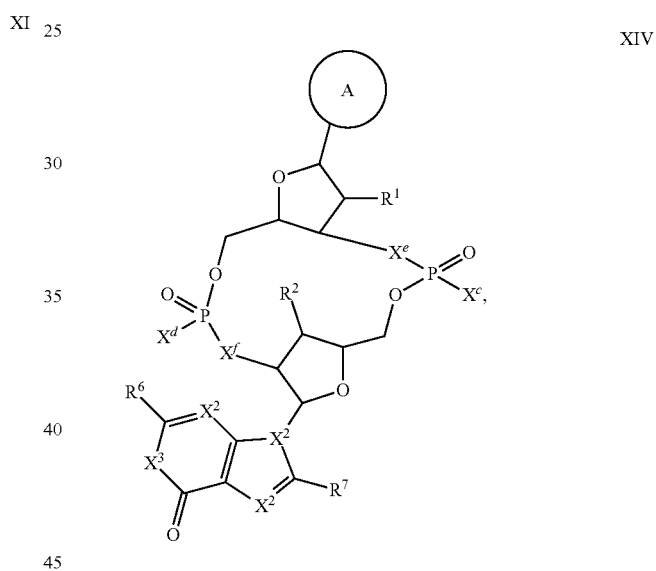 XIV
XII 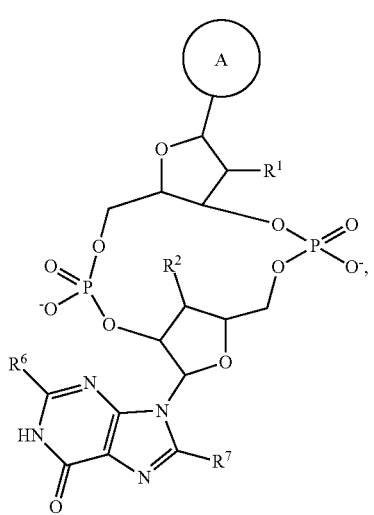 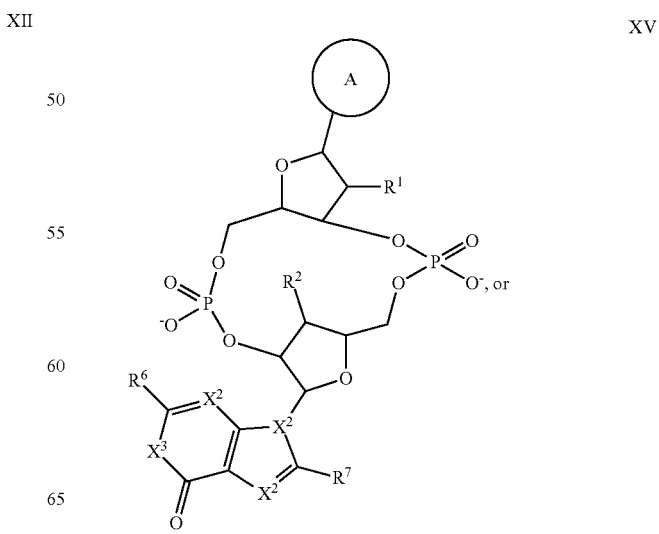 XV -continued

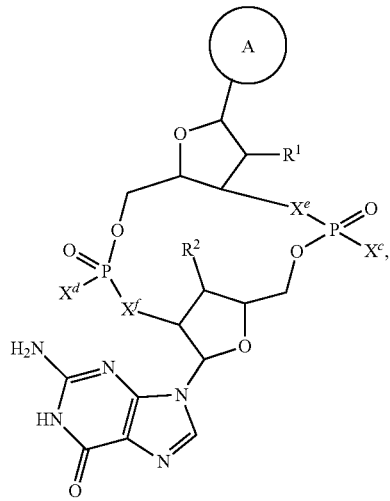

or a pharmaceutically acceptable salt thereof.

23. The pharmaceutical composition of claim 21, wherein:

Ring A is

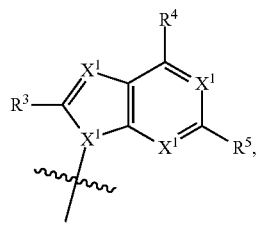

wherein each $X^1$ is —N—, $R^3$ and $R^5$ are hydrogen, and $R^4$ is —$NH_2$;

$X^a$ and $X^b$ are —O—;

$R^1$ and $R^2$ are —OH; and $R^{10}$ and $R^{11}$ are hydrogen.

24. The pharmaceutical composition of claim 23, wherein at least one of $X^c$ and $X^d$ is sulfur.

25. The pharmaceutical composition of claim 23, wherein both of $X^c$ and $X^d$ are oxygen.

26. The pharmaceutical composition of claim 23, wherein both of $X^c$ and $X^d$ are sulfur.

27. The pharmaceutical composition of claim 1, wherein the compound is of formula XIV:

XIV

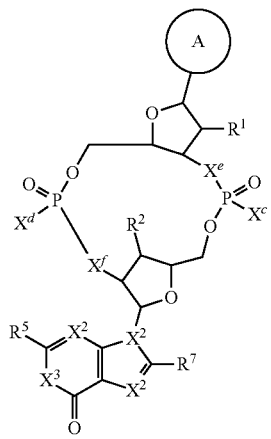

or a pharmaceutically acceptable salt thereof,
wherein:
  each $R^3$, $R^5$, and $R^7$ are independently hydrogen or halogen;
  each $R^4$ and $R^6$ are independently hydrogen, halogen, or —$NH_2$; and
  each $R^1$ and $R^2$ are independently selected from the group consisting of hydrogen, halogen, —$NH_2$, and —$OR^a$, wherein $R^a$ is hydrogen or $C_{1-6}$ alkyl.

28. The pharmaceutical composition of claim 1, wherein the compound is of formula XVI:

XVI

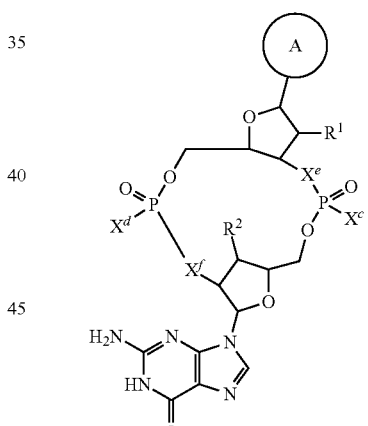

or a pharmaceutically acceptable salt thereof,
wherein:
  each $R^3$, $R^5$, and $R^7$ are independently hydrogen or halogen;
  each $R^4$ and $R^6$ are independently hydrogen, halogen, or —$NH_2$; and
  each $R^1$ and $R^2$ are independently selected from the group consisting of hydrogen, halogen, —$NH_2$, and —$OR^a$, wherein $R^a$ is hydrogen or $C_{1-6}$ alkyl.

29. The pharmaceutical composition of claim 1, wherein at least one of $X^c$ and $X^d$ is sulfur.

* * * * *